United States Patent
Chen et al.

(10) Patent No.: US 12,421,229 B2
(45) Date of Patent: Sep. 23, 2025

(54) HYDROPYRIDO[1,2-α]PYRAZINE COMPOUNDS FOR THE TREATMENT OF AUTOIMMUNE DISEASE

(71) Applicant: Hoffmann-La Roche Inc., Little Falls, NJ (US)

(72) Inventors: Jianguo Chen, Shanghai (CN); Fabian Dey, Zurich (CH); Hongtao Xu, Shanghai (CN); Weixing Zhang, Shanghai (CN); Wei Zhu, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 601 days.

(21) Appl. No.: 17/780,161

(22) PCT Filed: Dec. 1, 2020

(86) PCT No.: PCT/EP2020/083996
§ 371 (c)(1),
(2) Date: May 26, 2022

(87) PCT Pub. No.: WO2021/110614
PCT Pub. Date: Jun. 10, 2021

(65) Prior Publication Data
US 2023/0022297 A1    Jan. 26, 2023

(30) Foreign Application Priority Data
Dec. 3, 2019 (WO) ............... PCT/CN2019/122716

(51) Int. Cl.
C07D 471/04      (2006.01)
C07D 519/00      (2006.01)

(52) U.S. Cl.
CPC ......... *C07D 471/04* (2013.01); *C07D 519/00* (2013.01)

(58) Field of Classification Search
CPC ..................... C07D 471/04; C07D 519/00
USPC ..................................................... 514/248
See application file for complete search history.

(56) References Cited

U.S. PATENT DOCUMENTS

| | | | |
|---|---|---|---|
| 2015/0105370 A1 | 4/2015 | Carlson et al. | |
| 2018/0037570 A1 | 2/2018 | Sherer et al. | |
| 2022/0340597 A1 | 10/2022 | Zhu et al. | |

FOREIGN PATENT DOCUMENTS

| | | |
|---|---|---|
| WO | 2012/084704 A1 | 6/2012 |
| WO | 2015/057655 A1 | 4/2015 |
| WO | 2015/057659 A1 | 4/2015 |
| WO | 2017/106607 A1 | 6/2017 |
| WO | 2018/031434 A1 | 2/2018 |
| WO | 2019/125849 A1 | 6/2019 |
| WO | 2019/233941 A1 | 12/2019 |
| WO | 2019/238629 A1 | 12/2019 |
| WO | 2020/020800 A1 | 1/2020 |
| WO | 2020/064792 A1 | 4/2020 |
| WO | 2020/207991 A1 | 10/2020 |
| WO | 2021/084022 A1 | 5/2021 |
| WO | 2021/099284 A1 | 5/2021 |

OTHER PUBLICATIONS

"International Preliminary Report on Patentability—PCT/EP2020/083996" (Report Issuance Date: May 17, 2022; Chapter I), :pp. 1-10 (Jun. 16, 2022).
"International Search Report—PCT/EP2020/083996" (w/Written Opinion), :pp. 1-17 (Feb. 19, 2021).
USPTO, "U.S. Appl. No. 17/772,930 entitled 'Hydropyrazino[1,2-D][1,4]Diazepine Compounds for the Treatment of Autoimmune Disease', filed Apr. 28, 2022".
USPTO, "U.S. Appl. No. 17/777,260 entitled 'Hydro-1H-Pyrrolo[1,2-A]Pyrazine Compounds for the Treatment of Autoimmune Disease', filed May 16, 2022".

*Primary Examiner* — Kristin A Vajda
(74) *Attorney, Agent, or Firm* — Bradley E. Davis

(57) ABSTRACT

The present invention relates to compounds of formula (I) and pharmaceutically acceptable salts thereof. The compounds act as antagonists of the toll-like receptors TLR7, TLR8 and/or TLR9 and are thus useful in the treatment of systemic lupus erythematosus (SLE) and lupus nephritis.

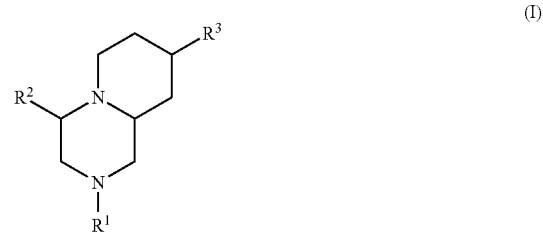

13 Claims, No Drawings

HYDROPYRIDO[1,2-α]PYRAZINE COMPOUNDS FOR THE TREATMENT OF AUTOIMMUNE DISEASE

CROSS-REFERENCE TO RELATED APPLICATIONS

This application is a National Stage Entry under 35 U.S.C. § 371 of International Application No. PCT/EP2020/083996, filed Dec. 1, 2020, which claims benefit of priority to Chinese Application No. PCT/CN2019/122716 filed Dec. 3, 2019, each of which is incorporated herein by reference in its entirety.

The present invention relates to organic compounds useful for therapy and/or prophylaxis in a mammal, and in particular to antagonist of TLR7 and/or TLR8 and/or TLR9 useful for treating systemic lupus erythematosus or lupus nephritis.

FIELD OF THE INVENTION

Autoimmune connective tissue disease (CTD) include prototypical autoimmune syndromes such as Systemic Lupus Erythematosus (SLE), primary Sjögren's syndrome (pSjS), mixed connective tissue disease (MCTD), Dermatomyositis/Polymyositis (DM/PM), Rheumatoid Arthritis (RA), and systemic sclerosis (SSc). With the exception of RA, no really effective and safe therapies are available to patients. SLE represents the prototypical CTD with a prevalence of 20-150 per 100,000 and causes broad inflammation and tissue damage in distinct organs, from commonly observed symptoms in the skin and joints to renal, lung, or heart failure. Traditionally, SLE has been treated with non-specific anti-inflammatory or immunosuppressive drugs. However, long-term usage of immunosuppressive drug, e.g. corticosteroids is only partially effective, and is associated with undesirable toxicity and side effects. Belimumab is the only FDA-approved drug for lupus in the last 50 years, despite its modest and delayed efficacy in only a fraction of SLE patients (Navarra, S. V. et al Lancet 2011, 377, 721.). Other biologics, such as anti-CD20 mAbs, mAbs against or soluble receptors of specific cytokines, have failed in most clinical studies. Thus, novel therapies are required that provide sustained improvement in a greater proportion of patient groups and are safer for chronic use in many auto-immune as well as auto-inflammation diseases.

Toll like Receptors (TLR) are an important family of pattern recognition receptors (PRR) which can initiate broad immune responses in a wide variety of immune cells. As natural host defense sensors, endosomal TLRs 7, 8 and 9 recognize nucleic acids derived from viruses, bacteria; specifically, TLR7/8 and TLR9 recognize single-stranded RNA (ssRNA) and single-stranded CpG-DNA, respectively. However, aberrant nucleic acid sensing of TRL7, 8, 9 is considered as a key node in a broad of autoimmune and auto-inflammatory diseases (Krieg, A. M. et al. Immunol. Rev. 2007, 220, 251. Jiménez-Dalmaroni, M. J. et al Autoimmun Rev. 2016, 15, 1. Chen, J. Q., et al. Clinical Reviews in Allergy & Immunology 2016, 50, 1.). Anti-RNA and anti-DNA antibodies are well-established diagnostic markers of SLE, and these antibodies can deliver both self-RNA and self-DNA to endosomes. While self-RNA complexes can be recognized by TLR7 and TLR8, self-DNA complexes can trigger TLR9 activation. Indeed, defective clearance of self-RNA and self-DNA from blood and/or tissues is evident in SLE (Systemic Lupus Erythematosus) patients. TLR7 and TLR9 have been reported to be upregulated in SLE tissues, and correlate with chronicity and activity of lupus nephritis, respectively. In B cells of SLE patients, TLR7 expression correlates with anti-RNP antibody production, while TLR9 expression with IL-6 and anti-dsDNA antibody levels. Consistently, in lupus mouse models, TLR7 is required for anti-RNA antibodies, and TLR9 is required for anti-nucleosome antibody. On the other hand, overexpression of TLR7 or human TLR8 in mice promotes autoimmunity and auto-inflammation. Moreover, activation of TLR8 specifically contributes to inflammatory cytokine secretion of mDC/macrophages, neutrophil NETosis, induction of Th17 cells, and suppression of Treg cells. In addition to the described role of TLR9 in promoting autoantibody production of B cells, activation of TLR9 by self-DNA in pDC also leads to induction of type I IFNs and other inflammatory cytokines. Given these roles of TLR9 in both pDC and B cells, both as key contributors to the pathogenesis of autoimmune diseases, and the extensive presence of self-DNA complexes that could readily activate TLR9 in many patients with autoimmune diseases, it may have extra benefit to further block self-DNA mediated TLR9 pathways on top of inhibition of TLR7 and TLR8 pathways. Taken together, TLR7, 8 and 9 pathways represent new therapeutic targets for the treatment of autoimmune and auto-inflammatory diseases, for which no effective steroid-free and non-cytotoxic oral drugs exist, and inhibition of all these pathways from the very upstream may deliver satisfying therapeutic effects. As such, we invented oral compounds that target and suppress TLR7, TLR8 and TLR9 for the treatment of autoimmune and auto-inflammatory diseases.

SUMMARY OF THE INVENTION

The present invention relates to novel compounds of formula (I),

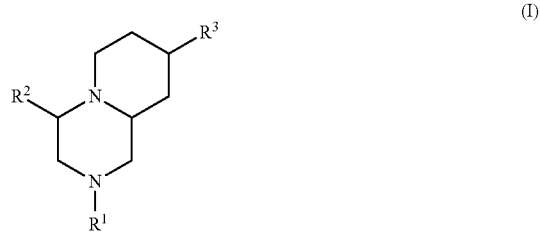

wherein
R$^1$ is

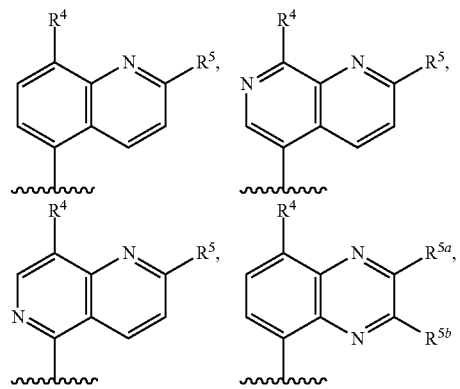

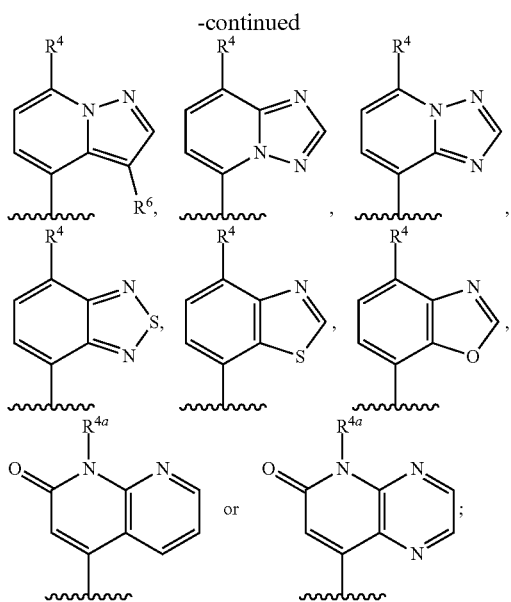

wherein R⁴ is $C_{1-6}$alkyl, $C_{1-6}$alkoxy, halo$C_{1-6}$alkyl, halogen, nitro or cyano; $R^{4a}$ is $C_{1-6}$alkyl or $C_{3-7}$cycloalkyl; $R^5$, $R^{5a}$ and $R^{5b}$ are independently selected from H and deuterium; $R^6$ is H or halogen;

$R^2$ is $C_{1-6}$alkyl;

$R^3$ is ((amino($C_{1-6}$alkoxy)pyrrolidinyl)phenyl)azetidinyl, (amino($C_{1-6}$alkoxy)pyrrolidinyl)pyridinyl, (amino($C_{1-6}$alkoxy)pyrrolidinyl)pyridinyloxy, (amino-1,4-oxazepanyl)pyridinyl, (aminoazetidinyl)pyridinyl, (morpholinyl$C_{1-6}$alkyl)phenyl, (morpholinyl$C_{1-6}$alkyl)phenylamino, (piperazinylphenyl)azetidinyl, (piperazinylphenyl)$C_{1-6}$alkylamino, aminohalopyrrolidinyl, morpholinylphenyl, morpholinylphenylamino, piperazinylphenyl, piperazinylpyridinyl, piperazinylpyridinyloxy, piperazinylpyrimidinyloxy or pyridinylpiperazinyl;

or a pharmaceutically acceptable salt thereof.

Another object of the present invention is related to novel compounds of formula (I). Their manufacture, medicaments based on a compound in accordance with the invention and their production as well as the use of compounds of formula (I) as TLR7 and/or TLR8 and/or TLR9 antagonist, and for the treatment or prophylaxis of systemic lupus erythematosus or lupus nephritis. The compounds of formula (I) show superior TLR7 and TLR8 and TLR9 antagonism activity. In addition, the compounds of formula (I) also show good cytotoxicity, phototoxicity, solubility, hPBMC, human microsome stability and SDPK profiles, as well as low CYP inhibition.

DETAILED DESCRIPTION OF THE INVENTION

Definitions

The term "$C_{1-6}$alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "$C_{1-6}$alkyl" groups are methyl, ethyl and n-propyl.

The term "halogen" and "halo" are used interchangeably herein and denote fluoro, chloro, bromo, or iodo.

The term "aryl" denotes an aromatic hydrocarbon mono- or bicyclic ring system of 5 to 12 ring atoms. Examples of aryl include, but not limited to, phenyl and naphthyl. Aryl can be further substituted by substituents includes, but not limited to $C_{1-6}$alkyl; 3,4,4a,5,7,7a-hexahydro-2H-pyrrolo[3,4-b][1,4]oxazinyl; 1,4-diazepanyl; 2,6-diazaspiro[3.3]heptanyl substituted by $C_{1-6}$alkyl; 5-oxa-2,8-diazaspiro[3.5]nonanyl; amino-1,4-oxazepanyl; azetidinyl substituted by one or two substituents independently selected from amino and $C_{1-6}$alkyl; piperazinyl unsubstituted or substituted by $C_{1-6}$alkyl; and pyrrolidinyl substituted by one or two substituents independently selected from amino, $C_{1-6}$alkoxy and halogen.

The term "heteroaryl" denotes an aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include, but not limited to, pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl or quinoxalinyl. Heteroaryl can be further substituted by substituents include, but not limited to $C_{1-6}$alkyl; 3,4,4a,5,7,7a-hexahydro-2H-pyrrolo[3,4-b][1,4]oxazinyl; 1,4-diazepanyl; 2,6-diazaspiro[3.3]heptanyl substituted by $C_{1-6}$alkyl; 5-oxa-2,8-diazaspiro[3.5]nonanyl; amino-1,4-oxazepanyl; azetidinyl substituted by one or two substituents independently selected from amino and $C_{1-6}$alkyl; piperazinyl unsubstituted or substituted by $C_{1-6}$alkyl; and pyrrolidinyl substituted by one or two substituents independently selected from amino, $C_{1-6}$alkoxy and halogen.

The term "heterocyclyl" or "heterocyclic" denotes a monovalent saturated or partly unsaturated mono or bicyclic ring system of 3 to 12 ring atoms, comprising 1 to 5 ring heteroatoms selected from N, O and S, the remaining ring atoms being carbon. In particular embodiments, heterocyclyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocyclyl are aziridinyl, oxiranyl, azetidinyl, oxetanyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl. Examples for bicyclic saturated heterocyclic ring are azabicyclo[3.2.1]octyl, quinuclidinyl, oxaazabicyclo[3.2.1]octanyl, azabicyclo[3.3.1]nonanyl, oxaaza-bicyclo[3.3.1]nonanyl, azabicyclo[3.1.0]hexanyl, oxodiazaspiro[3.4]octanyl, acetyloxodiazaspiro[3.4]octanyl, thiaazabicyclo[3.3.1]nonanyl, oxoazaspiro[2.4]heptanyl, oxoazaspiro[3.4]octanyl, oxoazabicyclo[3.1.0]hexanyl and dioxotetrahydropyrrolo[1,2-a]pyrazinyl. Examples for bicyclic heterocyclyl include, but not limited to, 1,2,3,4-tetrahydroisoquinolinyl; 5,6,7,8-tetrahydro-1,6-naphthyridinyl; 5,6,7,8-tetrahydro-1,7-naphthyridinyl; 5,6,7,8-tetrahydro-2,6-naphthyridinyl; 5,6,7,8-tetrahydro-2,7-naphthyridinyl; isoindolinyl; 3,4-dihydro-1H-2,6-naphthyridinyl; 7,8-dihydro-5H-1,6-naphthyridinyl; 4,5,6,7-tetrahydropyrazolo[3,4-c]pyridinyl; 6,7-dihydro-5H-pyrrolo[3,4-b]pyridinyl; 2,9-diazaspiro[5.5]undecanyl; 3,8-diazabicyclo[3.2.1]octanyl; 7,8-dihydro-5H-pyrido[3,4-b]pyrazinyl; 5,6,7,8-tetrahydropyrido[4,3-d]pyrimidinyl and 3,4-dihydro-1H-isoquinolinyl. Monocyclic or bicyclic heterocyclyl can be further substituted by amino, hydroxy, halogen, $C_{1-6}$alkyl, $C_{1-6}$alkoxy or heterocyclyl.

The term "heterocyclylheteroaryl" denotes heterocyclyl-heteroaryl-.

The term "heterocyclyl$C_{1-6}$alkylaryl" denotes heterocyclyl-$C_{1-6}$alkyl-aryl-.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "A pharmaceutically active metabolite" denotes a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

Antagonist of TLR7 and/or TLR8 and/or TLR9

The present invention relates to (i) a compound of formula (I),

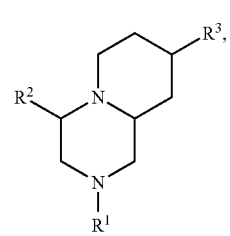

wherein
$R^1$ is

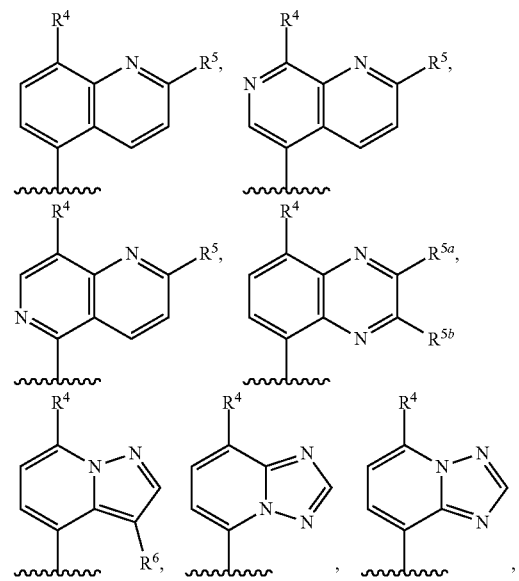

-continued

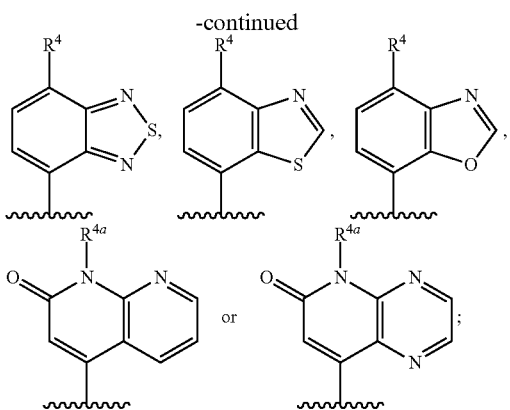

wherein R⁴ is $C_{1-6}$alkyl, $C_{1-6}$alkoxy, halo$C_{1-6}$alkyl, halogen, nitro or cyano; $R^{4a}$ is $C_{1-6}$alkyl or $C_{3-7}$cycloalkyl; $R^5$, $R^{5a}$ and $R^{5b}$ are independently selected from H and deuterium; $R^6$ is H or halogen;

R² is $C_{1-6}$alkyl;

R³ is ((amino($C_{1-6}$alkoxy)pyrrolidinyl)phenyl)azetidinyl, (amino($C_{1-6}$alkoxy)pyrrolidinyl)pyridinyl, (amino($C_{1-6}$alkoxy)pyrrolidinyl)pyridinyloxy, (amino-1,4-oxazepanyl)pyridinyl, (aminoazetidinyl)pyridinyl, (morpholinyl$C_{1-6}$alkyl)phenyl, (morpholinyl$C_{1-6}$alkyl)phenylamino, (piperazinylphenyl)azetidinyl, (piperazinylphenyl)$C_{1-6}$alkylamino, aminohalopyrrolidinyl, morpholinylphenyl, morpholinylphenylamino, piperazinylphenyl, piperazinylpyridinyl, piperazinylpyridinyloxy, piperazinylpyrimidinyloxy or pyridinylpiperazinyl;

or a pharmaceutically acceptable salt thereof.

Further embodiment of present invention is (ii) a compound of formula (I) according to (i), or a pharmaceutically acceptable salt thereof, wherein R¹ is

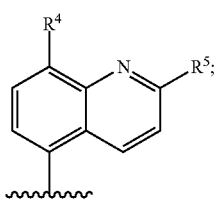

wherein R⁴ is cyano; R⁵ is H or deuterium.

A further embodiment of present invention is (iii) a compound of formula (I) according to (i) or (ii), or a pharmaceutically acceptable salt thereof, wherein R³ is ((3-amino-4-methoxy-pyrrolidin-1-yl)phenyl)azetidin-1-yl; (3-amino-4-methoxy-pyrrolidin-1-yl)-3-pyridinyl; (3-amino-4-methoxy-pyrrolidin-1-yl)-3-pyridinyloxy; (3-aminoazetidin-1-yl)-3-pyridinyl; (4-morpholin-2-ylmethyl)phenyl; (4-morpholin-2-ylmethyl)phenylamino; (4-piperazin-1-ylphenyl)azetidin-1-yl; (4-piperazin-1-ylphenyl)methylamino; (6-amino-1,4-oxazepan-4-yl)-3-pyridinyl; 2-piperazin-1-ylpyrimidin-5-yloxy; 3-amino-4-fluoro-pyrrolidin-1-yl; 4-morpholin-2-ylphenyl; 4-morpholin-2-ylphenylamino; 4-piperazin-1-ylphenyl; 4-pyridinylpiperazin-1-yl; 5-piperazin-1-yl-2-pyridinyloxy; 5-piperazin-1-yl-3-pyridinyloxy; 6-piperazin-1-yl-3-pyridinyl or 6-piperazin-1-yl-3-pyridinyloxy.

A further embodiment of present invention is (iv) a compound of formula (I), according to any one of (i) to (iii), or a pharmaceutically acceptable salt thereof, wherein R² is methyl.

A further embodiment of present invention is (v) a compound of formula (I) according to any one of (i) to (iv), wherein R³ is (morpholinyl$C_{1-6}$alkyl)phenylamino, (piperazinylphenyl)azetidinyl, morpholinylphenyl, morpholinylphenylamino, piperazinylpyridinyloxy or piperazinylpyrimidinyloxy.

A further embodiment of present invention is (vi) a compound of formula (I), or a pharmaceutically acceptable salt thereof, according to any one of (i) to (v), wherein R³ is (4-morpholin-2-ylmethyl)phenylamino, (4-piperazin-1-ylphenyl)azetidin-1-yl, 4-morpholin-2-ylphenyl, 4-morpholin-2-ylphenylamino, 6-piperazin-1-yl-3-pyridinyloxy or 2-piperazin-1-ylpyrimidin-5-yloxy.

A further embodiment of present invention is (vii) a compound of formula (I), or a pharmaceutically acceptable salt thereof, according to any one of (i) to (vi), wherein R¹ is

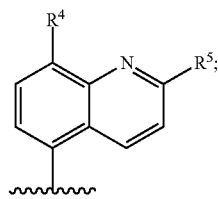

wherein R⁴ is cyano; R⁵ is H or deuterium;

R² is $C_{1-6}$alkyl;

R³ is (morpholinyl$C_{1-6}$alkyl)phenylamino, (piperazinylphenyl)azetidinyl, morpholinylphenyl, morpholinylphenylamino, piperazinylpyridinyloxy or piperazinylpyrimidinyloxy;

or a pharmaceutically acceptable salt thereof.

A further embodiment of present invention is (viii) a compound of formula (I), or a pharmaceutically acceptable salt thereof, according to any one of (i) to (vii), wherein R¹ is

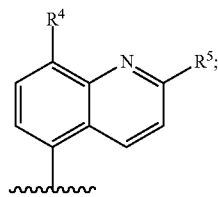

wherein R⁴ is cyano; R⁵ is H or deuterium;

R² is methyl;

R³ is (4-morpholin-2-ylmethyl)phenylamino, (4-piperazin-1-ylphenyl)azetidin-1-yl, 4-morpholin-2-ylphenyl, 4-morpholin-2-ylphenylamino, 6-piperazin-1-yl-3-pyridinyloxy or 2-piperazin-1-ylpyrimidin-5-yloxy;

or a pharmaceutically acceptable salt thereof.

Another embodiment of present invention is a compound of formula (I) selected from the following:

5-[(4R,8R,9aS)-4-methyl-8-[(4-piperazin-1-ylphenyl)methylamino]-1,3,4,6,7,8,9,9a-octahydropyrido[1,2-a]pyrazin-2-yl]quinoline-8-carbonitrile;

5-[(4R,8S,9aS)-4-methyl-8-[(4-piperazin-1-ylphenyl)methylamino]-1,3,4,6,7,8,9,9a-octahydropyrido[1,2-a]pyrazin-2-yl]quinoline-8-carbonitrile;

5-[(4R,8R)-4-methyl-8-(6-piperazin-1-yl-3-pyridyl)-1,3,4,6,7,8,9,9a-octahydropyrido[1,2-a]pyrazin-2-yl]quinoline-8-carbonitrile;

5-[(4R,8R)-4-methyl-8-(4-piperazin-1-ylphenyl)-1,3,4,6,7,8,9,9a-octahydropyrido[1,2-a]pyrazin-2-yl]quinoline-8-carbonitrile;

5-[(4R,8R,9aS)-4-methyl-8-(6-piperazin-1-yl-3-pyridyl)-1,3,4,6,7,8,9,9a-octahydropyrido[1,2-a]pyrazin-2-yl]quinoline-8-carbonitrile;

5-[(4R,8R,9aS)-8-[6-[(3S,4S)-3-amino-4-methoxy-pyrrolidin-1-yl]-3-pyridyl]-4-methyl-1,3,4,6,7,8,9,9a-octahydropyrido[1,2-a]pyrazin-2-yl]quinoline-8-carbonitrile;

5-[(4R,8R,9aS)-8-[6-(3-aminoazetidin-1-yl)-3-pyridyl]-4-methyl-1,3,4,6,7,8,9,9a-octahydropyrido[1,2-a]pyrazin-2-yl]quinoline-8-carbonitrile;

5-[(4R,8R,9aS)-4-methyl-8-[3-(4-piperazin-1-ylphenyl)azetidin-1-yl]-1,3,4,6,7,8,9,9a-octahydropyrido[1,2-a]pyrazin-2-yl]quinoline-8-carbonitrile;

5-[(4R,8S,9aS)-4-methyl-8-[(5-piperazin-1-yl-2-pyridyl)oxy]-1,3,4,6,7,8,9,9a-octahydropyrido[1,2-a]pyrazin-2-yl]quinoline-8-carbonitrile;

5-[(4R,8R,9aS)-8-[6-[(3R,4S)-3-amino-4-methoxy-pyrrolidin-1-yl]-3-pyridyl]-4-methyl-1,3,4,6,7,8,9,9a-octahydropyrido[1,2-a]pyrazin-2-yl]quinoline-8-carbonitrile;

5-[(4R,8R,9aS)-8-[6-[(3S,4R)-3-amino-4-methoxy-pyrrolidin-1-yl]-3-pyridyl]-4-methyl-1,3,4,6,7,8,9,9a-octahydropyrido[1,2-a]pyrazin-2-yl]quinoline-8-carbonitrile;

5-[(4R,8R,9aS)-8-[6-[(3R,4R)-3-amino-4-methoxy-pyrrolidin-1-yl]-3-pyridyl]-4-methyl-1,3,4,6,7,8,9,9a-octahydropyrido[1,2-a]pyrazin-2-yl]quinoline-8-carbonitrile;

5-[(4R,8R,9aR)-4-methyl-8-(6-piperazin-1-yl-3-pyridyl)-1,3,4,6,7,8,9,9a-octahydropyrido[1,2-a]pyrazin-2-yl]quinoline-8-carbonitrile;

5-[(4R,8S,9aS)-4-methyl-8-[(6-piperazin-1-yl-3-pyridyl)oxy]-1,3,4,6,7,8,9,9a-octahydropyrido[1,2-a]pyrazin-2-yl]quinoline-8-carbonitrile;

5-[(4R,8S,9aS)-4-methyl-8-(2-piperazin-1-ylpyrimidin-5-yl)oxy-1,3,4,6,7,8,9,9a-octahydropyrido[1,2-a]pyrazin-2-yl]quinoline-8-carbonitrile;

5-[(4R,8R,9aS)-8-[6-[(3R,4S)-3-amino-4-fluoro-pyrrolidin-1-yl]-3-pyridyl]-4-methyl-1,3,4,6,7,8,9,9a-octahydropyrido[1,2-a]pyrazin-2-yl]quinoline-8-carbonitrile;

5-[(4R,8R,9aS)-4-methyl-8-[4-[(2S)-morpholin-2-yl]anilino]-1,3,4,6,7,8,9,9a-octahydropyrido[1,2-a]pyrazin-2-yl]quinoline-8-carbonitrile;

5-[(4R,8R,9aS)-4-methyl-8-[4-[[(2R)-morpholin-2-yl]methyl]anilino]-1,3,4,6,7,8,9,9a-octahydropyrido[1,2-a]pyrazin-2-yl]quinoline-8-carbonitrile;

5-[(4R,8R,9aS)-4-methyl-8-[4-[[(2R)-morpholin-2-yl]methyl]anilino]-1,3,4,6,7,8,9,9a-octahydropyrido[1,2-a]pyrazin-2-yl]-2-deuterio-quinoline-8-carbonitrile5-[(4R,8R,9aS)-4-methyl-8-[4-[[(2R)-morpholin-2-yl]methyl]anilino]-1,3,4,6,7,8,9,9a-octahydropyrido[1,2-a]pyrazin-2-yl]-2-deuterio-quinoline-8-carbonitrile;

5-[(4R,8R,9aS)-8-[6-[(6S)-6-amino-1,4-oxazepan-4-yl]-3-pyridyl]-4-methyl-1,3,4,6,7,8,9,9a-octahydropyrido[1,2-a]pyrazin-2-yl]quinoline-8-carbonitrile;

5-[(4R,8S,9aS)-4-methyl-8-(4-morpholin-2-ylphenyl)-1,3,4,6,7,8,9,9a-octahydropyrido[1,2-a]pyrazin-2-yl]quinoline-8-carbonitrile;

5-[(4R,8R,9aS)-4-methyl-8-[4-[(2R)-morpholin-2-yl]phenyl]-1,3,4,6,7,8,9,9a-octahydropyrido[1,2-a]pyrazin-2-yl]quinoline-8-carbonitrile;

5-[(4R,8R,9aS)-4-methyl-8-[4-[[(2R)-morpholin-2-yl]methyl]phenyl]-1,3,4,6,7,8,9,9a-octahydropyrido[1,2-a]pyrazin-2-yl]quinoline-8-carbonitrile;

5-[(4R,8S,9aS)-4-methyl-8-[4-(morpholin-2-ylmethyl)phenyl]-1,3,4,6,7,8,9,9a-octahydropyrido[1,2-a]pyrazin-2-yl]quinoline-8-carbonitrile;

5-[(4R,8S,9aS)-8-[[6-[(3R,4S)-3-amino-4-methoxy-pyrrolidin-1-yl]-3-pyridyl]oxy]-4-methyl-1,3,4,6,7,8,9,9a-octahydropyrido[1,2-a]pyrazin-2-yl]quinoline-8-carbonitrile;

5-[(4R,8S,9aS)-4-methyl-8-[(5-piperazin-1-yl-3-pyridyl)oxy]-1,3,4,6,7,8,9,9a-octahydropyrido[1,2-a]pyrazin-2-yl]quinoline-8-carbonitrile;

5-[(4R,8R,9aS)-8-[3-[4-[(3R,4R)-3-amino-4-methoxy-pyrrolidin-1-yl]phenyl]azetidin-1-yl]-4-methyl-1,3,4,6,7,8,9,9a-octahydropyrido[1,2-a]pyrazin-2-yl]quinoline-8-carbonitrile;

5-[(4R,8R,9aS)-8-[3-[4-[(3R,4S)-3-amino-4-methoxy-pyrrolidin-1-yl]phenyl]azetidin-1-yl]-4-methyl-1,3,4,6,7,8,9,9a-octahydropyrido[1,2-a]pyrazin-2-yl]quinoline-8-carbonitrile;

5-[(4R,8R,9aS)-4-methyl-8-[4-[[(2S)-morpholin-2-yl]methyl]anilino]-1,3,4,6,7,8,9,9a-octahydropyrido[1,2-a]pyrazin-2-yl]-2-deuterio-quinoline-8-carbonitrile;

5-[(4R,8R,9aS)-8-[3-[4-[(3R,4S)-3-amino-4-methoxy-pyrrolidin-1-yl]phenyl]azetidin-1-yl]-4-methyl-1,3,4,6,7,8,9,9a-octahydropyrido[1,2-a]pyrazin-2-yl]]-2-deuterio-quinoline-8-carbonitrile; and 5-[(4R,8R,9aS)-4-methyl-8-[4-(4-pyridyl)piperazin-1-yl]-1,3,4,6,7,8,9,9a-octahydropyrido[1,2-a]pyrazin-2-yl]-2-deuterio-quinoline-8-carbonitrile;

or a pharmaceutically acceptable salt thereof.

Synthesis

The compounds of the present invention can be prepared by any conventional means. Suitable processes for synthesizing these compounds as well as their starting materials are provided in the schemes below and in the examples. All substituents, in particular, $R^1$ and $R^2$ are as defined above unless otherwise indicated. Furthermore, and unless explicitly otherwise stated, all reactions, reaction conditions, abbreviations and symbols have the meanings well known to a person of ordinary skill in organic chemistry.

General synthetic routes for preparing the compound of formula (I) and (VI) and (X) and (XV) and (XIX) are shown below:

Scheme 1

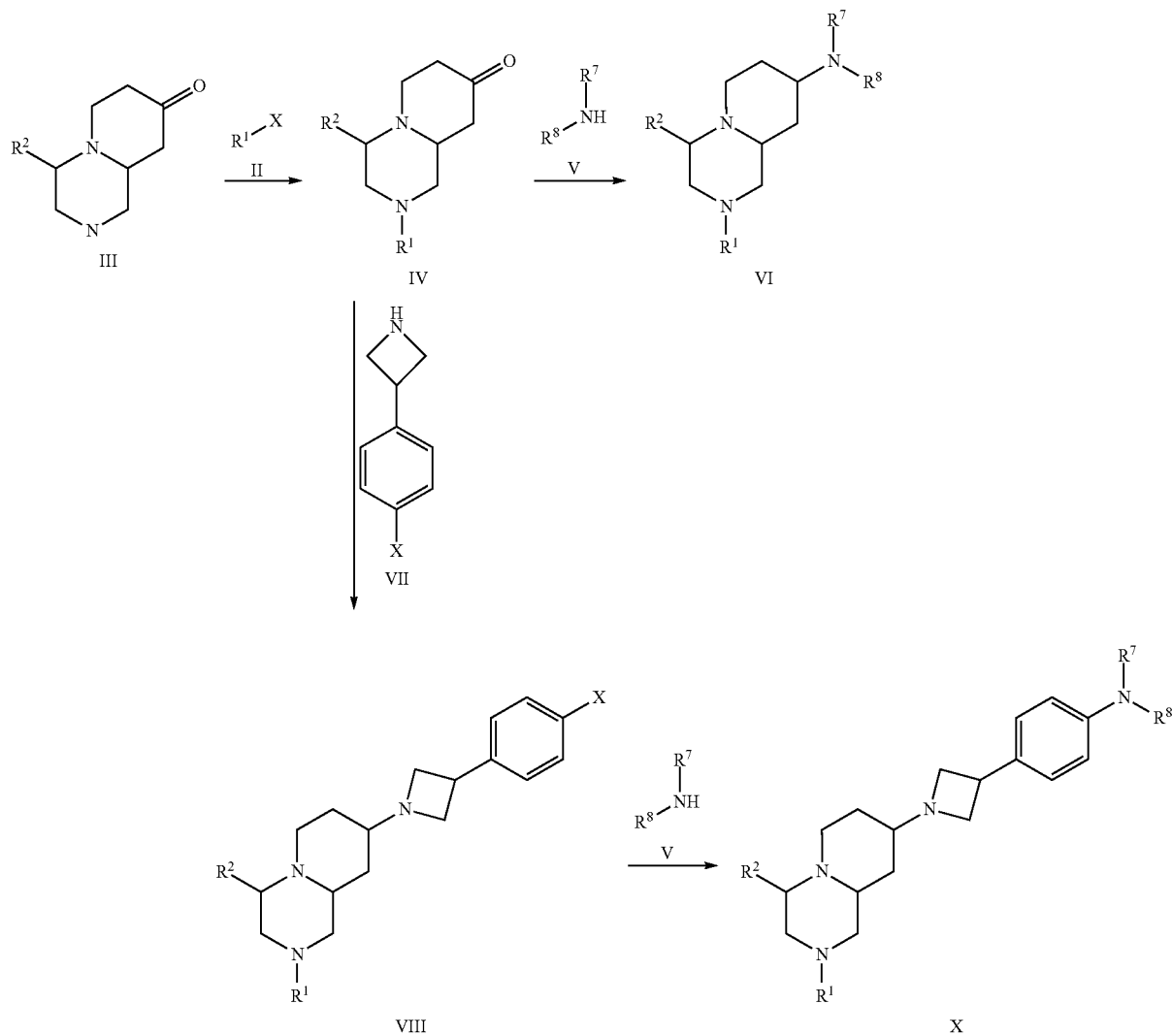

wherein X is halogen; $R^7$ is H; $R^8$ is heterocyclylheteroaryl, heterocyclyl$C_{1-6}$alkylheteroaryl, heterocyclylheteroaryl$C_{1-6}$alkyl, heterocyclyl$C_{1-6}$alkylaryl, heterocyclylaryl$C_{1-6}$alkyl; or $R^7$ and $R^8$ together with the nitrogen they are attached to form a heterocyclyl.

The synthesis of above compounds started from the reaction of bicyclic amine, compound of formula (III), with halide (II) via Buchwald-Hartwig amination reaction in the presence of a catalyst, such as Ruphos Pd-G2, and a base, such as $Cs_2CO_3$, which provides compound of formula (IV) (ref: Acc. Chem. Res. 1998, 31, 805-818; Chem. Rev. 2016, 116, 12564-12649; Topics in Current Chemistry, 2002, 219, 131-209; and references cited therein). Alternatively, compound of formula (IV) can also be obtained via nucleophilic substitution between halide (II) and compound of formula (III) in the presence of a base, such as DIPEA, $NaHCO_3$ and $K_2CO_3$. Compound of formula (VI) and (VIII) can be obtained from compound of formula (IV) via Borsch reductive amination with amines of compound of formula (V) and (VII) respectively in the presence of reducing agent, such as $NaCNBH_3$. The coupling of compound of formula (VIII) with amine (V) can be achieved under Buchwald-Hartwig amination conditions (ref: Acc. Chem. Res. 1998, 31, 805-818; Chem. Rev. 2016, 116, 12564-12649; Topics in Current Chemistry, 2002, 219, 131-209; and references cited therein) with a catalyst, such as tBuXPhos Pd G3, RuPhos Pd G2, BrettPhos Pd G3, XPhos Pd G3$Pd_2(dba)_3$/BINAP and $Pd_2(dba)_3$/XantPhos and a base, such as $Cs_2CO_3$ or t-BuONa, to provide compound of formula (X).

Scheme 2

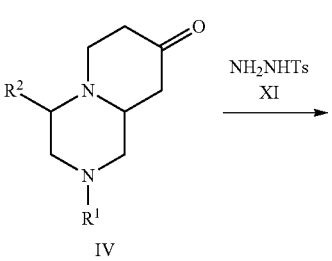

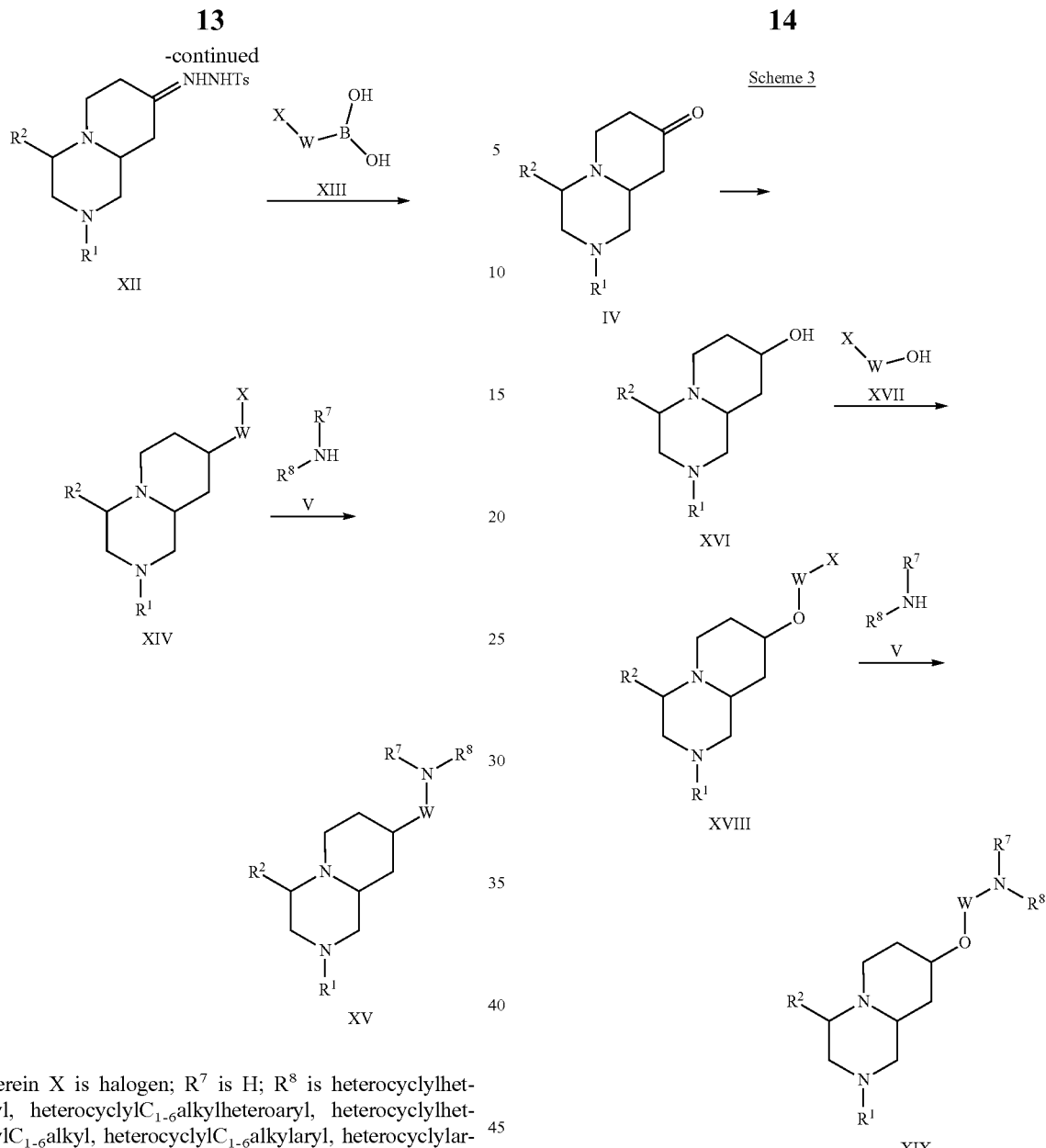

Scheme 3 wherein X is halogen; $R^7$ is H; $R^8$ is heterocyclylheteroaryl, heterocyclyl$C_{1-6}$alkylheteroaryl, heterocyclylheteroaryl$C_{1-6}$alkyl, heterocyclyl$C_{1-6}$alkylaryl, heterocyclylaryl$C_{1-6}$alkyl; or $R^7$ and $R^8$ together with the nitrogen they are attached to form a heterocyclyl; W is heteroaryl or aryl.

Compound of formula (IV) can react with tosylhydrazide (XI) to afford compound of formula (XII). Compound of formula (XIV) can be obtained via reductive coupling of compound of formula (XII) with boronic acids formula (XIII) in the presence of a base, such as $Cs_2CO_3$, DIPEA, $NaHCO_3$ and $K_2CO_3$ (ref: Chem. Eur. J. 2016, 22, 6253-6257, J. Org. Chem. 2014, 79, 328-338). The coupling of amine (V) with compound of formula (XIV) can be achieved under Buchwald-Hartwig amination conditions (ref: *Acc. Chem. Res.* 1998, 31, 805-818; *Chem. Rev.* 2016, 116, 12564-12649; *Topics in Current Chemistry*, 2002, 219, 131-209; and references cited therein) with a catalyst, such as tBuXPhos Pd G3, RuPhos Pd G2, BrettPhos Pd G3, XPhos Pd G3 $Pd_2(dba)_3$/BINAP and $Pd_2(dba)_3$/XantPhos and a base, such as $Cs_2CO_3$ or t-BuONa, to provide compound of formula (XV).

Synthetic routes for preparing the compound of formula XIX are shown in scheme 3.

wherein X is halogen; $R^7$ is H; $R^8$ is heterocyclylheteroaryl, heterocyclyl$C_{1-6}$alkylhetero aryl, heterocyclylheteroaryl$C_{1-6}$alkyl, heterocyclyl$C_{1-6}$alkylaryl, heterocyclylaryl$C_{1-6}$alkyl; or $R^7$ and $R^8$ together with the nitrogen they are attached to form a heterocyclyl; W is heteroaryl or aryl.

Reduction of compound of formula (IV) in the presence of reducing reagent, such as $NaBH_4$, gives compound of formula (XVI), which can be transformed into compound of formula (XVIII) via Mitsunobu reaction in the presence of diethyl azodicarboxylate (DEAD) or diisopropyl azodicarboxylate (DIAD) and $Ph_3P$. The coupling of amine (V) with compound of formula (XVIII) can be achieved under Buchwald-Hartwig amination conditions (ref: *Acc. Chem. Res.* 1998, 31, 805-818; *Chem. Rev.* 2016, 116, 12564-12649; *Topics in Current Chemistry*, 2002, 219, 131-209; and references cited therein) with a catalyst, such as tBuXPhos Pd G3, RuPhos Pd G2, BrettPhos Pd G3, XPhos Pd G3 $Pd_2(dba)_3$/BINAP and $Pd_2(dba)_3$/XantPhos and a base, such as $Cs_2CO_3$ or t-BuONa, to provide compound of formula (XIX).

Compounds of this invention can be obtained as mixtures of diastereomers or enantiomers, which can be separated by methods well known in the art, e.g. (chiral) HPLC or SFC.

This invention also relates to a process for the preparation of a compound of formula (I) comprising any one of the following steps:

a) Buchwald-Hartwig amination reaction between compound of formula (VIII),

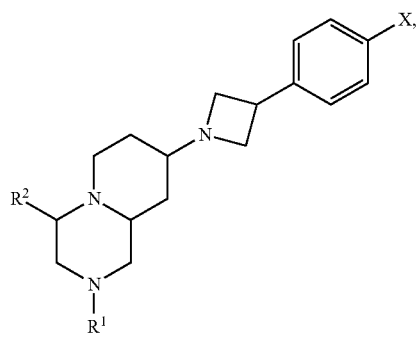

(VIII)

and amine (V),

(V)

b) reductive amination of compound of formula (IV),

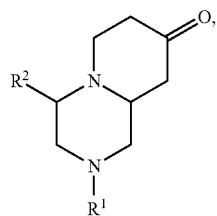

(IV)

with amine (V),

(V)

c) Buchwald-Hartwig amination reaction between compound of formula (XIV),

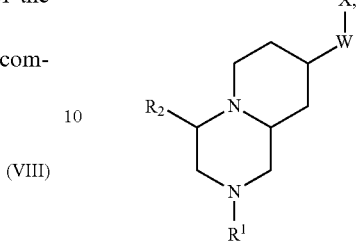

(XIV)

and amine (V),

(V)

d) Buchwald-Hartwig amination reaction between compound of formula (XVIII),

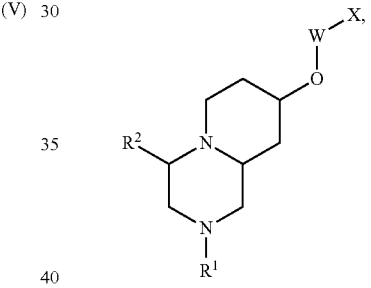

(XVIII)

and amine (V),

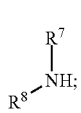

(V)

wherein X is halogen; $R^7$ is H; $R^8$ is heterocyclylheteroaryl, heterocyclyl$C_{1-6}$alkylheteroaryl, heterocyclylheteroaryl$C_{1-6}$alkyl, heterocyclyl$C_{1-6}$alkylaryl, heterocyclylaryl$C_{1-6}$alkyl; or $R^7$ and $R^8$ together with the nitrogen they are attached to form a heterocyclyl; W is heteroaryl or aryl.

A compound of formula (I) when manufactured according to the above process is also an object of the invention.

Indications and Methods of Treatment

The present invention provides compounds that can be used as TLR7 and/or TLR8 and/or TLR9 antagonist, which inhibits pathway activation through TLR7 and/or TLR8 and/or TLR9 as well as respective downstream biological events including, but not limited to, innate and adaptive immune responses mediated through the production of all types of cytokines and all forms of auto-antibodies. Accordingly, the compounds of the invention are useful for blocking TLR7 and/or TLR8 and/or TLR9 in all types of cells that express such receptor(s) including, but not limited to, plasmacytoid dendritic cell, B cell, T cell, macrophage, monocyte, neutrophil, keratinocyte, epithelial cell. As such, the compounds can be used as a therapeutic or prophylactic agent for systemic lupus erythematosus and lupus nephritis.

The present invention provides methods for treatment or prophylaxis of systemic lupus erythematosus and lupus nephritis in a patient in need thereof.

Another embodiment includes a method of treating or preventing systemic lupus erythematosus and lupus nephritis in a mammal in need of such treatment, wherein the method comprises administering to said mammal a therapeutically effective amount of a compound of formula (I), a stereoisomer, tautomer, prodrug or pharmaceutically acceptable salt thereof.

EXAMPLES

The invention will be more fully understood by reference to the following examples. They should not, however, be construed as limiting the scope of the invention.

Abbreviations

The invention will be more fully understood by reference to the following examples. They should not, however, be construed as limiting the scope of the invention.

Abbreviations used herein are as follows:
ACN: acetonitrile
DCM: dichloromethane
DCE: dichloroethane
DIAD diisopropyl azodicarboxylate
DIPEA or DIEA: N,N-diisopropylethylamine
DMF: N,N-Dimethylformamide
EA or EtOAc: ethyl acetate
FA: formic acid
$IC_{50}$: half inhibition concentration
IPA: isopropanol
MS: mass spectrometry
$PPh_3$: triphenylphosphine
$Pd(PPh_3)_4$ tetrakis(triphenylphosphine)palladium
Pd/C palladium on Carbon
prep-HPLC: preparative high performance liquid chromatography
prep-TLC: preparative thin layer chromatography
RuPhos Pd G2: chloro(2-dicyclohexylphosphino-2',6'-di-isopropoxy-1,1'-biphenyl)[2-(2'-amino-1,1'-biphenyl)]palladium(II) 2nd generation
SFC: supercritical fluid chromatography
TEA: trimethylamine
TFA: trifluoroacetic acid
THF: tetrahydrofuran
v/v volume ratio

General Experimental Conditions

Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 µm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 µm, OBDTM 30×100 mm) column, SunFire™ Prep-C18 (5 µm, OBD™ 30×100 mm) column, Phenomenex Synergi-C18 (10 µm, 25×150 mm) or Phenomenex Gemini-C18 (10 µm, 25×150 mm). Waters AutoP purification System (Sample Manager 2767, Pump 2525, Detector: Micromass ZQ and UV 2487, solvent system: acetonitrile and 0.1% ammonium hydroxide in water; acetonitrile and 0.1% FA in water or acetonitrile and 0.1% TFA in water). Or Gilson-281 purification System (Pump 322, Detector: UV 156, solvent system: acetonitrile and 0.05% ammonium hydroxide in water; acetonitrile and 0.225% FA in water; acetonitrile and 0.05% HCl in water; acetonitrile and 0.075% TFA in water; or acetonitrile and water).

For SFC chiral separation, intermediates were separated by chiral column (Daicel chiralpak IC, 5 µm, 30×250 mm), AS (10 µm, 30×250 mm) or AD (10 µm, 30×250 mm) using Mettler Toledo Multigram III system SFC, Waters 80Q preparative SFC or Thar 80 preparative SFC, solvent system: $CO_2$ and IPA (0.5% TEA in IPA) or $CO_2$ and MeOH (0.1% $NH_3 \cdot H_2O$ in MeOH), back pressure 100bar, detection UV@ 254 or 220 nm.

LC/MS spectra of compounds were obtained using a LC/MS (Waters™ Alliance 2795-Micromass ZQ, Shimadzu Alliance 2020-Micromass ZQ or Agilent Alliance 6110-Micromass ZQ), LC/MS conditions were as follows (running time 3 or 1.5 mins):

Acidic condition I: A: 0.1% TFA in $H_2O$; B: 0.1% TFA in acetonitrile;

Acidic condition II: A: 0.0375% TFA in $H_2O$; B: 0.01875% TFA in acetonitrile;

Basic condition I: A: 0.1% $NH_3 \cdot H_2O$ in $H_2O$; B: acetonitrile;

Basic condition II: A: 0.025% $NH_3 \cdot H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(MH)^+$.

NMR Spectra were obtained using Bruker Avance 400 MHz.

The microwave assisted reactions were carried out in a Biotage Initiator Sixty microwave synthesizer. All reactions involving air-sensitive reagents were performed under an argon or nitrogen atmosphere. Reagents were used as received from commercial suppliers without further purification unless otherwise noted.

Preparative Examples

The following examples are intended to illustrate the meaning of the present invention but should by no means represent a limitation within the meaning of the present invention:

Intermediate A1

5-Fluoroquinoline-8-carbonitrile

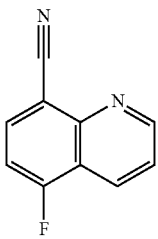

The titled compound was synthesized according to the following scheme:

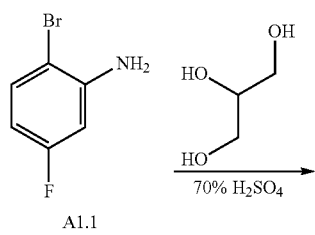

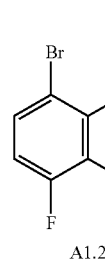

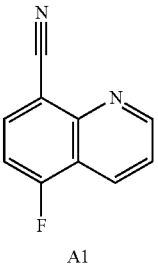

Step 1: preparation of 8-bromo-5-fluoro-quinoline (compound A1.2)

In a 100 mL pear-shaped flask, 2-bromo-5-fluoroaniline (compound A1.1, 2.0 g, 10.5 mmol), propane-1,2,3-triol (969 mg, 10.5 mmol) and sodium 3-nitrobenzenesulfonate (2.4 g, 10.5 mmol) were combined with 70% $H_2SO_4$ (20 mL) to afford a dark brown solution, which was heated to 150° C. and stirred for 3 hrs. After being cooled to room temperature, the reaction mixture was poured into ice-water, and neutralized with sodium hydroxide solution. The resultant mixture was filtered. The filter cake was dissolved in EtOAc and filtered. The resultant filtrate was concentrated in vacuo. The crude material was purified by flash chromatography (silica gel, 40 g, 0% to 30% EtOAc in PE) to afford compound A1.2 (2.0 g, 84% yield). MS: calc'd 226 and 228 ($MH^+$), measured 226 and 228 ($MH^+$).

Step 2: preparation of 5-fluoroquinoline-8-carbonitrile (Intermediate A1)

To a solution of 8-bromo-5-fluoroquinoline (compound A1.2, 4.9 g, 21.7 mmol) in DMF (30 mL) was added dicyanozinc (5.0 g, 43.4 mmol) and RuPhos Pd G2 (CAS: 1375325-68-0, Sigma-Aldrich, Catalog #753246, 842 mg, 1.1 mmol). The reaction mixture was stirred at 100° C. for 3 hrs, then cooled to room temperature. The reaction mixture was filtered and the filtrate was diluted with water (50 mL), then extracted with EA (80 mL) for three times. The combined organic layer was washed with brine, dried over $Na_2SO_4$, filtered and concentrated in vacuo. The residue was purified by flash chromatography (silica gel, 40 g, 0% to 70% EtOAc in PE) to afford Intermediate A1 (3.0 g, 80% yield). MS: calc'd 173 ($MH^+$), measured 173 ($MH^+$). $^1H$ NMR (400 MHz, METHANOL-$d_4$) δ 9.11 (dd, J=4.28, 1.71 Hz, 1H), 8.64 (dd, J=8.56, 1.71 Hz, 1H), 8.29 (dd, J=8.19, 5.62 Hz, 1H), 7.76 (dd, J=8.56, 4.28 Hz, 1H), 7.49 (dd, J=9.35, 8.25 Hz, 1H).

Intermediate A2

2-Deuterio-5-fluoro-quinoline-8-carbonitrile

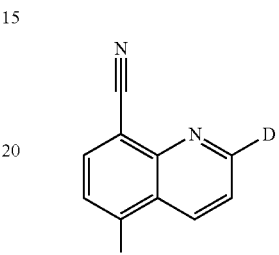

The titled compound was synthesized according to the following scheme:

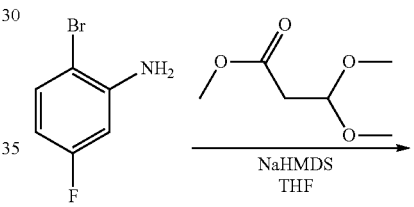

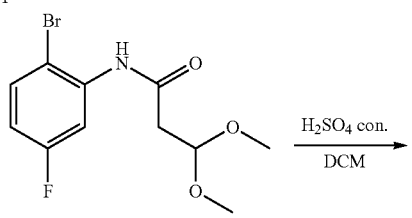

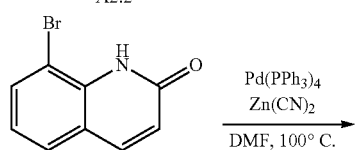

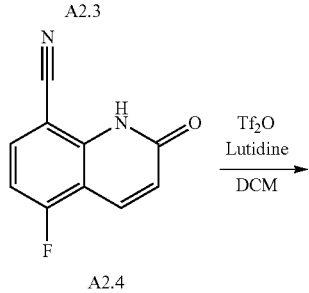

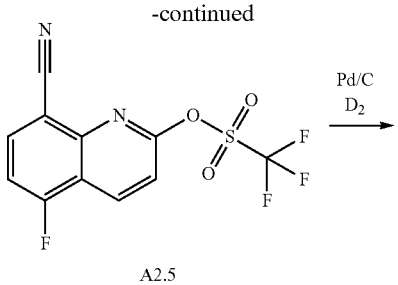

A2.5

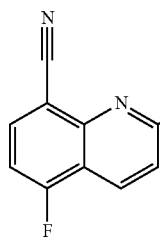

A2

Step 1: preparation of N-(2-bromo-5-fluoro-phenyl)-3,3-dimethoxy-propanamide (compound A2.2)

To a solution of 2-bromo-5-fluoroaniline (compound A2.1, 50 g, 263 mmol) and methyl 3,3-dimethoxypropionate, (45 mL, 316 mmol) in THF (150 mL) was added NaHMDS in THF (394 mL, 394 mmol) dropwise at 0° C. The mixture was stirred at the temperature for 10 minutes, and then it was warmed up to 15° C. and stirred for 18 hrs. The reaction was quenched with sat. aqueous solution of NH$_4$Cl and concentrated to about 300 mL. The solution was diluted with water and extracted with EtOAc. The organic layer was dried over Na$_2$SO$_4$ and concentrated to afford compound A2.2 (100 g, 90% yield). MS: calc'd 306 (MH$^+$), measured 306 (MH$^+$).

Step 2: preparation of 8-bromo-5-fluoro-1H-quinolin-2-one (compound A2.3)

A solution of N-(2-bromo-5-fluoro-phenyl)-3,3-dimethoxy-propanamide (compound A2.2, 100 g, 238 mmol) in DCM (500 mL) was added to concentrated sulfuric acid (300 mL) at 0° C. The mixture was stirred at 15° C. for 2 hrs. The mixture was poured slowly into 2000 mL ice-water, and a yellow precipitate appeared. The mixture was filtered, and the wet-cake was washed with 500 mL water, 200 mL isopropyl alcohol and 300 mL PE. The solid was dried under vacuum to afford compound A2.3 (50 g, 86.5% yield). MS: calc'd 242 (MH$^+$), measured 242 (MH$^+$).

Step 3: preparation of 5-fluoro-2-oxo-1H-quinoline-8-carbonitrile (compound A2.4)

A solution of 8-bromo-5-fluoro-1H-quinolin-2-one (compound A2.3, 50 g, 206 mmol), zinc cyanide (4820 mg, 412 mmol), Pd(PPh$_3$)$_4$ (2428 mg, 21 mmol) in DMF was stirred at 120° C. for 5 hrs. The reaction mixture was diluted with water and extracted with DCM. The organic layer was dried and concentrated to give the crude product, which was purified by flash column to afford compound A2.4 (29 g, 74.5% yield). MS: calc'd 189 (MH$^+$), measured 189 (MH$^+$).

Step 4: preparation of (8-cyano-5-fluoro-2-quinolyl) trifluoromethanesulfonate (compound A2.5)

To a solution of 5-fluoro-2-oxo-1H-quinoline-8-carbonitrile (compound A2.4, 17 g, 90 mmol) and 2,6-dimethylpyridine (39 g, 361 mmol) in DCM was added trifluoromethanesulfonic anhydride (51 g, 181 mmol) dropwise at 0° C. The mixture was stirred at 0° C. for 1 hr, and then the reaction was diluted with water, extracted with DCM. The organic layer was dried and concentrated. The residue was purified by flash column to give compound A2.5 (23.0 g, 80% yield). MS: calc'd 321 (MH$^+$), measured 321 (MH$^+$).

Step 5: preparation of 2-deuterio-5-fluoro-quinoline-8-carbonitrile (Intermediate A2)

To a solution of (8-cyano-5-fluoro-2-quinolyl) trifluoromethanesulfonate (compound A2.5, 23 g, 72 mmol) in THF (230 mL) and deuterium oxide (100 mL) was added potassium carbonate (20 g, 144 mmol) and Pd/C (6 g). The mixture was stirred at 40° C. for 5 hrs under deuterium atmosphere (balloon). The mixture was filtered, and the filtrate was concentrated and purified by flash column to afford Intermediate A2 (11 g, 87.8% yield) which was used directly for the next step without further purification. MS: calc'd 174 (MH$^+$), measured 174 (MH$^+$).

Intermediate B (4R)-4-methyloctahydro-8H-pyrido[1,2-a]pyrazin-8-one 2,2,2-trifluoroacetate

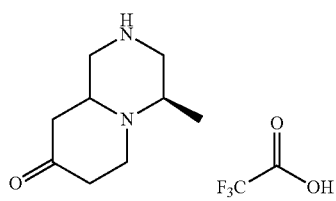

The titled compound was synthesized according to the following scheme:

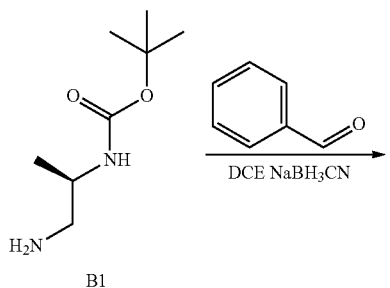

B1

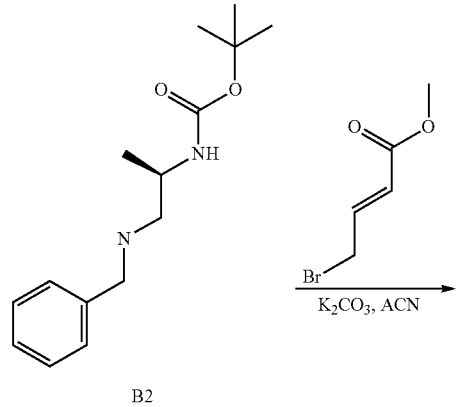

B2

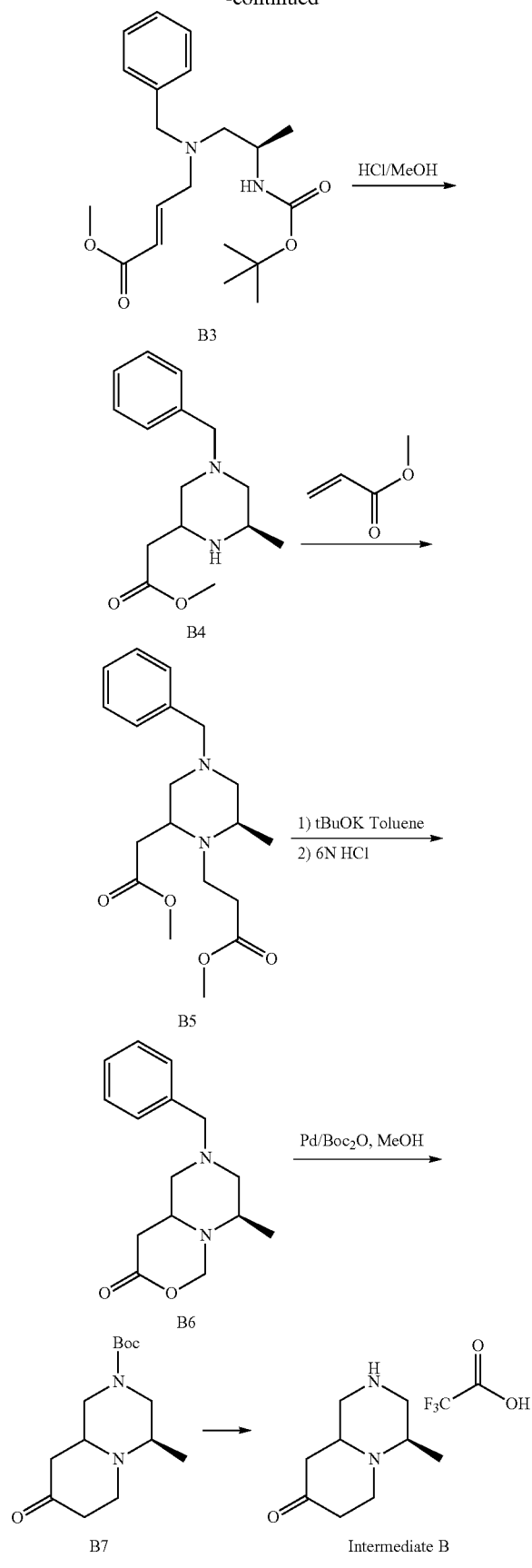

Step 1: preparation of tert-butyl N-[(1R)-2-(benzylamino)-1-methyl-ethyl]carbamate (compound B2)

To a solution of tert-butyl N-[(1R)-2-amino-1-methyl-ethyl]carbamate (compound B1, 135.0 g, 774.8 mmol) in DCE (3.0 L) was added benzaldehyde (71.0 mL, 695.8 mmol). The resultant mixture was stirred at room temperature for 2 hrs. Sodium triacetoxyborohydride (405.0 g, 1.9 mol) was added to the above solution. After being stirred at room temperature overnight, the reaction mixture was neutralized with sat. $Na_2CO_3$ (aq) to pH about 8, diluted with water (1.0 L), and extracted with DCM (1.0 L) twice. The combined organic layer was washed brine (500 mL), dried over $Na_2SO_4$ and concentrated in vacuo. The residue was purified by silica gel chromatography to afford compound B2 (163.6 g, 80% yield). MS: calc'd 265 ($MH^+$), measured 265 ($MH^+$).

Step 2: preparation of methyl (E)-4-[benzyl-[(2R)-2-(tert-butoxycarbonylamino)-propyl]-amino]but-2-enoate (compound B3)

To a solution of tert-butyl N-[(1R)-2-(benzylamino)-1-methyl-ethyl]carbamate (compound B2, 185.0 g, 699.8 mmol) in acetone (2.0 L) was added methyl 4-bromocrotonate (135.0 g, 754.2 mmol) and potassium carbonate (290.0 g, 2.1 mol). After being stirred at room temperature overnight, the mixture was filtered through celite and the filtrate was concentrated. The residue was purified by silica gel chromatography to afford compound B3 (146.0 g, 57.6% yield). MS: calc'd 363 ($MH^+$), measured 363 ($MH^+$).

Step 3: preparation of methyl 2-[(6R)-4-benzyl-6-methyl-piperazin-2-yl]acetate (Compound B4)

The mixture of methyl (E)-4-[benzyl-[(2R)-2-(tert-butoxycarbonylamino)propyl]amino]but-2-enoate (compound B3, 132.0 g, 364.2 mmol) and HCl/methanol (1N, 1.0 L) was heated to reflux for 2 hrs. The reaction mixture was cooled to room temperature and concentrated in vacuo. The residue was neutralized with sat. $K_2CO_3$ (aq) to pH about 10, diluted with water (1.0 L), and extracted with DCM (1.0 L) for three times. The combined organic layer was washed with brine (1000 mL) twice, dried over $Na_2SO_4$ and concentrated in vacuo. The residue was purified by silica gel chromatography to afford compound B4 (90.0 g, 94.0% yield). MS: calc'd 263 ($MH^+$), measured 263 ($MH^+$).

Step 4: preparation of methyl 3((6R)-4-benzyl-2-(2-methoxy-2-oxoethyl)-6-methylpiperazin-1-yl)propanoate (Compound B5)

A solution of methyl 2-((6R)-4-benzyl-6-methylpiperazin-2-yl)acetate (Compound B4, 50 g, 191 mmol,) and methyl acrylate (49.2 g, 51.5 mL, 572 mmol) was heated to 100° C. for 12 hrs. Then the reaction mixture was concentrated and purified by silica gel chromatography (DCM/MeOH 1% to 20%) to afford compound B5 (12.7 g, 19.1% yield) as yellow oil. MS: calc'd 349 ($MH^+$), measured 349 ($MH^+$).

Step 5: preparation of (4R)-2-benzyl-4-methyloctahydro-8H-pyrido[1,2-a]pyrazin-8-one (Compound B6)

To a stirred and cooled (ice-water, 0° C.) suspension of potassium tert-butoxide (8.18 g, 72.9 mmol) in toluene (40 mL) was added slowly a solution of methyl 3-((6R)-4-benzyl-2-(2-methoxy-2-oxoethyl)-6-methylpiperazin-1-yl)propanoate (Compound B5, 12.7 g, 36.4 mmol) in toluene (5 mL). The mixture was stirred at 0° C. for 2 hrs. And then the mixture was extracted with 6N HCl (5 mL) three times. The water layer was stirred at 100° C. for 3 hrs, which was then re-cooled to 0° C., neutralized with $K_2CO_3$ and extracted with EA (100 mL) three times. The organic layers were combined, washed with sat NaCl (20 mL) twice, dried over $Na_2SO_4$ and concentrated in vacuo. The crude material was purified by flash chromatography (silica gel, 80 g, 20% to 80% EtOAc in PE) to afford Compound B6 (6.6 g, 70.4% yield) as light yellow oil. MS: calc'd 259 (MH$^+$), measured 259 (MH$^+$).

Step 6: preparation of tert-butyl (4R)-4-methyl-8-oxooctahydro-2H-pyrido[1,2-a]pyrazine-2-carboxylate (Compound B7)

A solution of (4R)-2-benzyl-4-methyloctahydro-8H-pyrido[1,2-a]pyrazin-8-one (Compound B6, 6.53 g, 25.3 mmol), boc-Anhydride (11 g, 11.7 mL, 50.5 mmol) and Pd-C (700 mg, 6.58 mmol) in MeOH (30 mL) was stirred at room temperature for 3 hrs under H2 atmosphere. Then filtered and the filtrate was concentrated. The resulting residue was purified by silica gel chromatography (DCM/MeOH 2% to 10%) to afford Compound B7 (6.6 g, 97% yield) as a white solid. MS: calc'd 269 (MH$^+$), measured 269 (MH$^+$).

Step 7: preparation of (4R)-4-methyloctahydro-8H-pyrido[1,2-a]pyrazin-8-one 2,2,2-trifluoroacetate (Intermediate B)

To a solution of tert-butyl (4R)-4-methyl-8-oxooctahydro-2H-pyrido[1,2-a]pyrazine-2-carboxylate (Compound B7, 6.6 g, 24.6 mmol) in DCM (20 mL) was added 2,2,2-trifluoroacetic acid (2.8 g, 20 mL) at 0° C. The reaction mixture was stirred at rt for 12 hrs, then concentrated to afford Intermediate B (6.8 g, 98% yield) as light yellow oil. MS: calc'd 169 (MH$^+$), measured 169 (MH$^+$).

Intermediate C1

5-((4R,9aS)-4-methyl-8-oxooctahydro-2H-pyrido[1,2-a]pyrazin-2-yl)quinoline-8-carbonitrile (Intermediate C1)

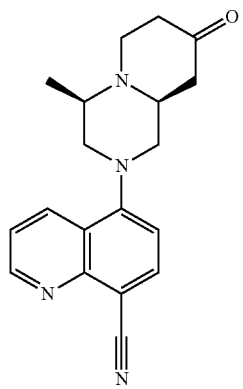 [SMILES: C[C@@H]1CN(c2ccc(C#N)c3ncccc23)C[C@@H]2CC(=O)CCN21]

The titled compound was synthesized according to the following scheme:

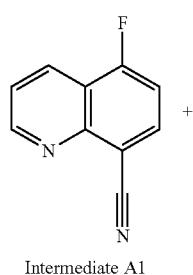

Intermediate A1

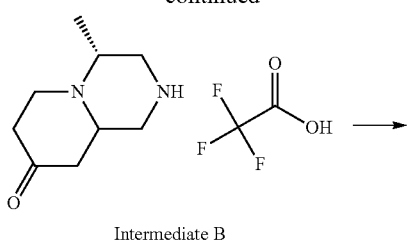

Intermediate B

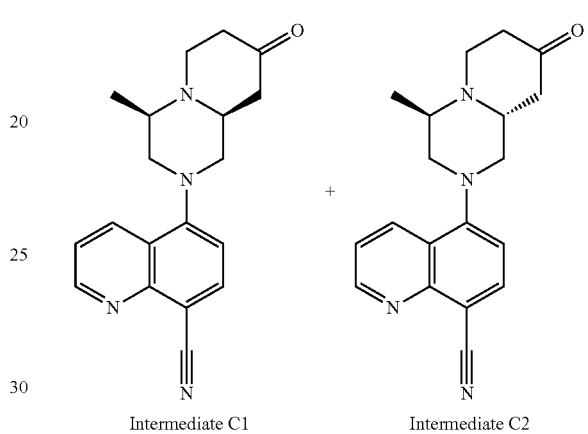

Intermediate C1         Intermediate C2

Step 1: preparation of (4R,8aS)-2-benzyl-4-methyl-3,4,6,7,8,8a-hexahydro-1H-pyrrolo[1,2-a]pyrazin-7-ol (Intermediate C1)

To a solution of DIPEA (9.34 g, 12.6 mL, 72.3 mmol) in DMSO (10 mL) was added 5-fluoroquinoline-8-carbonitrile (Intermediate A1, 4.15 g, 24.1 mmol) and (4R)-4-methyl-octahydro-8H-pyrido[1,2-a]pyrazin-8-one 2,2,2-trifluoroacetate (Intermediate B, 6.8 g, 24.1 mmol). After being stirred at 120° C. for 3 hrs, the mixture was cooled to room temperature, quenched with water (10 mL), extracted with EA twice. The combined organic layer was washed with brine, dried over Na$_2$SO$_4$, filtered and concentrated. The residue was purified by flash chromatography (silica gel, 20% to 80% PE in EtOAc) to afford 5-((4R,9aS)-4-methyl-8-oxooctahydro-2H-pyrido[1,2-a]pyrazin-2-yl)quinoline-8-carbonitrile (Intermediate C1, 2 g, 25.9% yield) as a yellow solid and 5-((4R,9aR)-4-methyl-8-oxooctahydro-2H-pyrido[1,2-a]pyrazin-2-yl)quinoline-8-carbonitrile (Intermediate C2, 400 mg, 5.18% yield) as a yellow solid. The stereochemistry of Intermediate C1 and C2 were confirmed by NOESY.

Intermediate C1: MS: calc'd 321 (MH$^+$), measured 321 (MH$^+$). $^1$H NMR (DMSO-d6, 400 MHz) δ 9.04 (dd, J=1.6, 4.2 Hz, 1H), 8.53 (dd J=1.7, 8.6 Hz, 1H,), 8.24 (d, J=8.1 Hz, 1H), 7.67 (dd, J=4.3, 8.6 Hz, 1H), 7.21 (d, J=8.1 Hz, 1H), 3.5-3.6 (m, 1H), 3.3-3.4 (m, 2H), 2.7-2.9 (m, 3H), 2.5-2.7 (m, 2H), 2.1-2.4 (m, 4H), 1.1-1.2 (m, 3H).

Intermediate C2: MS: calc'd 321 (MH+), measured 321 (Mtl+). ¹H NMR (DMSO-d6, 400 MHz) δ 9.05 (dd, J=1.7, 4.2 Hz, 1H), 8.60 (dd, J=1.6, 8.6 Hz, 1H), 8.25 (d, J=8.1 Hz, 1H), 7.70 (dd, J=4.2, 8.6 Hz, 1H), 7.23 (d, J=8.1 Hz, 1H), 3.4-3.5 (m, 1H), 3.28 (br dd, J=2.7, 11.5 Hz, 2H), 3.20 (br dd, J=5.5, 11.6 Hz, 1H), 3.06 (br d, J=6.5 Hz, 1H), 2.7-2.9 (m, 2H), 2.6-2.7 (m, 1H), 2.65 (dt, J=6.1, 13.5 Hz, 2H), 2.23 (td, J=2.6, 14.2 Hz, 1H), 2.13 (br d, 1H, J=13.7 Hz), 1.1-1.2 (m, 4H).

Intermediate D1

2-deuterio-5-[(4R)-4-methyl-8-oxo-3,4,6,7,9,9a-hexahydro-1H-pyrido[1,2-a]pyrazin-2-yl]quinoline-8-carbonitrile (Intermediate D1)

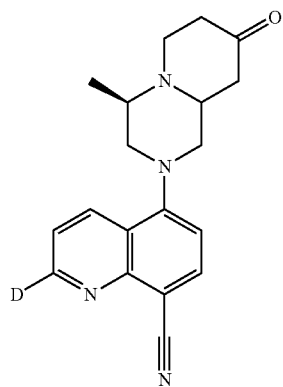 [SMILES: [2H]c1ccc2c(N3CC4CC(=O)CCN4[C@H](C)C3)ccc(C#N)c2n1]

The titled compound was synthesized according to the following scheme:

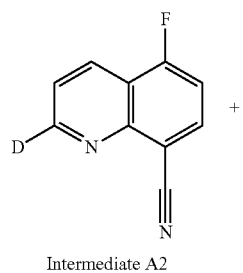

Intermediate A2

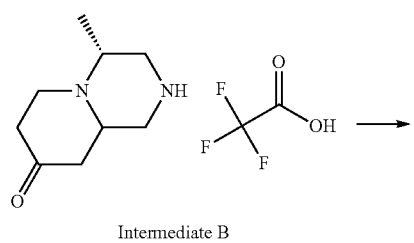

Intermediate B

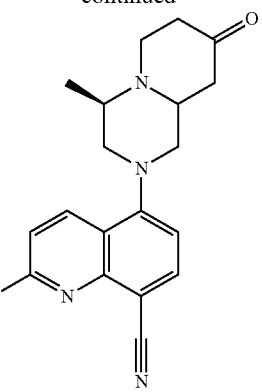

Intermediate D1

Step 1: preparation of 2-deuterio-5-[(4R)-4-methyl-8-oxo-3,4,6,7,9,9a-hexahydro-1H-pyrido[1,2-a]pyrazin-2-yl]quinoline-8-carbonitrile (Intermediate D1)

To a solution of DIPEA (9.34 g, 12.6 mL, 72.3 mmol) in DMSO (10 mL) was added 2-deuterio-5-fluoro-quinoline-8-carbonitrile (Intermediate A2, 300 mg, 1.73 mmol) and (4R)-4-methyloctahydro-8H-pyrido[1,2-a]pyrazin-8-one 2,2,2-trifluoroacetate (Intermediate B, 537 mg, 1.90 mmol). After being stirred at 120° C. for 3 hrs, the mixture was cooled to room temperature, quenched with water (10 mL), extracted with EA twice. The combined organic layers was washed with brine, dried over Na$_2$SO$_4$, filtered and concentrated. The residue was purified by flash chromatography (silica gel, 20% to 80% PE in EtOAc) to afford 2-deuterio-5-[(4R)-4-methyl-8-oxo-3,4,6,7,9,9a-hexahydro-1H-pyrido[1,2-a]pyrazin-2-yl]quinoline-8-carbonitrile (Intermediate D1, 500 mg) as a yellow solid. MS: calc'd 322 (MH+), measured 322 (MH+).

Example 1 & 17

5-[(4R,8R,9aS)-4-methyl-8-[(4-piperazin-1-ylphenyl)methylamino]-1,3,4,6,7,8,9,9a-octahydropyrido[1,2-a]pyrazin-2-yl]quinoline-8-carbonitrile (Example 1)

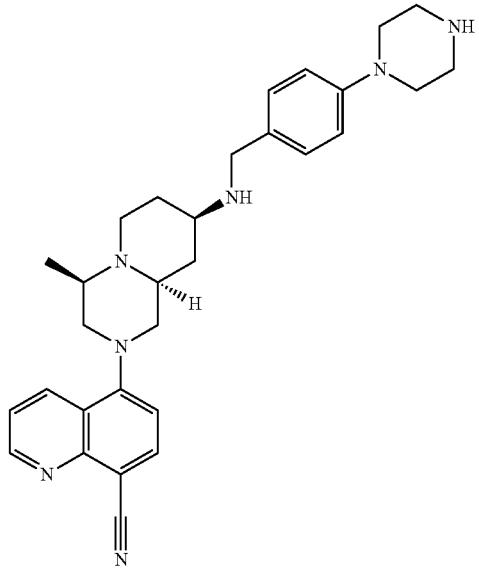 [SMILES: C[C@@H]1CN(c2ccc(C#N)c3ncccc23)C[C@@H]2C[C@H](NCc3ccc(N4CCNCC4)cc3)CCN21]

5-[(4R,8S,9aS)-4-methyl-8-[(4-piperazin-1-ylphenyl)methylamino]-1,3,4,6,7,8,9,9a-octahydropyrido[1,2-a]pyrazin-2-yl]quinoline-8-carbonitrile (Example 17)
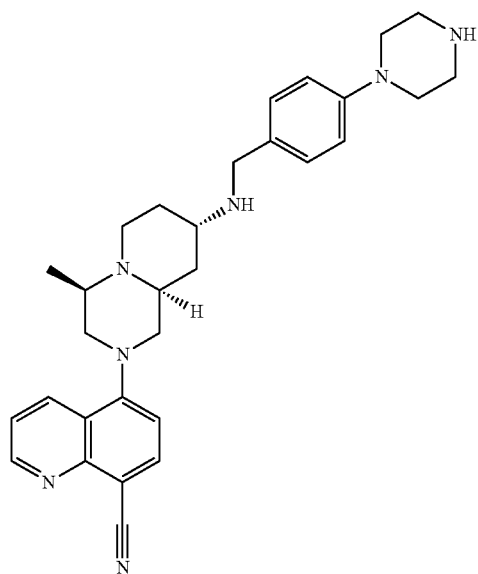 [SMILES: C[C@@H]1CN(c2ccc(C#N)c3ncccc23)C[C@@H]2C[C@@H](NCc3ccc(N4CCNCC4)cc3)CCN21]
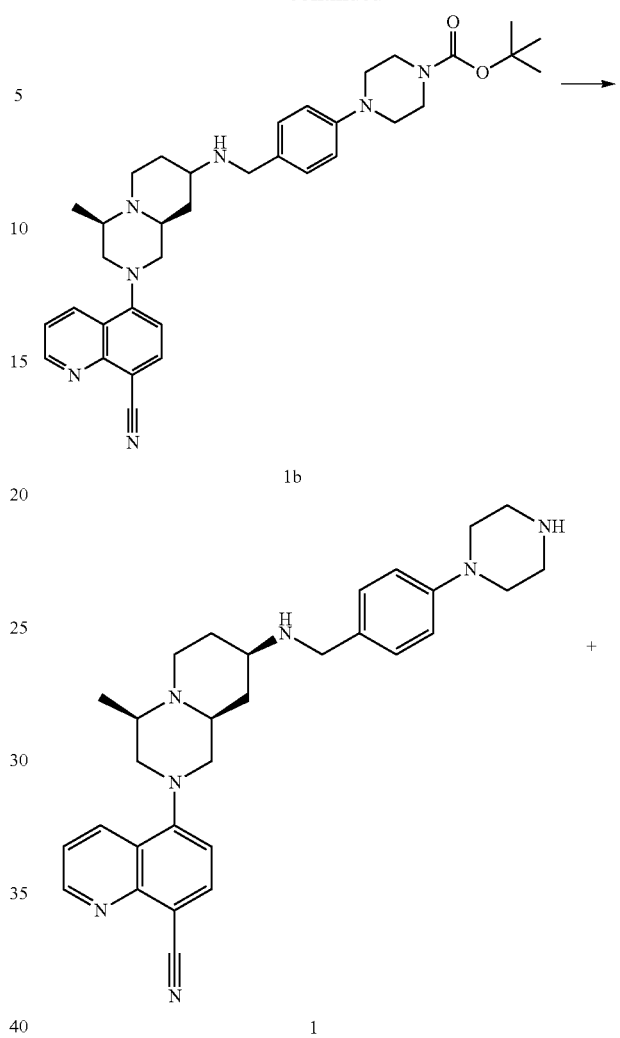
The title compound was prepared according to the following scheme:
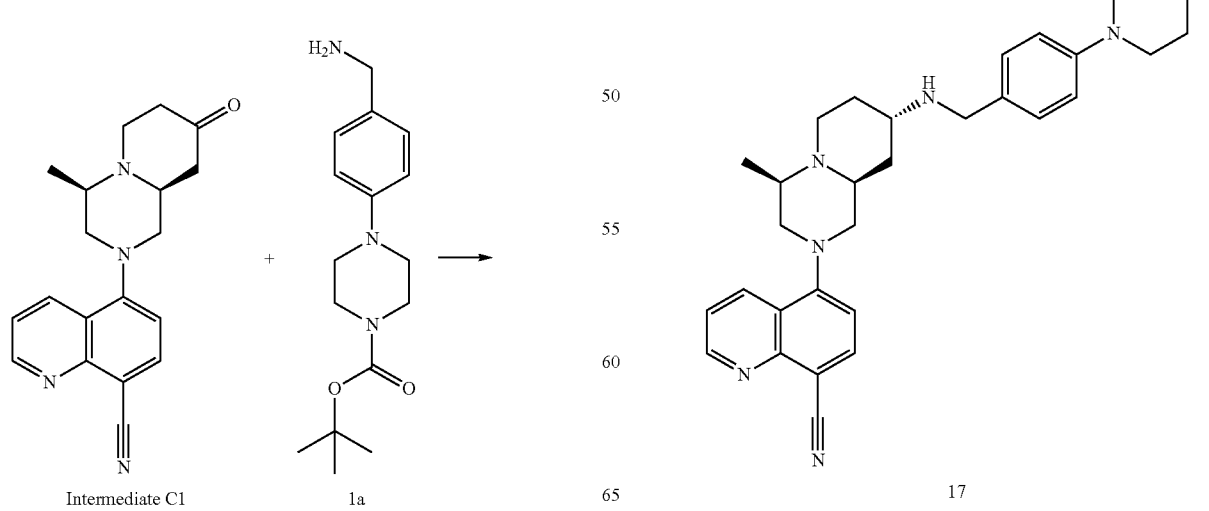

Step 1: tert-butyl 4-(4-((((4R,9aS)-2-(8-cyanoquinolin-5-yl)-4-methyloctahydro-2H-pyrido[1,2-a]pyrazin-8-yl)amino)methyl)phenyl)piperazine-1-carboxylate (compound 1b)

A solution of 5-((4R,9aS)-4-methyl-8-oxooctahydro-2H-pyrido[1,2-a]pyrazin-2-yl)quinoline-8-carbonitrile (Intermediate C1, 32 mg, 99.9 µmol), tert-butyl 4-(4-(aminomethyl)phenyl)piperazine-1-carboxylate (Compound 1a, CAS: 852180-47-3, Vendor: Accela ChemBio Inc, 29 mg, 99.9 µmol) in MeOH (4 mL) was stirred at room temperature for 1 hour. Then the reaction mixture was cooled at 0° C. and sodium cyanotrihydroborate (12 mg, 200 µmol) was added. The reaction mixture was stirred at room temperature for 12 hrs. The mixture was quenched with water (10 mL), extracted with EA twice. The combined organic layer was washed with brine, dried over $Na_2SO_4$, filtered and concentrated to afford crude tert-butyl 4-(4-((((4R,9aS)-2-(8-cyanoquinolin-5-yl)-4-methyloctahydro-2H-pyrido[1,2-a]pyrazin-8-yl)amino)methyl)phenyl)piperazine-1-carboxylate (Compound 1b, 50 mg) which was used for next step without purification. MS: calc'd 596 ($MH^+$), measured 596 ($MH^+$).

Step 2: 5-[(4R,8R,9aS)-4-methyl-8-[(4-piperazin-1-ylphenyl)methylamino]-1,3,4,6,7,8,9,9a-octahydropyrido[1,2-a]pyrazin-2-yl]quinoline-8-carbonitrile (Example 1)

5-[(4R,8S,9aS)-4-methyl-8-[(4-piperazin-1-ylphenyl)methylamino]-1,3,4,6,7,8,9,9a-octahydropyrido[1,2-a]pyrazin-2-yl]quinoline-8-carbonitrile (Example 17)

To a solution of tert-butyl 4-(4-((((4R,9aS)-2-(8-cyanoquinolin-5-yl)-4-methyloctahydro-2H-pyrido[1,2-a]pyrazin-8-yl)amino)methyl)phenyl)piperazine-1-carboxylate (Compound 1b, 50 mg, 83.9 µmol) in DCM (4 mL) was added TFA (0.5 mL) at 0° C. The reaction mixture was stirred at rt for 2 hrs. Then the mixture was concentrated to crude product, which was purified by prep-HPLC to afford Example 1 (3 mg) as a light yellow solid and Example 17 (4 mg) as a light yellow solid.

Example 1: The stereochemistry was confirmed by NOESY. MS calc'd 496 ($MH^+$), measured 496 ($MH^+$). $^1$H NMR (400 MHz, METHANOL-$d_4$) δ 8.99 (dd, J=1.7, 4.2 Hz, 1H), 8.62 (dd, J=1.7, 8.6 Hz, 1H), 8.16 (d, J=8.1 Hz, 1H), 7.65 (dd, J=4.2, 8.6 Hz, 1H), 7.26 (dd, J=8.4, 11.9 Hz, 3H), 6.98 (d, J=8.7 Hz, 2H), 3.78 (s, 2H), 3.46-3.37 (m, 2H), 3.19-3.11 (m, 4H), 3.03-2.97 (m, 4H), 2.89-2.51 (m, 6H), 2.15-1.92 (m, 3H), 1.58-1.45 (m, 1H), 1.33-1.23 (m, 1H), 1.19 (d, J=6.2 Hz, 3H).

Example 17: The stereochemistry was confirmed by NOESY. MS calc'd 496 ($MH^+$), measured 496 ($MH^+$). $^1$H NMR (400 MHz, METHANOL-$d_4$) δ 8.99 (dd, J=1.7, 4.2 Hz, 1H), 8.62 (dd, J=1.7, 8.6 Hz, 1H), 8.15 (d, J=8.1 Hz, 1H), 7.65 (dd, J=4.2, 8.6 Hz, 1H), 7.29 (d, J=8.6 Hz, 2H), 7.22 (d, J=8.1 Hz, 1H), 6.97 (d, J=8.7 Hz, 2H), 3.81-3.70 (m, 2H), 3.44-3.38 (m, 1H), 3.29-3.23 (m, 1H), 3.18-3.09 (m, 5H), 3.04-2.94 (m, 6H), 2.89-2.71 (m, 3H), 2.50-2.41 (m, 1H), 1.96-1.69 (m, 3H), 1.59-1.50 (m, 1H), 1.19 (d, J=5.9 Hz, 3H).

Example 2

5-[(4R,8R)-4-methyl-8-(6-piperazin-1-yl-3-pyridyl)-1,3,4,6,7,8,9,9a-octahydropyrido[1,2-a]pyrazin-2-yl]quinoline-8-carbonitrile

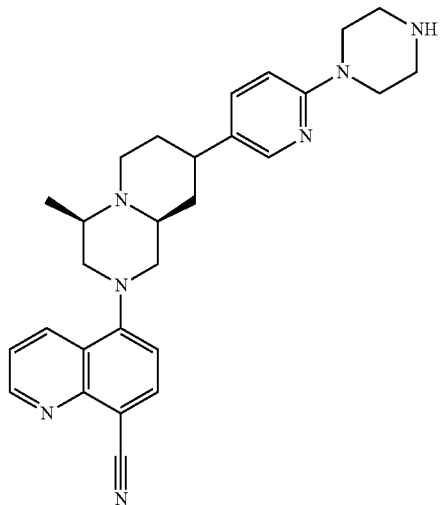

The title compound was prepared according to the following scheme:

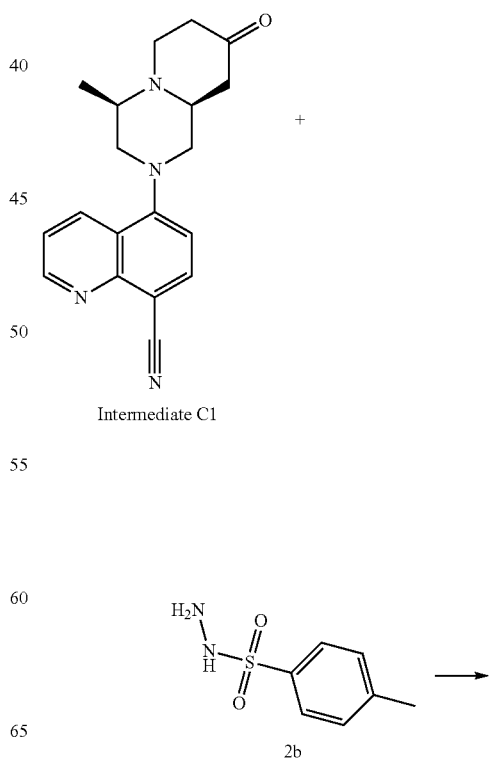

33
-continued

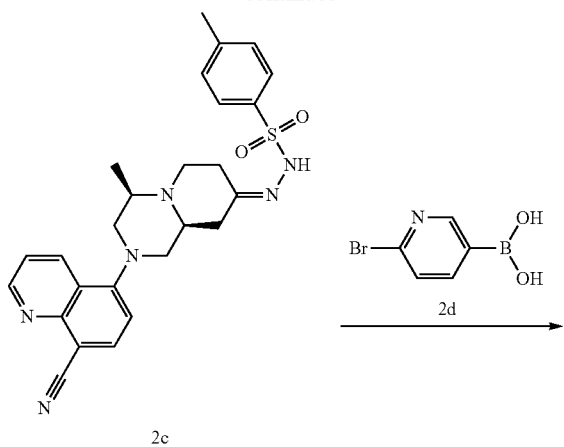

2c

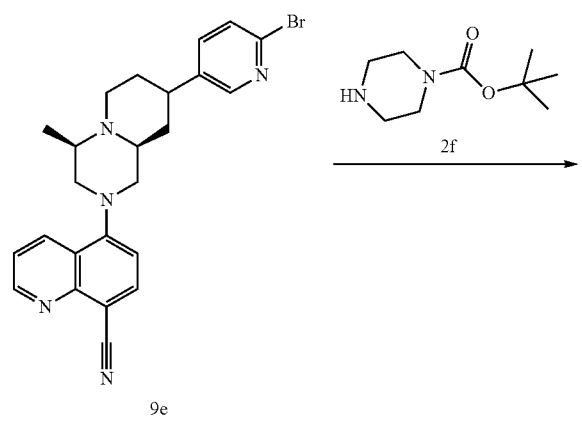

9e

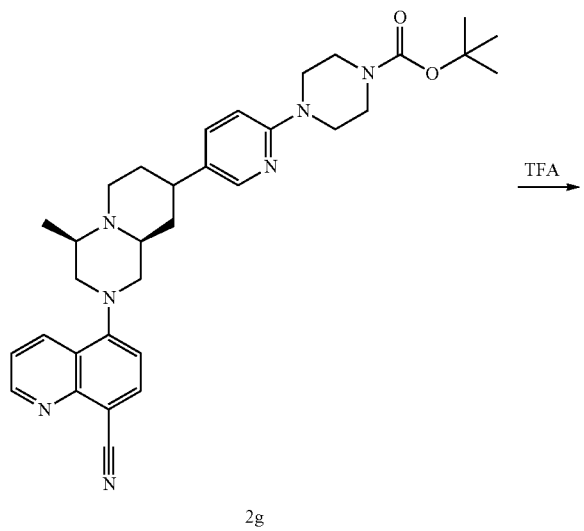

2g

34
-continued

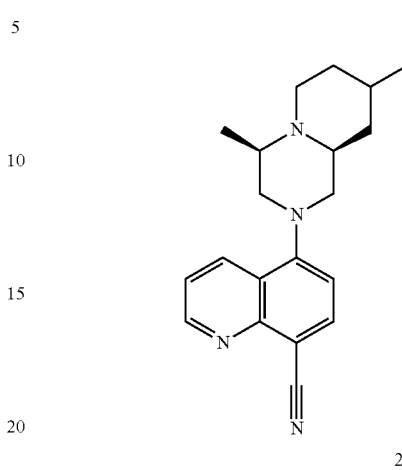

2

Step 1: N'-((4R,E)-2-(8-cyanoquinolin-5-yl)-4-methyloctahydro-8H-pyrido[1,2-a]pyrazin-8-ylidene)-4-methylbenzenesulfonohydrazide (compound 2c)

To a solution of 5-((4R)-4-methyl-8-oxooctahydro-2H-pyrido[1,2-a]pyrazin-2-yl)quinoline-8-carbonitrile (Intermediate C1, 387 mg, 1.21 mmol) in ethanol (8 mL) was added 4-methylbenzenesulfonohydrazide (Compound 2b, 225 mg, 1.21 mmol). The reaction mixture was stirred at 25° C. for 3 hrs. LCMS showed the starting material consumed, the reaction mixture was concentrated to afford crude N'-((4R,E)-2-(8-cyanoquinolin-5-yl)-4-methyloctahydro-8H-pyrido[1,2-a]pyrazin-8-ylidene)-4-methylbenzenesulfonohydrazide (compound 2c, 400 mg, 48.8% yield) which can be used in next step without purification as a yellow solid. MS calc'd 489 (MH$^+$); measured 489 (MH$^+$).

Step 2: 5-((4R)-8-(6-bromopyridin-3-yl)-4-methyloctahydro-2H-pyrido[1,2-a]pyrazin-2-yl)quinoline-8-carbonitrile (compound 2e)

To a solution of N-((4R,E)-2-(8-cyanoquinolin-5-yl)-4-methyloctahydro-8H-pyrido[1,2-a]pyrazin-8-ylidene)-4-methylbenzenesulfonohydrazide (compound 2c, 300 mg, 614 μmol) in 1,4-dioxane (2 mL) was added (6-bromopyridin-3-yl)boronic acid (compound 2d, 198 mg, 982 μmol), and Cs$_2$CO$_3$ (320 mg, 982 μmol). After being stirred at 120° C. for 16 hrs under N$_2$ atmosphere, then the mixture was concentrated to afford crude product, which was purified by silica gel column (PE/EA=3/1) to afford 5-((4R)-8-(6-bromopyridin-3-yl)-4-methyloctahydro-2H-pyrido[1,2-a]pyrazin-2-yl)quinoline-8-carbonitrile (compound 2e, 50 mg, 17.6% yield) as yellow oil. MS calc'd 463 (MH$^+$), measured 463 (MH$^+$).

Step 3: tert-butyl 4-(5-((4R)-2-(8-cyanoquinolin-5-yl)-4-methyloctahydro-2H-pyrido[1,2-a]pyrazin-8-yl)pyridin-2-yl)piperazine-1-carboxylate (compound 2g)

To a microwave tube was added 5-((4R)-8-(6-bromopyridin-3-yl)-4-methyloctahydro-2H-pyrido[1,2-a]pyrazin-2-yl)quinoline-8-carbonitrile (compound 2e, 50 mg, 108 μmol), tert-butyl piperazine-1-carboxylate (compound 2f, 26.2 mg, 141 μmol), sodium tert-butoxide (162 μl, 324 μmol) and 1,4-dioxane (5 mL), the suspension was bubbled with N$_2$ for 5 mins and tBuXPhos PD G3 (8.59 mg, 10.8 μmol) was added. After being stirred at 100° C. for 12 hrs, the mixture was cooled to room temperature, quenched with saturated NaHCO$_3$ (5 mL) solution and extracted with EtOAc (10 mL)

three times. The combined organic layer was washed with brine, dried over Na$_2$SO$_4$, filtered and concentrated. The residue was purified by flash chromatography (silica gel, 0% to 15% DCM in MeOH) to afford tert-butyl 4-(5-((4R)-2-(8-cyanoquinolin-5-yl)-4-methyloctahydro-2H-pyrido[1,2-a]pyrazin-8-yl)pyridin-2-yl)piperazine-1-carboxylate (compound 2g, 30 mg, 52.8 μmol) as an orange solid. MS: calc'd 568 (MH$^+$), measured 568 (MH$^+$).

Step 4: 5-[(4R,8R)-4-methyl-8-(6-piperazin-1-yl-3-pyridyl)-1,3,4,6,7,8,9,9a-octahydropyrido[1,2-a]pyrazin-2-yl]quinoline-8-carbonitrile (Example 2)

To a solution of tert-butyl 4-(5-((4R)-2-(8-cyanoquinolin-5-yl)-4-methyloctahydro-2H-pyrido[1,2-a]pyrazin-8-yl)pyridin-2-yl)piperazine-1-carboxylate (compound 2g, 30 mg, 52.8 μmol) in DCM (4 mL) was added TFA (0.5 mL) at 0° C. Then the mixture was concentrated to crude product, which was purified by prep-HPLC to afford Example 2 (2 mg) as a light yellow solid. MS calc'd 468 (MH$^+$), measured 468 (MH$^+$). $^1$H NMR (400 MHz, METHANOL-d$_4$) δ 8.90 (dd, J=1.7, 4.3 Hz, 1H), 8.56 (dd, J=1.6, 8.6 Hz, 1H), 8.06 (d, J=7.9 Hz, 1H), 7.96 (d, J=2.2 Hz, 1H), 7.56 (dd, J=4.3, 8.7 Hz, 1H), 7.47 (dd, J=2.5, 8.7 Hz, 1H), 7.16 (d, J=8.1 Hz, 1H), 6.76 (d, J=8.7 Hz, 1H), 3.50-3.43 (m, 4H), 3.37-3.29 (m, 2H), 3.00-2.93 (m, 4H), 2.82-2.74 (m, 2H), 2.70-2.64 (m, 2H), 2.18-2.08 (m, 1H), 1.91-1.84 (m, 1H), 1.78-1.67 (m, 2H), 1.52-1.40 (m, 1H), 1.23-1.21 (m, 1H), 1.20-1.17 (m, 1H), 1.14 (d, J=6.0 Hz, 3H).

Example 3

5-[(4R,8R)-4-methyl-8-(4-piperazin-1-ylphenyl)-1,3,4,6,7,8,9,9a-octahydropyrido[1,2-a]pyrazin-2-yl]quinoline-8-carbonitrile

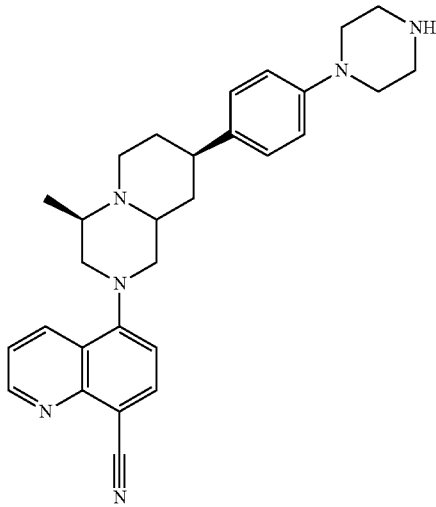 [SMILES: C[C@@H]1CN(c2ccc(C#N)c3ncccc23)CC2C[C@H](c3ccc(N4CCNCC4)cc3)CCN21]

The title compound was prepared in analogy to the preparation of Example 2 by using (4-bromophenyl)boronic acid instead of (6-bromopyridin-3-yl)boronic acid (compound 2d). Example 3 (17 mg) was obtained as a light grey solid. The stereochemistry was confirmed by NOESY. MS: calc'd 467 (MH$^+$), measured 467 (MH$^+$). $^1$H NMR (400 MHz, METHANOL-d$_4$) δ 9.07-9.00 (m, 1H), 8.71 (dd, J=1.7, 8.6 Hz, 1H), 8.26-8.18 (m, 1H), 7.76-7.66 (m, 1H), 7.38 (d, J=8.1 Hz, 1H), 7.29-7.22 (m, 2H), 7.08-7.00 (m, 2H), 4.26-4.05 (m, 1H), 4.03-3.80 (m, 2H), 3.79-3.64 (m, 2H), 3.63-3.49 (m, 1H), 3.48-3.34 (m, 8H), 3.24 (br d, J=11.7 Hz, 4H), 2.31-1.98 (m, 3H), 1.93-1.84 (m, 1H), 1.84-1.78 (m, 1H), 1.54 (d, J=6.5 Hz, 1H).

Example 4

5-[(4R,8R,9aS)-4-methyl-8-(6-piperazin-1-yl-3-pyridyl)-1,3,4,6,7,8,9,9a-octahydropyrido[1,2-a]pyrazin-2-yl]quinoline-8-carbonitrile

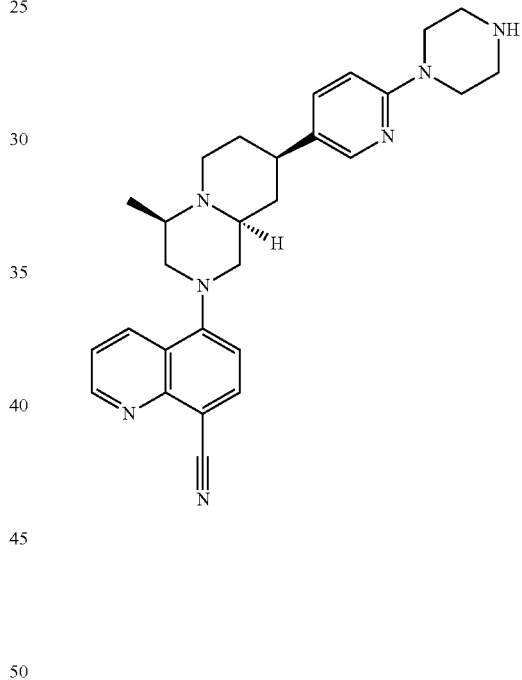

The title compound was prepared in analogy to the preparation of Example 2 by using (6-bromopyridin-3-yl)boronic acid instead of (6-bromopyridin-3-yl)boronic acid (compound 2d). Example 4 (8 mg) was obtained as a brown solid. The stereochemistry was confirmed by NOESY. MS: calc'd 468 (MH$^+$), measured 468 (MH$^+$). $^1$H NMR (400 MHz, METHANOL-d$_4$) δ 8.91 (dd, J=1.6, 4.3 Hz, 1H), 8.59 (dd, J=1.7, 8.6 Hz, 1H), 8.09 (d, J=7.9 Hz, 1H), 8.00 (d, J=2.3 Hz, 1H), 7.67 (dd, J=2.3, 9.0 Hz, 1H), 7.59 (dd, J=4.3, 8.7 Hz, 1H), 7.27 (d, J=8.1 Hz, 1H), 7.01 (d, J=8.9 Hz, 1H), 4.03-3.96 (m, 1H), 3.86-3.78 (m, 1H), 3.77-3.69 (m, 5H), 3.67-3.54 (m, 2H), 3.30-3.24 (m, 4H), 3.18-3.08 (m, 3H), 3.08-2.97 (m, 1H), 2.19-2.07 (m, 2H), 2.03-1.91 (m, 1H), 1.86-1.75 (m, 1H), 1.43 (d, J=6.4 Hz, 3H).

Example 6

5-[(4R,8R,9aS)-8-[6-[(3S,4S)-3-amino-4-methoxy-pyrrolidin-1-yl]-3-pyridyl]-4-methyl-1,3,4,6,7,8,9,9a-octahydropyrido[1,2-a]pyrazin-2-yl]quinoline-8-carbonitrile

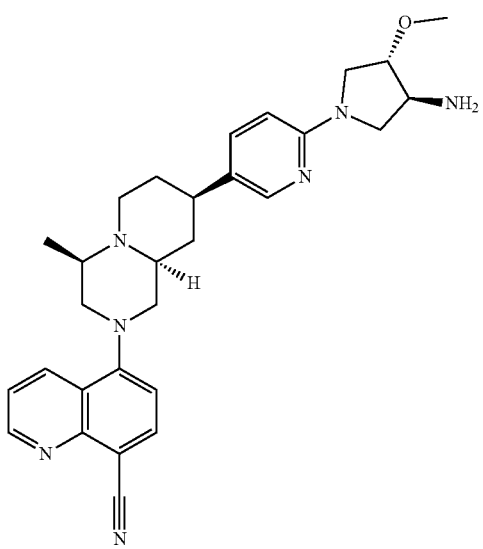 [SMILES: CO[C@H]1CN(c2ccc([C@@H]3CCN4[C@@H](C3)CN(c3ccc(C#N)c5ncccc35)C[C@H]4C)cn2)C[C@@H]1N]

The title compound was prepared in analogy to the preparation of Example 2 by using tert-butyl N-[(3S,4S)-4-methoxypyrrolidin-3-yl]carbamate (CAS: 1627185-88-9, PharmaBlock, Catalog #PBZ4724) instead of tert-butyl piperazine-1-carboxylate (compound 2f). Example 6 (21 mg) was obtained as a light yellow solid. The stereochemistry was confirmed by NOESY. MS: calc'd 498 (MH$^+$), measured 498 (MH$^+$). $^1$H NMR (400 MHz, METHANOL-d$_4$) δ 9.00 (dd, J=1.5, 4.3 Hz, 1H), 8.68 (dd, J=1.6, 8.7 Hz, 1H), 8.18 (d, J=7.9 Hz, 1H), 8.03 (dd, J=2.0, 9.3 Hz, 1H), 7.93 (d, J=2.0 Hz, 1H), 7.68 (dd, J=4.3, 8.6 Hz, 1H), 7.36 (d, J=8.1 Hz, 1H), 7.12 (d, J=9.3 Hz, 1H), 4.30-4.23 (m, 1H), 4.14-3.99 (m, 4H), 3.92 (br s, 1H), 3.88-3.79 (m, 2H), 3.79-3.62 (m, 3H), 3.49 (s, 3H), 3.29-3.12 (m, 4H), 2.31-2.19 (m, 2H), 2.16-2.04 (m, 1H), 2.01-1.89 (m, 1H), 1.53 (d, J=6.5 Hz, 3H).

Example 7

5-[(4R,8R,9aS)-8-[6-(3-aminoazetidin-1-yl)-3-pyridyl]-4-methyl-1,3,4,6,7,8,9,9a-octahydropyrido[1,2-a]pyrazin-2-yl]quinoline-8-carbonitrile

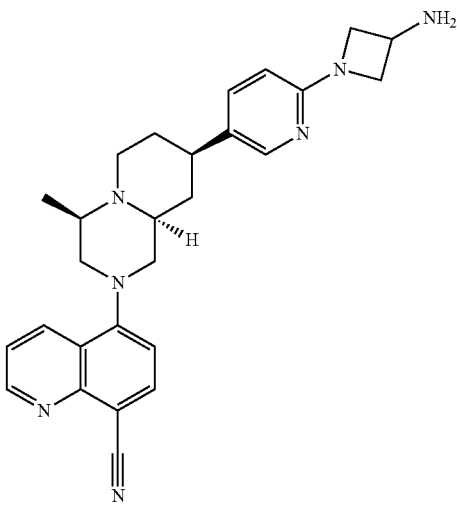 [SMILES: C[C@@H]1CN(c2ccc(C#N)c3ncccc23)C[C@@H]2C[C@H](c3ccc(N4CC(N)C4)nc3)CCN21]

The title compound was prepared in analogy to the preparation of Example 2 by using tert-butyl N-[(3S,4S)-4-methoxypyrrolidin-3-yl]carbamate (CAS: 1627185-88-9, PharmaBlock, Catalog #PBZ4724) instead of tert-butyl piperazine-1-carboxylate (compound 2f). Example 7 (14 mg) was obtained as a light yellow solid. The stereochemistry was confirmed by NOESY. MS: calc'd 454 (MH$^+$), measured 454 (MH$^+$). $^1$H NMR $^1$H NMR (400 MHz, METHANOL-d$_4$) δ 9.05 (dd, J=4.3, 1.6 Hz, 1H), 8.70 (dd, J=8.6, 1.6 Hz, 1H), 8.23 (d, J=7.9 Hz, 1H), 7.98 (d, J=2.0 Hz, 1H), 7.90 (dd, J=9.0, 2.2 Hz, 1H), 7.72 (dd, J=8.6, 4.3 Hz, 1H), 7.39 (d, J=8.1 Hz, 1H), 6.84 (d, J=9.0 Hz, 1H), 4.58 (dd, J=9.8, 7.2 Hz, 2H), 4.37-4.22 (m, 3H), 4.16-4.08 (m, 1H), 3.98-3.80 (m, 2H), 3.80-3.64 (m, 2H), 3.27-3.07 (m, 4H), 2.21 (br s, 2H), 2.13-1.99 (m, 1H), 1.90 (br d, J=14.1 Hz, 1H), 1.54 (d, J=6.5 Hz, 3H).

Example 9
5-[(4R,8R,9aS)-4-methyl-8-[3-(4-piperazin-1-ylphenyl)azetidin-1-yl]-1,3,4,6,7,8,9,9a-octahydropyrido[1,2-a]pyrazin-2-yl]quinoline-8-carbonitrile
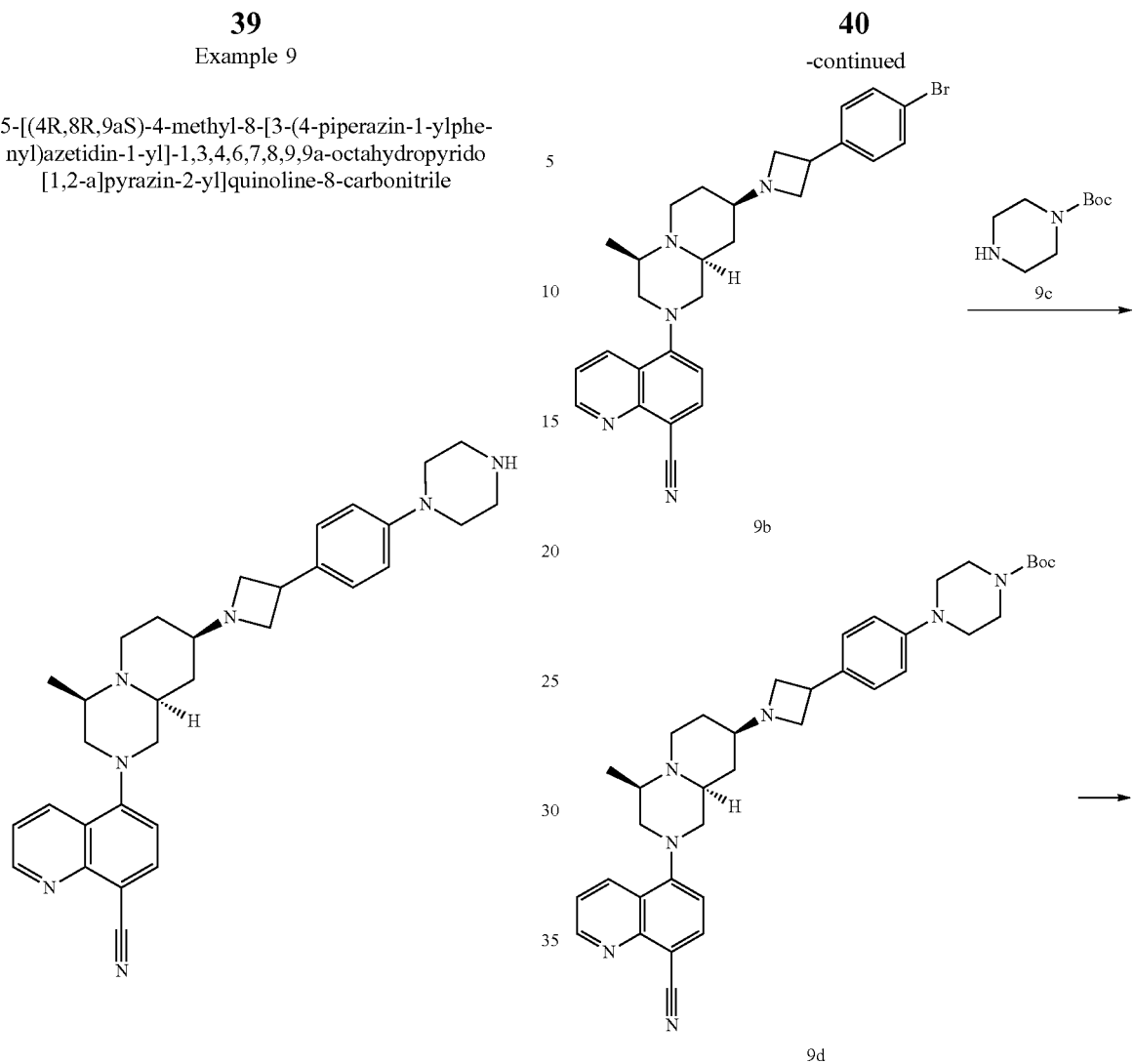
The title compound was prepared according to the following scheme:
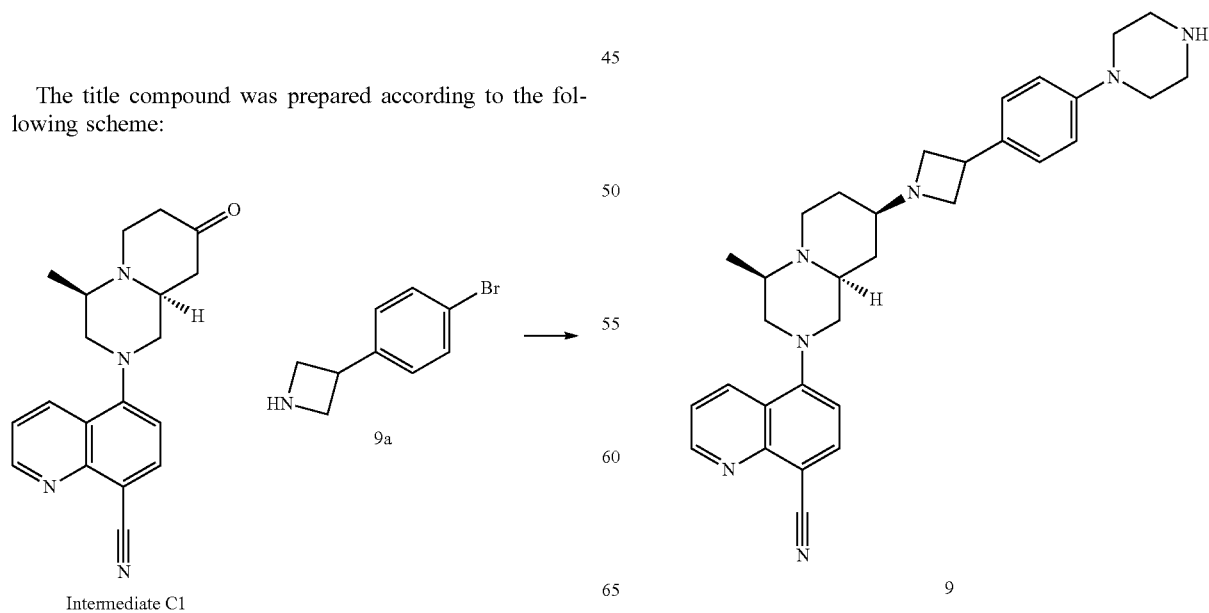

Step 1: 5-[(4R,8R,9aS)-8-[3-(4-bromophenyl)azetidin-1-yl]-4-methyl-1,3,4,6,7,8,9,9a-octahydropyrido[1,2-a]pyrazin-2-yl]quinoline-8-carbonitrile (compound 9b)

A solution of 5-((4R,9aS)-4-methyl-8-oxooctahydro-2H-pyrido[1,2-a]pyrazin-2-yl)quinoline-8-carbonitrile (Intermediate C1, 30 mg, 93 μmol), 3-(4-bromophenyl)azetidine (Compound 9a, 20 mg, 93 μmol) in MeOH (10 mL) was stirred at room temperature for 1 hour. Then the reaction mixture was cooled at 0° C. and sodium cyanotrihydroborate (17 mg, 281 μmol) was added. After being stirred at room temperature for 12 hrs, the mixture was quenched with water (10 mL), extracted with EA twice. The combined organic layer was washed with brine, dried over Na$_2$SO$_4$, filtered and concentrated to afford crude product which was purified by prep-HPLC to afford 5-[(4R,8R,9aS)-8-[3-(4-bromophenyl)azetidin-1-yl]-4-methyl-1,3,4,6,7,8,9,9a-octahydropyrido[1,2-a]pyrazin-2-yl]quinoline-8-carbonitrile (compound 9b, 20 mg). MS: calc'd 517 (MH$^+$), measured 517 (MH+). The stereochemistry was confirmed by NOESY.

Step 2: tert-butyl 4-[4-[1-[(4R,8R,9aS)-2-(8-cyano-5-quinolyl)-4-methyl-1,3,4,6,7,8,9,9a-octahydropyrido[1,2-a]pyrazin-8-yl]azetidin-3-yl]phenyl]piperazine-1-carboxylate (compound 9d)

A mixture of 5-[(4R,8R,9aS)-8-[3-(4-bromophenyl)azetidin-1-yl]-4-methyl-1,3,4,6,7,8,9,9a-octahydropyrido[1,2-a]pyrazin-2-yl]quinoline-8-carbonitrile.(compound 9b, 20 mg, 38.7 μmol), tert-butyl piperazine-1-carboxylate (compound 9c, 9.38 mg, 50.3 μmol), tBuXPhos Pd G3 (1.54 mg, 1.94 μmol) and sodium tert-butoxide (18.6 mg, 194 μmol) in 1,4-dioxane (10 mL) was charged with N$_2$. After being stirred at 90° C. overnight, the mixture was cooled to room temperature, the solid was filtered off and washed with EA (10 mL) twice. The filtrate was concentrated to crude product tert-butyl 4-[4-[1-[(4R,8R,9aS)-2-(8-cyano-5-quinolyl)-4-methyl-1,3,4,6,7,8,9,9a-octahydropyrido[1,2-a]pyrazin-8-yl]azetidin-3-yl]phenyl]piperazine-1-carboxylate (compound 9d, 25 mg) which can be used in next step without purification. MS: calc'd 622 (MH$^+$), measured 622 (MH$^+$).

Step 3: 5-[(4R,8R,9aS)-4-methyl-8-[3-(4-piperazin-1-ylphenyl)azetidin-1-yl]-1,3,4,6,7,8,9,9a-octahydropyrido[1,2-a]pyrazin-2-yl]quinoline-8-carbonitrile (Example 9)

To a solution of tert-butyl 4-[4-[1-[(4R,8R,9aS)-2-(8-cyano-5-quinolyl)-4-methyl-1,3,4,6,7,8,9,9a-octahydropyrido[1,2-a]pyrazin-8-yl]azetidin-3-yl]phenyl]piperazine-1-carboxylate (compound 9d, 25 mg) in DCM (4 mL) was added TFA (0.5 mL) at 0° C. The reaction mixture was stirred at rt for 2 hrs. Then the mixture was concentrated to crude product, which was purified by prep-HPLC to afford Example 9 (11 mg) as a light yellow solid. MS: calc'd 522 (MH$^+$), measured 522 (MH$^+$). $^1$H NMR (400 MHz, METHANOL-d$_4$) δ 8.92 (dd, J=4.3, 1.6 Hz, 1H), 8.55 (dd, J=8.6, 1.7 Hz, 1H), 8.09 (d, J=7.9 Hz, 1H), 7.58 (dd, J=8.6, 4.3 Hz, 1H), 7.25 (t, J=8.4 Hz, 3H), 6.92-7.04 (m, 2H), 4.35-4.51 (m, 2H), 4.11-4.30 (m, 2H), 3.80-4.07 (m, 2H), 3.38-3.71 (m, 5H), 3.26-3.37 (m, 6H), 2.90-3.12 (m, 2H), 2.69-2.85 (m, 1H), 2.18-2.42 (m, 2H), 1.47-1.81 (m, 2H), 1.32 ppm (d, J=6.4 Hz, 3H).

Example 11

5-[(4R,8S,9aS)-4-methyl-8-[(5-piperazin-1-yl-2-pyridyl)oxy]-1,3,4,6,7,8,9,9a-octahydropyrido[1,2-a]pyrazin-2-yl]quinoline-8-carbonitrile

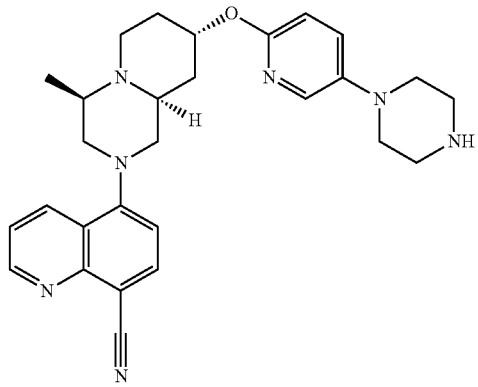 [SMILES: C[C@@H]1CN(c2ccc(C#N)c3ncccc23)C[C@@H]2C[C@@H](Oc3ccc(N4CCNCC4)cn3)CCN21]

The title compound was prepared according to the following scheme:

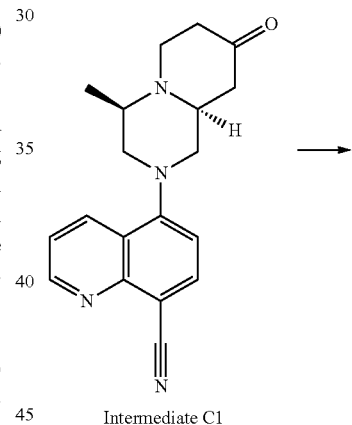

Intermediate C1

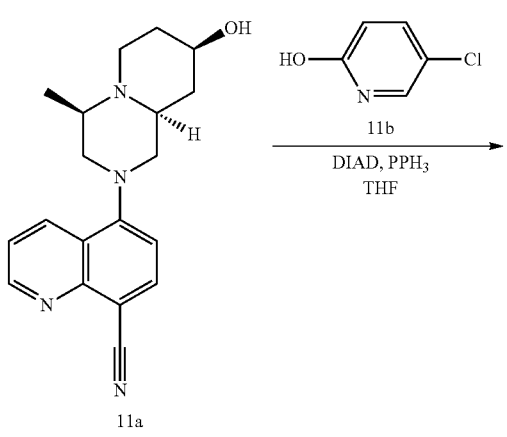

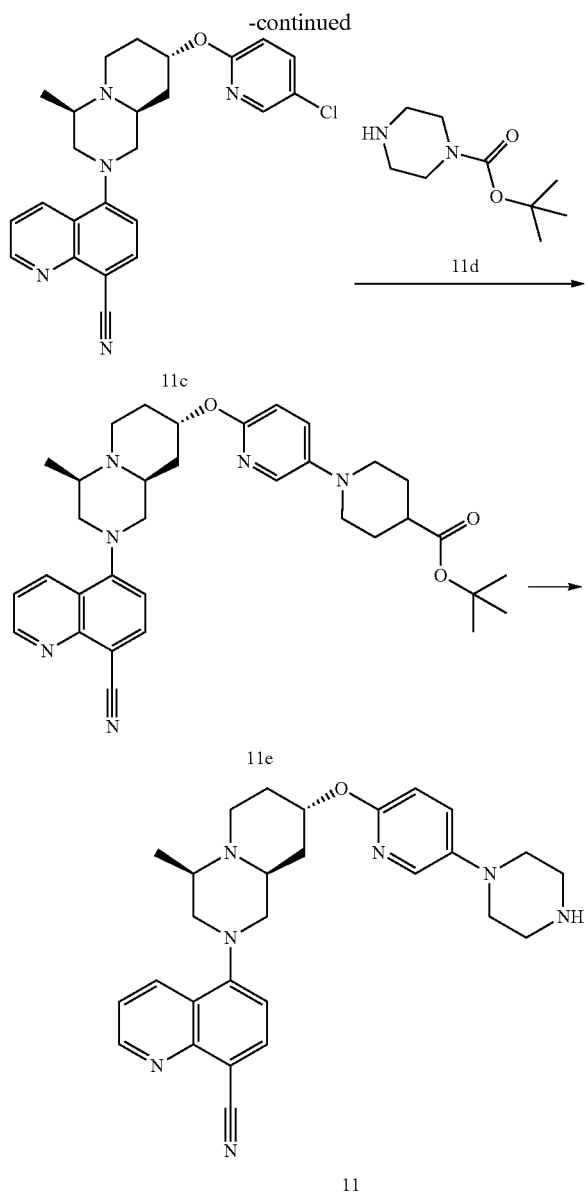

Step 1: 5-((4R,8R)-8-hydroxy-4-methyloctahydro-2H-pyrido[1,2-a]pyrazin-2-yl)quinoline-8-carbonitrile (compound 11a)

To a solution of 5-((4R)-4-methyl-8-oxooctahydro-2H-pyrido[1,2-a]pyrazin-2-yl)quinoline-8-carbonitrile (Intermediate C1, 500 mg, 1.56 mmol) in MeOH (10 mL) was added sodium tetrahydroborate (70.8 mg, 1.87 mmol). After being stirred at room temperature for 2 hours, the reaction was quenched carefully with 10% HCl solution. The resulting mixture was neutralized with $K_2CO_3$ and extracted with EtOAc (30 mL) twice. The combined organic layer was washed with brine and dried over $Na_2SO_4$, filtered and concentrated to afford 5-((4R,8R)-8-hydroxy-4-methyloctahydro-2H-pyrido[1,2-a]pyrazin-2-yl)quinoline-8-carbonitrile (compound 11a, 500 mg) which was used directly for the next step without further purification. The stereochemistry was confirmed by NOESY. MS: calc'd 323 (MH$^+$), measured 323 (MH$^+$). 1H NMR (DMSO-d6, 400 MHz) δ 9.03 (dd, 1H, J=1.6, 4.2 Hz), 8.51 (dd, 1H, J=1.5, 8.6 Hz), 8.22 (d, 1H, J=8.1 Hz), 7.67 (dd, 1H, J=4.3, 8.6 Hz), 7.18 (d, 1H, J=8.2 Hz), 4.69 (d, 1H, J=4.6 Hz), 3.48 (dt, 1H, J=5.6, 10.4 Hz), 3.2-3.3 (m, 1H), 3.20 (br d, 1H, J=11.4 Hz), 2.6-2.8 (m, 2H), 2.3-2.4 (m, 1H), 1.7-1.9 (m, 3H), 1.3-1.5 (m, 1H), 1.0-1.1 (m, 1H), 1.0-1.1 (m, 3H).

Step 2: 5-((4R,8S,9aS)-8-((5-chloropyridin-2-yl)oxy)-4-methyloctahydro-2H-pyrido[1,2-a]pyrazin-2-yl)quinoline-8-carbonitrile (compound 11c)

A solution of 5-((4R,9aS)-8-hydroxy-4-methyloctahydro-2H-pyrido[1,2-a]pyrazin-2-yl)quinoline-8-carbonitrile (compound 11a, 60 mg, 186 μmol), 5-chloropyridin-2-ol (compound 11b, 24 mg, 186 μmol) and $PPh_3$ (98 mg, 372 μmol) in THF (4 mL) at 0° C. was treated with DIAD (72 μL, 372 μmol), stirred at room temperature for 1 hour. After being stirred at 70° C. for 1 hour, the mixture was cooled to room temperature, diluted with EtOAc, washed with water and brine, dried over $Na_2SO_4$ and concentrated. The residue was purified by silica gel column chromatography (20% to 100% EtOAc/PE) to afford 5-((4R,8S,9aS)-8-((5-chloropyridin-2-yl)oxy)-4-methyloctahydro-2H-pyrido[1,2-a]pyrazin-2-yl)quinoline-8-carbonitrile ((compound 11c, 40 mg) as a pale yellow solid. MS: calc'd 434 (MH$^+$), measured 434 (MH$^+$). The stereochemistry was confirmed by NOESY.

Step 3: tert-butyl 4-(6-(((4R,8S,9aS)-2-(8-cyanoquinolin-5-yl)-4-methyloctahydro-2H-pyrido[1,2-a]pyrazin-8-yl)oxy)pyridin-3-yl)piperazine-1-carboxylate (compound 11e)

To a microwave tube was added 5-((4R,8S,9aS)-8-((5-chloropyridin-2-yl)oxy)-4-methyloctahydro-2H-pyrido[1,2-a]pyrazin-2-yl)quinoline-8-carbonitrile (compound 11c, 40 mg, 92.2 μmol), tert-butyl piperazine-1-carboxylate (compound 11d, 22 mg, 120 μmol), sodium tert-butoxide (138 μL, 277 μmol, 2M in THF) and 1,4-dioxane (5 mL), the suspension was bubbled with $N_2$ for 5 mins and tBuXPhos PD G3 (7 mg, 9.22 μmol) was added. After being stirred at 100° C. for 12 hrs, the mixture was cooled to room temperature, diluted with saturated $NaHCO_3$ (5 mL) solution and extracted with EtOAC (10 mL) three times. The combined organic layer was washed with brine, dried over $Na_2SO_4$, and concentrated to afford tert-butyl 4-(6-(((4R,8S,9aS)-2-(8-cyanoquinolin-5-yl)-4-methyloctahydro-2H-pyrido[1,2-a]pyrazin-8-yl)oxy)pyridin-3-yl)piperazine-1-carboxylate (compound 11e, 20 mg) as an orange solid which can be used in next step without purification. MS: calc'd 584 (MH$^+$), measured 584 (MH$^+$).

Step 4: 5-[(4R,8S,9aS)-4-methyl-8-[(5-piperazin-1-yl-2-pyridyl)oxy]-1,3,4,6,7,8,9,9a-octahydropyrido[1,2-a]pyrazin-2-yl]quinoline-8-carbonitrile (Example 11)

To a solution of tert-butyl 4-(6-(((4R,8S,9aS)-2-(8-cyanoquinolin-5-yl)-4-methyloctahydro-2H-pyrido[1,2-a]pyrazin-8-yl)oxy)pyridin-3-yl)piperazine-1-carboxylate (compound 11e, 20 mg) in DCM (2 mL) was added TFA (0.5 mL) at 0° C. The reaction mixture was stirred at rt for 2 hrs. Then the mixture was concentrated to crude product, which was purified by prep-HPLC to afford Example 11 (16 mg) as a light brown solid. MS calc'd 484 (MH$^+$), measured 484 (MH$^+$). $^1$H NMR (400 MHz, METHANOL-d$_4$) δ 9.02 (dd, J=4.2, 1.7 Hz, 1H), 8.70 (dd, J=8.6, 1.7 Hz, 1H), 8.20 (d, J=8.1 Hz, 1H), 7.89 (d, J=2.9 Hz, 1H), 7.69 (dd, J=8.7, 4.3 Hz, 1H), 7.57 (dd, J=9.0, 3.1 Hz, 1H), 7.38 (d, J=8.1 Hz, 1H), 6.93 (d, J=8.9 Hz, 1H), 5.45 (br s, 1H), 4.17-4.09 (m, 1H), 4.00-3.87 (m, 2H), 3.78-3.71 (m, 1H), 3.66-3.59 (m, 1H), 3.45-3.34 (m, 9H), 3.21 (td, J=14.0, 11.1 Hz, 2H), 2.48-2.36 (m, 2H), 2.27-2.16 (m, 1H), 2.12-2.01 (m, 1H), 1.52 (d, J=6.5 Hz, 3H).

Example 12

5-[(4R,8R,9aS)-8-[6-[(3R,4S)-3-amino-4-methoxy-pyrrolidin-1-yl]-3-pyridyl]-4-methyl-1,3,4,6,7,8,9,9a-octahydropyrido[1,2-a]pyrazin-2-yl]quinoline-8-carbonitrile

Example 13

5-[(4R,8R,9aS)-8-[6-[(3S,4R)-3-amino-4-methoxy-pyrrolidin-1-yl]-3-pyridyl]-4-methyl-1,3,4,6,7,8,9,9a-octahydropyrido[1,2-a]pyrazin-2-yl]quinoline-8-carbonitrile

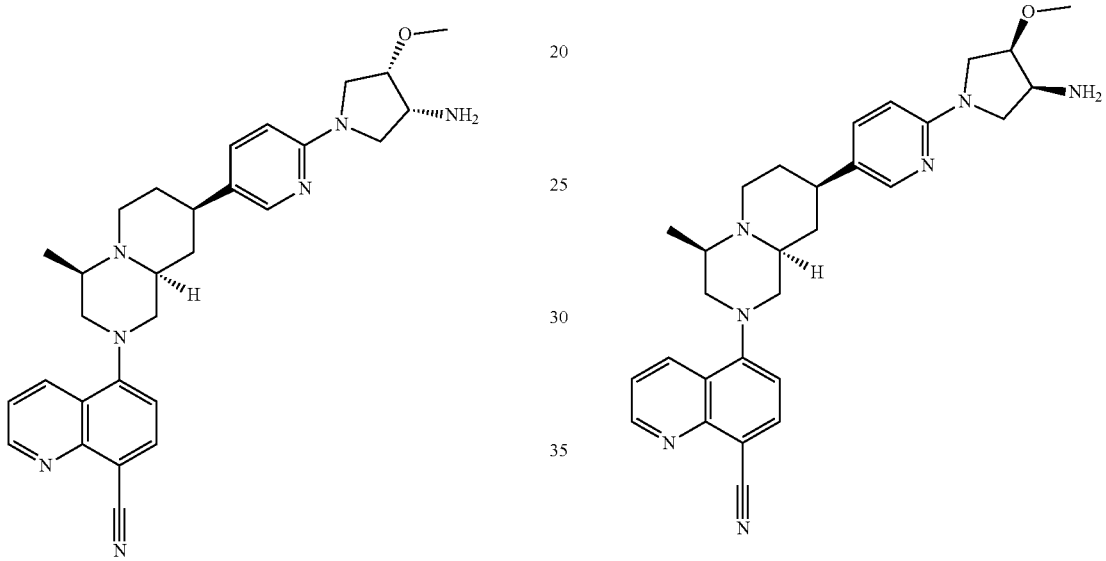

The title compound was prepared in analogy to the preparation of Example 2 by using tert-butyl ((3R,4S)-4-methoxypyrrolidin-3-yl)carbamate (CAS: 1932508-77-4, PharmaBlock) instead of tert-butyl piperazine-1-carboxylate (compound 2f). Example 12 (9 mg) was obtained as a light yellow solid. The stereochemistry was confirmed by NOESY. MS: calc'd 498 (MH$^+$), measured 498 (MH$^+$). $^1$H NMR (400 MHz, METHANOL-d$_4$) δ 9.02 (dd, J=4.3, 1.6 Hz, 1H), 8.70 (dd, J=8.6, 1.6 Hz, 1H), 8.20 (d, J=8.1 Hz, 1H), 8.06 (dd, J=9.4, 2.0 Hz, 1H), 7.99-7.94 (m, 1H), 7.70 (dd, J=8.6, 4.3 Hz, 1H), 7.38 (d, J=8.1 Hz, 1H), 7.14 (d, J=9.4 Hz, 1H), 4.36 (dt, J=4.5, 2.3 Hz, 1H), 4.22-4.04 (m, 3H), 3.99-3.65 (m, 7H), 3.53 (s, 3H), 3.31-3.14 (m, 4H), 2.34-2.07 (m, 3H), 2.05-1.92 (m, 1H), 1.55 (d, J=6.5 Hz, 3H).

The title compound was prepared in analogy to the preparation of Example 2 by using tert-butyl ((3S,4R)-4-methoxypyrrolidin-3-yl)carbamate (CAS: 1931911-57-7, PharmaBlock, Catalog #PBZ4730) instead of tert-butyl piperazine-1-carboxylate (compound 2f). Example 13 (15 mg) was obtained as a light yellow solid. The stereochemistry was confirmed by NOESY. MS: calc'd 498 (MH$^+$), measured 498 (MH$^+$). $^1$H NMR (400 MHz, METHANOL-d$_4$) δ 9.02 (dd, J=4.2, 1.5 Hz, 1H), 8.70 (dd, J=8.6, 1.6 Hz, 1H), 8.20 (d, J=7.9 Hz, 1H), 8.06 (dd, J=9.4, 2.0 Hz, 1H), 7.99-7.93 (m, 1H), 7.70 (dd, J=8.6, 4.3 Hz, 1H), 7.38 (d, J=7.9 Hz, 1H), 7.14 (d, J=9.3 Hz, 1H), 4.36 (td, J=4.5, 2.4 Hz, 1H), 4.21-4.05 (m, 3H), 3.99-3.90 (m, 2H), 3.89-3.79 (m, 2H), 3.78-3.65 (m, 3H), 3.53 (s, 3H), 3.31-3.14 (m, 4H), 2.34-2.07 (m, 3H), 2.04-1.92 (m, 1H), 1.55 (d, J=6.4 Hz, 3H).

Example 14

5-[(4R,8R,9aS)-8-[6-[(3R,4R)-3-amino-4-methoxy-pyrrolidin-1-yl]-3-pyridyl]-4-methyl-1,3,4,6,7,8,9,9a-octahydropyrido[1,2-a]pyrazin-2-yl]quinoline-8-carbonitrile

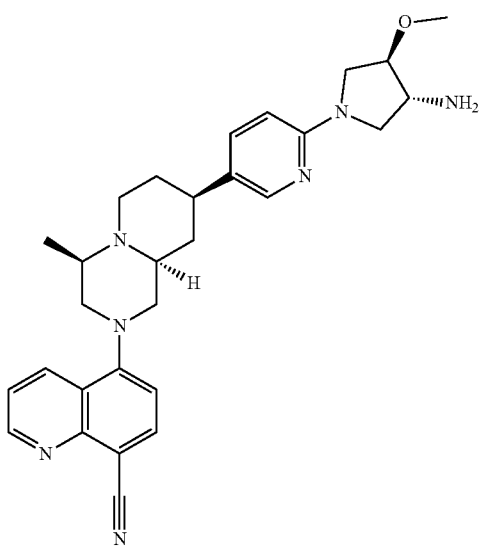 [SMILES: CO[C@@H]1CN(c2ccc([C@@H]3CCN4[C@@H](C3)CN(c3ccc(C#N)c5ncccc35)C[C@H]4C)cn2)C[C@H]1N]

The title compound was prepared in analogy to the preparation of Example 2 by using tert-butyl ((3R,4R)-4-methoxypyrrolidin-3-yl)carbamate (CAS: 1932066-52-8, PharmaBlock, Catalog #PBZ4728) instead of tert-butyl piperazine-1-carboxylate (compound 2f). Example 13 (10 mg) was obtained as a light yellow solid. The stereochemistry was confirmed by NOESY. MS: calc'd 498 (MH$^+$), measured 498 (MH$^+$). $^1$H NMR (400 MHz, METHANOL-d$_4$) δ 9.04 (dd, J=4.2, 1.5 Hz, 1H), 8.71 (dd, J=8.6, 1.7 Hz, 1H), 8.22 (d, J=7.9 Hz, 1H), 8.01-7.95 (m, 2H), 7.71 (dd, J=8.6, 4.2 Hz, 1H), 7.39 (d, J=7.9 Hz, 1H), 7.06 (d, J=10.0 Hz, 1H), 4.26 (dt, J=5.5, 2.8 Hz, 1H), 4.16-4.09 (m, 1H), 4.09-3.99 (m, 3H), 3.98-3.82 (m, 2H), 3.82-3.66 (m, 4H), 3.51 (s, 3H), 3.30-3.13 (m, 4H), 2.34-2.20 (m, 2H), 2.16-2.03 (m, 1H), 2.00-1.88 (m, 1H), 1.55 (d, J=6.4 Hz, 3H).

Example 15

5-[(4R,8R,9aR)-4-methyl-8-(6-piperazin-1-yl-3-pyridyl)-1,3,4,6,7,8,9,9a-octahydropyrido[1,2-a]pyrazin-2-yl]quinoline-8-carbonitrile

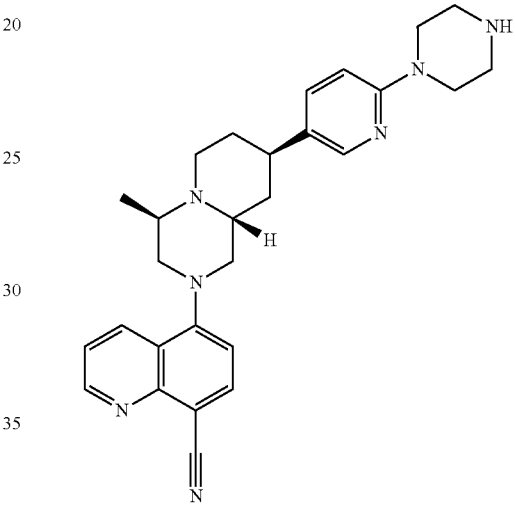

The title compound was prepared in analogy to the preparation of Example 2 by using 5-((4R,8R,9aR)-8-(6-bromopyridin-3-yl)-4-methyloctahydro-2H-pyrido[1,2-a]pyrazin-2-yl)quinoline-8-carbonitrile instead of 5-((4R)-8-(6-bromopyridin-3-yl)-4-methyloctahydro-2H-pyrido[1,2-a]pyrazin-2-yl)quinoline-8-carbonitrile (compound 2e). Example 15 (4 mg) was obtained as a light yellow solid. The stereochemistry was confirmed by NOESY. MS: calc'd 468 (MH$^+$), measured 468 (MH$^+$). $^1$H NMR (400 MHz, METHANOL-d$_4$) δ 8.99 (dd, J=4.2, 1.7 Hz, 1H), 8.73 (dd, J=8.6, 1.7 Hz, 1H), 8.16 (d, J=8.1 Hz, 1H), 8.03 (d, J=2.3 Hz, 1H), 7.66 (dd, J=8.6, 4.3 Hz, 1H), 7.54 (dd, J=8.7, 2.4 Hz, 1H), 7.27 (d, J=8.1 Hz, 1H), 6.83 (d, J=8.7 Hz, 1H), 3.52-3.35 (m, 8H), 3.31-3.26 (m, 1H), 3.25-3.14 (m, 1H), 2.98-2.82 (m, 6H), 2.80-2.65 (m, 2H), 1.93-1.77 (m, 2H), 1.65-1.49 (m, 1H), 1.48-1.43 (m, 3H).

Example 16

5-[(4R,8S,9aS)-4-methyl-8-[(6-piperazin-1-yl-3-pyridyl)oxy]-1,3,4,6,7,8,9,9a-octahydropyrido[1,2-a]pyrazin-2-yl]quinoline-8-carbonitrile

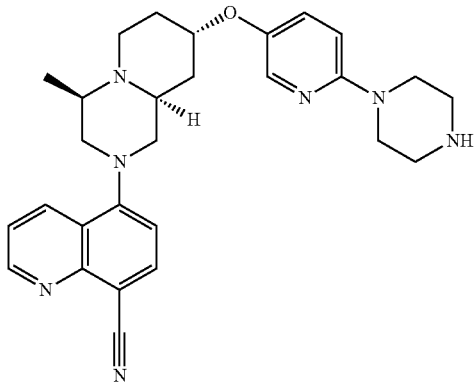 [SMILES: C[C@@H]1CN(c2ccc(C#N)c3ncccc23)C[C@@H]2C[C@@H](Oc3ccc(N4CCNCC4)nc3)CCN21]

The title compound was prepared in analogy to the preparation of Example 11 by using 5-bromo-2-hydroxypyridine (PharmaBlock, CAS: 13466-38-1) instead of 5-chloropyridin-2-ol (compound 11b). Example 16 (50 mg) was obtained as a white solid. The stereochemistry was confirmed by NOESY. MS: calc'd 484 (MH$^+$), measured 484 (MH$^+$). $^1$H NMR (400 MHz, METHANOL-d$_4$) δ 8.94 (dd, J=4.2, 1.6 Hz, 1H), 8.57 (dd, J=8.6, 1.6 Hz, 1H), 8.11 (d, J=7.9 Hz, 1H), 7.76 (d, J=2.8 Hz, 1H), 7.61 (dd, J=8.6, 4.2 Hz, 1H), 7.45 (dd, J=8.9, 3.1 Hz, 1H), 7.20 (d, J=7.9 Hz, 1H), 6.79 (d, J=8.9 Hz, 1H), 5.21 (t, J=2.4 Hz, 1H), 3.40 (br d, J=11.2 Hz, 1H), 3.26 (br d, J=11.7 Hz, 1H), 3.21-3.15 (m, 1H), 3.07-3.01 (m, 4H), 3.01-2.94 (m, 5H), 2.85-2.72 (m, 3H), 2.49-2.36 (m, 1H), 2.14-2.06 (m, 1H), 2.01-1.87 (m, 2H), 1.70-1.61 (m, 1H), 1.18 (d, J=5.9 Hz, 3H).

Example 18

5-[(4R,8S,9aS)-4-methyl-8-(2-piperazin-1-ylpyrimidin-5-yl)oxy-1,3,4,6,7,8,9,9a-octahydropyrido[1,2-a]pyrazin-2-yl]quinoline-8-carbonitrile

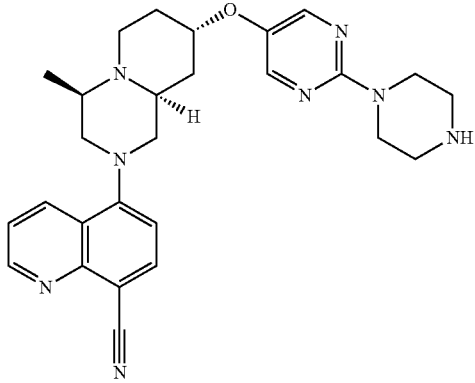 [SMILES: C[C@@H]1CN(c2ccc(C#N)c3ncccc23)C[C@@H]2C[C@@H](Oc3cnc(N4CCNCC4)nc3)CCN21]

The title compound was prepared in analogy to the preparation of Example 11 by using 2-Chloro-5-hydroxypyrimidine (Accela ChemBio Inc, CAS: 4983-28-2) instead of 5-chloropyridin-2-ol (compound 11b). Example 18 (27 mg) was obtained as a light yellow solid. The stereochemistry was confirmed by NOESY. MS: calc'd 485 (MH$^+$), measured 485 (MH$^+$). $^1$H NMR (400 MHz, METHANOL-d$_4$) δ 9.04 (dd, J=4.2, 1.7 Hz, 1H), 8.71 (dd, J=8.6, 1.7 Hz, 1H), 8.37 (s, 2H), 8.22 (d, J=7.9 Hz, 1H), 7.71 (dd, J=8.6, 4.3 Hz, 1H), 7.38 (d, J=7.9 Hz, 1H), 4.79 (br s, 1H), 4.21-4.12 (m, 1H), 4.06-4.00 (m, 4H), 3.99-3.87 (m, 2H), 3.79-3.72 (m, 1H), 3.70-3.62 (m, 1H), 3.50-3.40 (m, 1H), 3.32-3.28 (m, 4H), 3.21 (td, J=13.7, 11.2 Hz, 2H), 2.42-2.35 (m, 2H), 2.25-2.13 (m, 1H), 2.10-2.00 (m, 1H), 1.52 (d, J=6.5 Hz, 3H).

Example 19

5-[(4R,8R,9aS)-8-[6-[(3R,4S)-3-amino-4-fluoropyrrolidin-1-yl]-3-pyridyl]-4-methyl-1,3,4,6,7,8,9,9a-octahydropyrido[1,2-a]pyrazin-2-yl]quinoline-8-carbonitrile

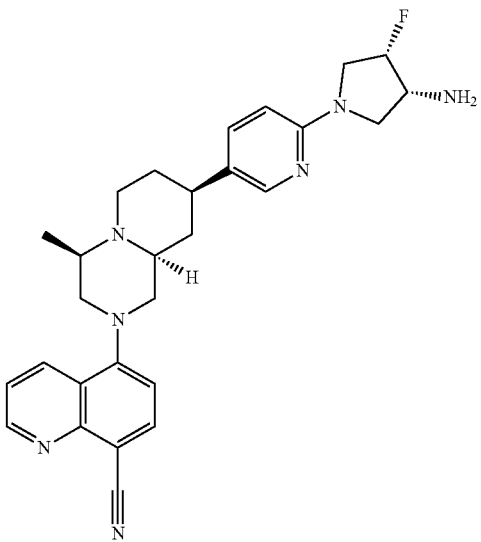 [SMILES: C[C@@H]1CN(c2ccc(C#N)c3ncccc23)C[C@@H]2C[C@H](c3ccc(N4C[C@@H](N)[C@@H](F)C4)nc3)CCN21]

The title compound was prepared in analogy to the preparation of Example 2 by using tert-butyl N-[(3R,4S)-4-fluoropyrrolidin-3-yl]carbamate (CAS: 1033718-91-0, PharmaBlock, Catalog #PB09204) instead of tert-butyl piperazine-1-carboxylate (compound 2f). Example 19 (5 mg) was obtained as a light yellow solid. The stereochemistry was confirmed by NOESY. MS: calc'd 486 (MH$^+$), measured 486 (MH$^+$). $^1$H NMR (400 MHz, METHANOL-d$_4$) δ 9.04 (dd, J=4.3, 1.6 Hz, 1H), 8.71 (dd, J=8.6, 1.6 Hz, 1H), 8.22 (d, J=7.9 Hz, 1H), 8.05 (dd, J=9.2, 2.3 Hz, 1H), 8.00 (d, J=1.8 Hz, 1H), 7.71 (dd, J=8.6, 4.3 Hz, 1H), 7.39 (d, J=7.9 Hz, 1H), 7.12 (d, J=9.3 Hz, 1H), 5.69-5.51 (m, 1H), 4.34-4.20 (m, 2H), 4.17-4.03 (m, 3H), 4.00-3.80 (m, 3H), 3.79-3.65 (m, 3H), 3.31-3.14 (m, 4H), 2.34-2.21 (m, 2H), 2.19-2.06 (m, 1H), 2.03-1.91 (m, 1H), 1.55 (d, J=6.4 Hz, 3H).

Example 20

5-[(4R,8R,9aS)-4-methyl-8-[4-[(2S)-morpholin-2-yl]anilino]-1,3,4,6,7,8,9,9a-octahydropyrido[1,2-a]pyrazin-2-yl]quinoline-8-carbonitrile

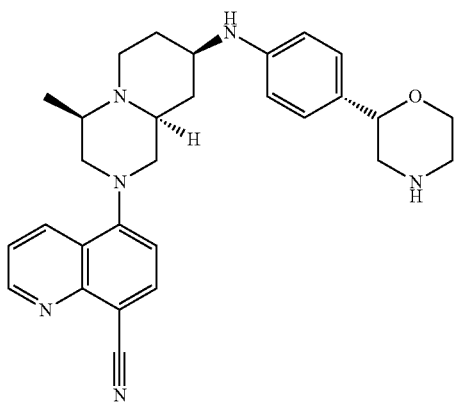

The title compound was prepared in analogy to the preparation of Example 1 by using tert-butyl (2S)-2-(4-aminophenyl)morpholine-4-carboxylate instead of tert-butyl 4-(4-(aminomethyl)phenyl)piperazine-1-carboxylate (Compound 1a) in step 1. Example 20 (7 mg) was obtained as a light yellow solid. The stereochemistry was confirmed by NOESY. MS: calc'd 483 (MH$^+$), measured 483 (MH$^+$). $^1$H NMR (400 MHz, METHANOL-d$_4$) δ 9.04 (dd, J=4.3, 1.6 Hz, 1H), 8.71 (dd, J=8.6, 1.6 Hz, 1H), 8.22 (d, J=7.9 Hz, 1H), 7.72 (dd, J=8.6, 4.3 Hz, 1H), 7.38 (d, J=8.1 Hz, 1H), 7.20 (d, J=8.6 Hz, 2H), 6.75 (d, J=8.6 Hz, 2H), 4.60 (dd, J=11.2, 2.1 Hz, 1H), 4.21 (dd, J=12.9, 3.1 Hz, 1H), 3.60-4.12 (m, 7H), 3.05-3.25 (m, 8H), 2.44 (br t, J=14.7 Hz, 2H), 1.68-1.90 (m, 1H), 1.45 (s, 3H).

Example 21

5-[(4R,8R,9aS)-4-methyl-8-[4-[[(2R)-morpholin-2-yl]methyl]anilino]-1,3,4,6,7,8,9,9a-octahydropyrido[1,2-a]pyrazin-2-yl]quinoline-8-carbonitrile

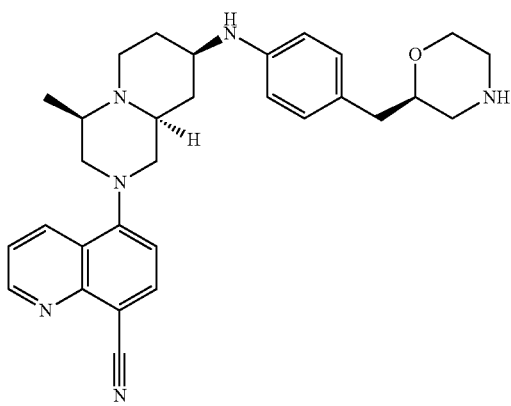 [SMILES: C[C@@H]1CN(c2ccc(C#N)c3ncccc23)C[C@@H]2C[C@H](Nc3ccc(C[C@@H]4CNCCO4)cc3)CCN21]

The title compound was prepared in analogy to preparation of Example 1 by using tert-butyl (2R)-2-[(4-aminophenyl)methyl]morpholine-4-carboxylate instead of tert-butyl 4-(4-(aminomethyl)phenyl)piperazine-1-carboxylate (Compound 1a) in step 1. Example 21 (8 mg) was obtained as a light yellow solid. The stereochemistry was confirmed by NOESY. MS: calc'd 497 (MH$^+$), measured 497 (MH$^+$). $^1$H NMR (400 MHz, METHANOL-d$_4$) δ 9.04 (dd, J=4.2, 1.7 Hz, 1H), 8.71 (dd, J=8.6, 1.7 Hz, 1H), 8.22 (d, J=7.9 Hz, 1H), 7.72 (dd, J=8.6, 4.3 Hz, 1H), 7.38 (d, J=8.1 Hz, 1H), 7.06 (d, J=8.6 Hz, 2H), 6.73 (d, J=8.4 Hz, 2H), 4.07 (br dd, J=13.0, 3.5 Hz, 2H), 3.63-3.99 (m, 7H), 3.03-3.27 (m, 6H), 2.61-2.92 (m, 3H), 2.32-2.54 (m, 2H), 1.68-1.88 (m, 1H), 1.56-1.60 (m, 1H), 1.40 (s, 3H).

Example 22

5-[(4R,8R,9aS)-4-methyl-8-[4-[[(2R)-morpholin-2-yl]methyl]anilino]-1,3,4,6,7,8,9,9a-octahydropyrido[1,2-a]pyrazin-2-yl]-2-deuterio-quinoline-8-carbonitrile

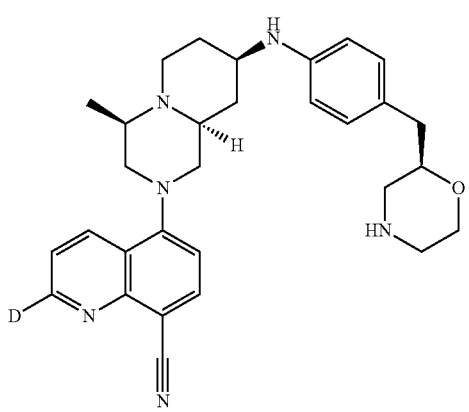 [SMILES: [2H]c1ccc2c(N3C[C@@H]4C[C@H](Nc5ccc(C[C@@H]6CNCCO6)cc5)CCN4[C@H](C)C3)ccc(C#N)c2n1]

The title compound was prepared in analogy to the preparation of Example 1 by using tert-butyl (R)-2-(4-aminobenzyl)morpholine-4-carboxylate and 2-deuterio-5-[(4R)-4-methyl-8-oxo-3,4,6,7,9,9a-hexahydro-1H-pyrido[1,2-a]pyrazin-2-yl]quinoline-8-carbonitrile (Intermediate D1) instead of tert-butyl 4-(4(aminomethyl)phenyl)piperazine-1-carboxylate (Compound 1a) and 5-((4R,9aS)-4-methyl-8-oxooctahydro-2H-pyrido[1,2-a]pyrazin-2-yl)quinoline-8-carbonitrile (Intermediate C1). Example 22 (39 mg) was obtained as a light yellow solid. The stereochemistry was confirmed by NOESY. MS: calc'd 498 (MH$^+$), measured 498 (MH$^+$). $^1$H NMR (400 MHz, METHANOL-d$_4$) δ 8.67 (d, J=8.7 Hz, 1H), 8.17 (d, J=8.1 Hz, 1H), 7.68 (d, J=8.6 Hz, 1H), 7.31 (d, J=7.9 Hz, 1H), 7.04 (d, J=8.4 Hz, 2H), 6.69 (d, J=8.6 Hz, 2H), 4.06 (dd, J=12.8, 3.5 Hz, 1H), 3.88-3.38 (m, 9H), 3.28-3.19 (m, 2H), 3.16-3.01 (m, 3H), 2.87 (dd, J=12.7, 11.1 Hz, 1H), 2.82-2.75 (m, 1H), 2.71-2.63 (m, 1H), 2.39-2.24 (m, 2H), 1.75-1.62 (m, 1H), 1.51-1.43 (m, 1H), 1.40 (d, J=6.4 Hz, 3H).

Example 23

5-[(4R,8R,9aS)-8[6-[(6S)-6-amino-1,4-oxazepan-4-yl]-3-pyridyl]-4-methyl-1,3,4,6,7,8,9,9a-octahydro-pyrido[1,2-a]pyrazin-2-yl]quinoline-8-carbonitrile

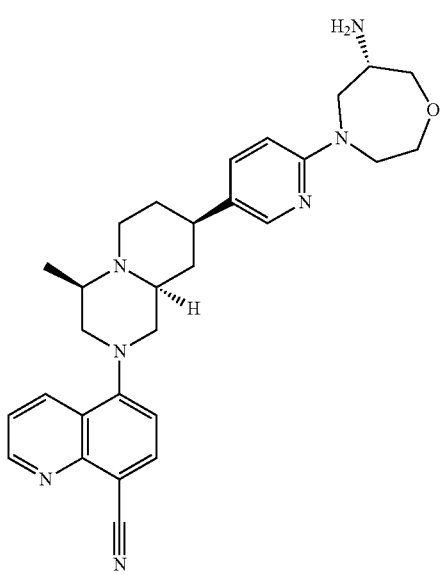 [SMILES: C[C@@H]1CN(c2ccc(C#N)c3ncccc23)C[C@@H]2C[C@H](c3ccc(N4CCOC[C@@H](N)C4)nc3)CCN21]

Example 24 & 27

5-[(4R,8S,9aS)-4-methyl-8-(4-morpholin-2-ylphenyl)-1,3,4,6,7,8,9,9a-octahydropyrido[1,2-a]pyrazin-2-yl]quinoline-8-carbonitrile (Example 24)

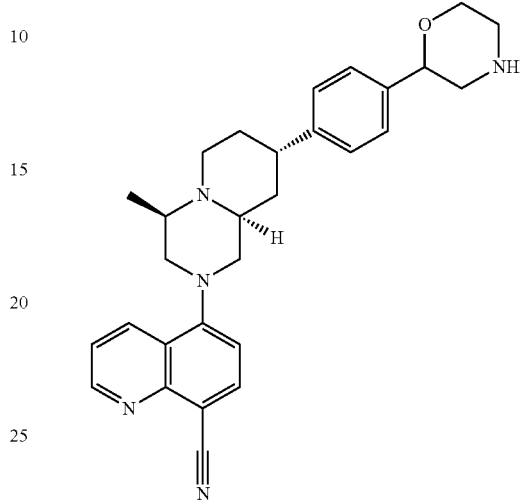

5-[(4R,8R,9aS)-4-methyl-8-[4-[(2R)-morpholin-2-yl]phenyl]-1,3,4,6,7,8,9,9a-octahydropyrido[1,2-a]pyrazin-2-yl]quinoline-8-carbonitrile (Example 27)

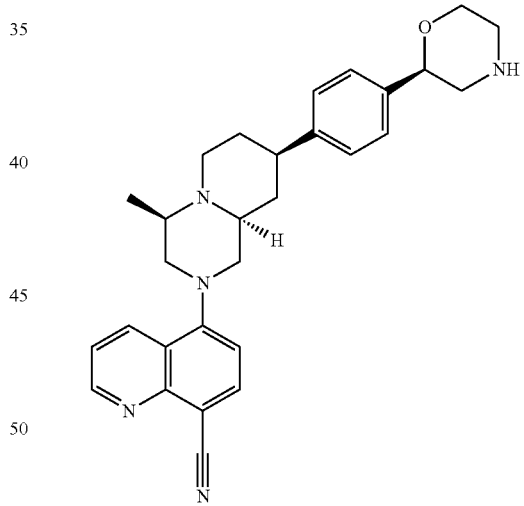

The title compound was prepared in analogy to the preparation of Example 2 by using tert-butyl N-[(6S)-1,4-oxazepan-6-yl]carbamate (PharmaBlock, Catalog #PB97931) instead of tert-butyl piperazine-1-carboxylate (compound 2f). Example 23 (1 mg) was obtained as a light yellow solid. The stereochemistry was confirmed by NOESY. MS: calc'd 498 (MH$^+$), measured 498 (MH$^+$). $^1$H NMR (400 MHz, METHANOL-d$_4$) δ 8.92 (dd, J=4.2, 1.5 Hz, 1H), 8.59 (dd, J=8.6, 1.6 Hz, 1H), 8.10 (d, J=7.9 Hz, 1H), 7.98 (d, J=2.3 Hz, 1H), 7.60 (dd, J=8.6, 4.3 Hz, 1H), 7.51 (dd, J=8.9, 2.5 Hz, 1H), 7.27 (d, J=7.9 Hz, 1H), 6.79 (d, J=8.8 Hz, 1H), 4.17-4.08 (m, 1H), 4.02-3.88 (m, 3H), 3.85-3.52 (m, 10H), 3.17-3.07 (m, 2H), 3.07-2.90 (m, 2H), 2.18-2.05 (m, 2H), 2.02-1.91 (m, 1H), 1.83-1.71 (m, 1H), 1.42 (d, J=6.4 Hz, 3H).

The title compound was prepared in analogy to the preparation of Example 2 by using tert-butyl (R)-2-(4-(4,4,5,5-tetramethyl-1,3,2-dioxaborolan-2-yl)phenyl)morpholine-4-carboxylate instead of 6-bromopyridin-3-yl)boronic acid (compound 2d). Example 24 (11 mg) was obtained as a light yellow solid and Example 27 (17 mg) was obtained as a light yellow solid.

Example 24 The stereochemistry was confirmed by NOESY. MS: calc'd 468 (MH$^+$), measured 468 (MH$^+$). $^1$H NMR (400 MHz, METHANOL-d$_4$) δ 9.03-8.98 (m, 1H), 8.70 (dd, J=8.6, 1.5 Hz, 1H), 8.59 (dd, J=8.6, 1.4 Hz, 1H), 8.73-8.56 (m, 1H), 8.23-8.20 (m, 1H), 8.18 (br d, J=7.9 Hz, 1H), 8.24-8.16 (m, 1H), 7.71-7.63 (m, 1H), 7.58-7.46 (m, 2H), 7.45-7.33 (m, 2H), 4.79 (ddd, J=16.6, 11.3, 2.0 Hz, 1H), 4.26 (dt, J=12.6, 4.2 Hz, 1H), 4.44-4.20 (m, 1H), 4.09-3.63 (m, 5H), 3.60-3.41 (m, 3H), 3.18-3.01 (m, 2H), 2.74-2.60 (m, 1H), 2.51-2.01 (m, 3H), 1.52-1.43 (m, 3H).

Example 27 The stereochemistry was confirmed by NOESY. MS: calc'd 468 (MH$^+$), measured 468 (MH$^+$). $^1$H NMR (400 MHz, METHANOL-d$_4$) δ 9.05-9.01 (m, 1H), 8.71 (dd, J=8.6, 1.5 Hz, 1H), 8.21 (d, J=7.9 Hz, 1H), 7.71 (dd, J=8.6, 4.3 Hz, 1H), 7.45-7.36 (m, 5H), 4.77 (dd, J=11.2, 2.3 Hz, 1H), 4.26 (dd, J=13.0, 3.3 Hz, 1H), 4.15-4.08 (m, 1H), 4.05-3.81 (m, 3H), 3.80-3.65 (m, 2H), 3.46 (br d, J=13.0 Hz, 1H), 3.40-3.35 (m, 1H), 3.31-3.05 (m, 6H), 2.32-2.19 (m, 2H), 2.16-2.02 (m, 1H), 1.93 (q, J=13.1 Hz, 1H), 1.54 (d, J=6.4 Hz, 3H).

Example 25 & 26

5-[(4R,8R,9aS)-4-methyl-8-[4-[[(2R)-morpholin-2-yl]methyl]phenyl]-1,3,4,6,7,8,9,9a-octahydropyrido[1,2-a]pyrazin-2-yl]quinoline-8-carbonitrile (Example 25)

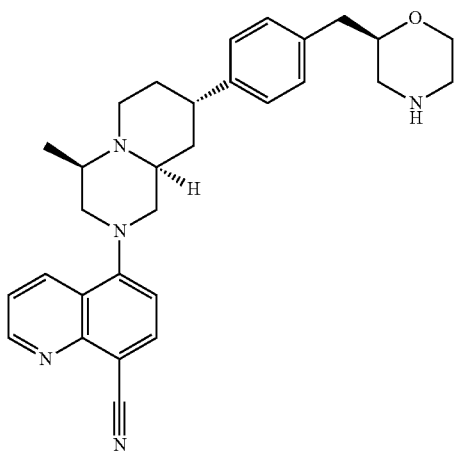 [SMILES: C[C@@H]1CN(c2ccc(C#N)c3ncccc23)C[C@@H]2C[C@@H](c3ccc(C[C@@H]4CNCCO4)cc3)CCN21]

5-[(4R,8S,9aS)-4-methyl-8-[4-(morpholin-2-ylmethyl)phenyl]-1,3,4,6,7,8,9,9a-octahydropyrido[1,2-a]pyrazin-2-yl]quinoline-8-carbonitrile (Example 26)

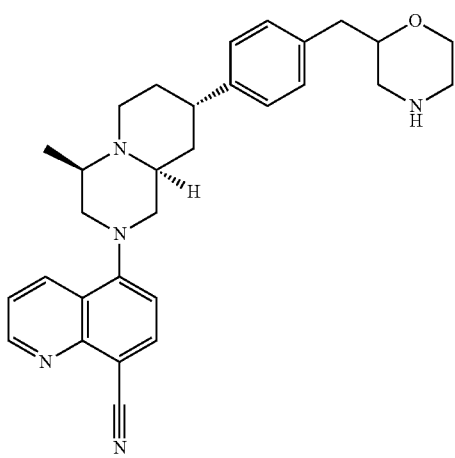 [SMILES: C[C@@H]1CN(c2ccc(C#N)c3ncccc23)C[C@@H]2C[C@@H](c3ccc(CC4CNCCO4)cc3)CCN21]

The title compound was prepared in analogy to the preparation of Example 2 by using tert-butyl (R)-2-(4-(4,4,5,5-tetramethyl-1,3,2-dioxaborolan-2-yl)phenyl)morpholine-4-carboxylate instead of 6-bromopyridin-3-yl)boronic acid (compound 2d). Example 25 (15 mg) was obtained as a light yellow solid and Example 26 (8 mg) was obtained as a light yellow solid.

Example 25: The stereochemistry was confirmed by NOESY. MS: calc'd 482 (MH$^+$), measured 482 (MH$^+$). $^1$H NMR (400 MHz, METHANOL-d$_4$) δ 9.02 (dd, J=4.3, 1.6 Hz, 1H), 8.71 (dd, J=8.6, 1.7 Hz, 1H), 8.20 (d, J=8.1 Hz, 1H), 7.70 (dd, J=8.6, 4.3 Hz, 1H), 7.38 (d, J=8.1 Hz, 1H), 7.27 (s, 4H), 4.14-4.02 (m, 2H), 3.98-3.83 (m, 3H), 3.83-3.64 (m, 3H), 3.29-3.08 (m, 7H), 2.97-2.77 (m, 3H), 2.31-2.17 (m, 2H), 2.15-2.01 (m, 1H), 1.98-1.86 (m, 1H), 1.54 (d, J=6.5 Hz, 3H).

Example 26: The stereochemistry was confirmed by NOESY. MS: calc'd 482 (MH$^+$), measured 482 (MH$^+$). $^1$H NMR (400 MHz, METHANOL-d$_4$) δ 9.04-8.99 (m, 1H), 8.73-8.58 (m, 1H), 8.21 (dd, J=10.1, 8.0 Hz, 1H), 7.68 (ddd, J=13.0, 8.6, 4.3 Hz, 1H), 7.52-7.31 (m, 3H), 7.25 (s, 2H), 4.42-4.20 (m, 1H), 4.10-3.65 (m, 7H), 3.60-3.41 (m, 2H), 3.30-3.22 (m, 2H), 3.18-3.04 (m, 3H), 2.98-2.81 (m, 3H), 2.74-2.59 (m, 1H), 2.48-1.98 (m, 3H), 1.47 (dd, J=14.2, 6.7 Hz, 3H).

Example 28

5-[(4R,8S,9aS)-8-[[6-[(3R,4S)-3-amino-4-methoxypyrrolidin-1-yl]-3-pyridyl]oxy]-4-methyl-1,3,4,6,7,8,9,9a-octahydropyrido[1,2-a]pyrazin-2-yl]quinoline-8-carbonitrile

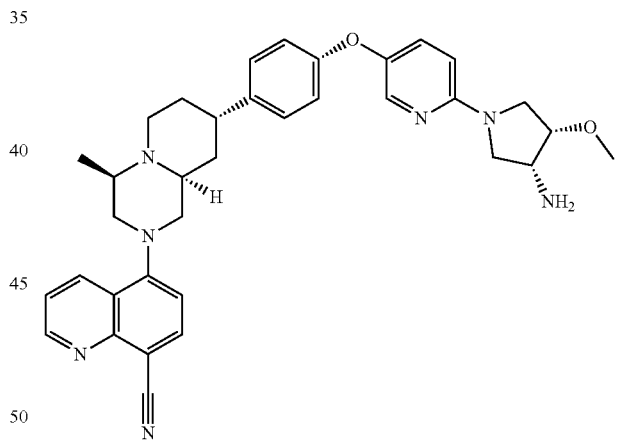

The title compound was prepared in analogy to the preparation of Example 11 by using 2-Chloro-5-hydroxypyridine (CAS: 41288-96-4) and tert-butyl ((3R,4S)-4-methoxypyrrolidin-3-yl)carbamate (CAS: 1932508-77-4, PharmaBlock) instead of 5-chloropyridin-2-ol (compound 11b) and tert-butyl piperazine-1-carboxylate (compound 11d). Example 28 (6 mg) was obtained as a light yellow solid. The stereochemistry was confirmed by NOESY. MS: calc'd 514 (MH$^+$), measured 514 (MH$^+$). $^1$H NMR (400 MHz, METHANOL-d$_4$) δ 8.88 (dd, J=4.2, 1.3 Hz, 1H), 8.57 (dd, J=8.5, 1.3 Hz, 1H), 8.06 (d, J=7.9 Hz, 1H), 7.84 (dd, J=9.7, 2.7 Hz, 1H), 7.79 (d, J=2.7 Hz, 1H), 7.57 (dd, J=8.6, 4.2 Hz, 1H), 7.24 (d, J=7.9 Hz, 1H), 6.99 (d, J=9.7 Hz, 1H), 4.76-4.72 (m, 1H), 4.27-4.20 (m, 1H), 4.09-3.98 (m, 2H), 3.96-3.89 (m, 1H), 3.88-3.74 (m, 3H), 3.71-3.56 (m, 3H), 3.55-3.49 (m, 1H), 3.40 (s, 3H), 3.36-3.26 (m, 1H), 3.19-3.05 (m, 2H), 2.31-2.22 (m, 2H), 2.20-2.06 (m, 1H), 2.05-1.94 (m, 1H), 1.41 (d, J=6.5 Hz, 3H).

Example 29

5-[(4R,8S,9aS)-4-methyl-8-[(5-piperazin-1-yl-3-pyridyl)oxy]-1,3,4,6,7,8,9,9a-octahydropyrido[1,2-a]pyrazin-2-yl]quinoline-8-carbonitrile Example 30

5-[(4R,8R,9aS)-8-[3-[4-[(3R,4R)-3-amino-4-methoxy-pyrrolidin-1-yl]phenyl]azetidin-1-yl]-4-methyl-1,3,4,6,7,8,9,9a-octahydropyrido[1,2-a]pyrazin-2-yl]quinoline-8-carbonitrile

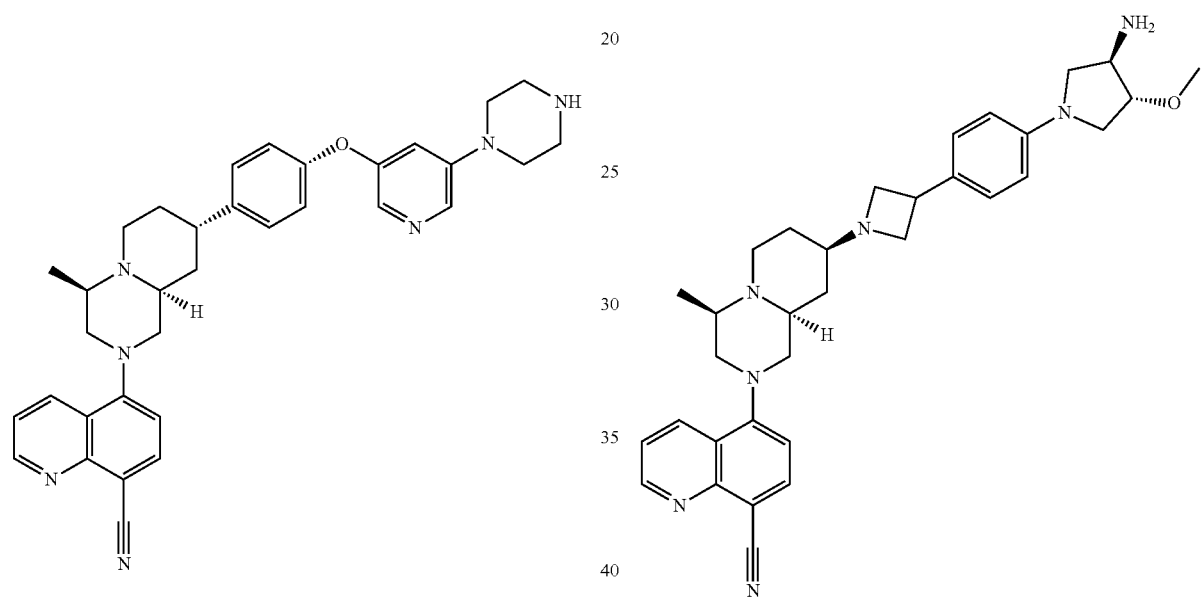

The title compound was prepared in analogy to the preparation of Example 11 by using 3-Bromo-5-hydroxy-pyridine (CAS: 74115-13-2) instead of 5-chloropyridin-2-ol (compound 11b). Example 29 (3 mg) was obtained as a light yellow solid. The stereochemistry was confirmed by NOESY. MS: calc'd 484 (MH$^+$), measured 484 (MH$^+$). $^1$H NMR (400 MHz, METHANOL-d$_4$) δ 9.02 (dd, J=1.6, 4.3 Hz, 1H), 8.70 (dd, J=1.6, 8.6 Hz, 1H), 8.21 (d, J=7.9 Hz, 1H), 8.13 (br d, J=19.7 Hz, 2H), 7.69 (dd, 1H, J=4.3, 8.6 Hz), 7.61 (s, 1H), 7.38 (d, J=7.9 Hz, 1H), 5.14 (br s, 1H), 4.16 (br t, J=11.6 Hz, 1H), 3.9-4.0 (m, 2H), 3.7-3.8 (m, 1H), 3.6-3.7 (m, 5H), 3.4-3.5 (m, 5H), 3.2-3.3 (m, 2H), 2.4-2.5 (m, 2H), 2.2-2.4 (m, 1H), 2.1-2.2 (m, 1H), 1.53 (d, J=6.5 Hz, 3H).

The title compound was prepared in analogy to the preparation of Example 9 by using tert-butyl ((3R,4R)-4-methoxypyrrolidin-3-yl)carbamate (CAS: 1932066-52-8, PharmaBlock) instead of tert-butyl piperazine-1-carboxylate (compound 9c). Example 30 (4 mg) was obtained as a light yellow solid. The stereochemistry was confirmed by NOESY. MS: calc'd 552 (MH$^+$), measured 552 (MH$^+$). $^1$H NMR (400 MHz, METHANOL-d$_4$) δ 8.87 (dd, J=4.3, 1.6 Hz, 1H), 8.51 (dd, J=8.6, 1.6 Hz, 1H), 8.04 (d, J=8.1 Hz, 1H), 7.53 (dd, J=8.6, 4.2 Hz, 1H), 7.01-7.18 (m, 3H), 6.49 (m, 2H), 3.70-3.98 (m, 3H), 3.41-3.66 (m, 4H), 2.99-3.16 (m, 11H), 2.37-2.81 (m, 5H), 1.71-2.04 (m, 3H), 0.90-1.38 ppm (m, 4H).

Example 32

5-[(4R,8R,9aS)-8-[3-[4-[(3R,4S)-3-amino-4-methoxy-pyrrolidin-1-yl]phenyl]azetidin-1-yl]-4-methyl-1,3,4,6,7,8,9,9a-octahydropyrido[1,2-a]pyrazin-2-yl]quinoline-8-carbonitrile

Example 34

5-[(4R,8R,9aS)-4-methyl-8-[4-[[(2S)-morpholin-2-yl]methyl]anilino]-1,3,4,6,7,8,9,9a-octahydropyrido[1,2-a]pyrazin-2-yl]-2-deuterio-quinoline-8-carbonitrile

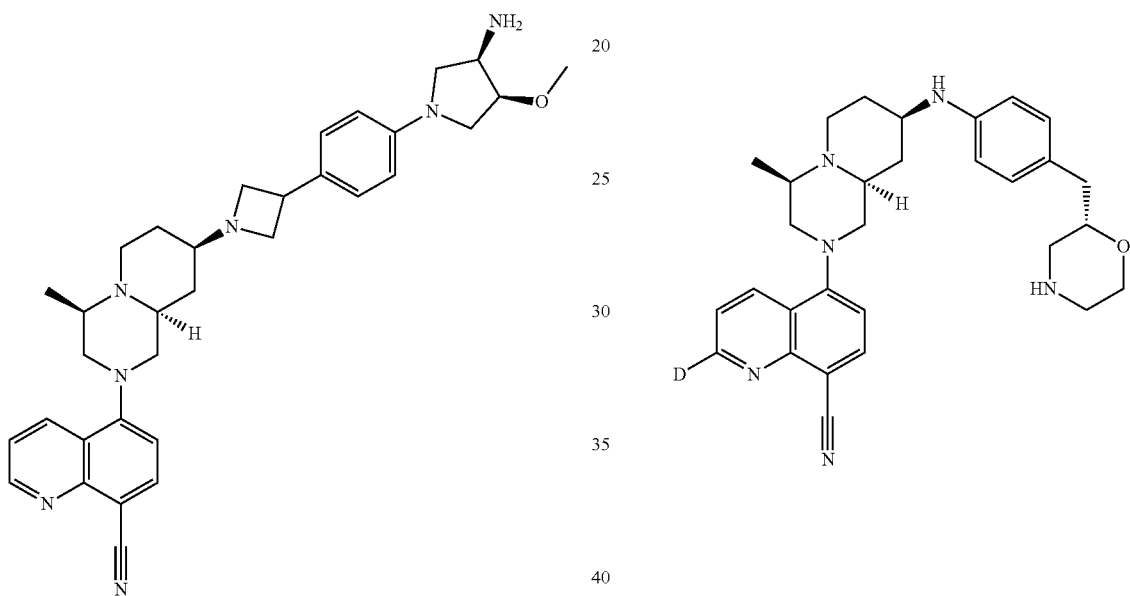

The title compound was prepared in analogy to the preparation of Example 9 by using tert-butyl ((3R,4S)-4-methoxypyrrolidin-3-yl)carbamate instead of tert-butyl piperazine-1-carboxylate (compound 9c). The stereochemistry was confirmed by NOESY. Example 32 (2 mg) was obtained as a light yellow solid. MS: calc' d 552 (MH$^+$), measured 552 (MH$^+$). $^1$H NMR (400 MHz, METHANOL-d$_4$) δ 9.04 (dd, J=4.2, 1.5 Hz, 1H), 8.67 (dd, J=8.6, 1.7 Hz, 1H), 8.22 (d, J=7.9 Hz, 1H), 7.70 (dd, J=8.6, 4.3 Hz, 1H), 7.34 (dd, J=19.0, 8.4 Hz, 3H), 6.68 (d, J=8.7 Hz, 2H), 4.46-4.66 (m, 2H), 4.20-4.39 (m, 3H), 3.94-4.17 (m, 3H), 3.40-3.83 (m, 10H), 3.05-3.25 (m, 3H), 2.78-3.01 (m, 2H), 2.33-2.53 (m, 2H), 1.59-1.99 (m, 2H), 1.46 (s, 3H).

The title compound was prepared in analogy to the preparation of Example 1 by using tert-butyl (S)-2-(4-aminobenzyl)morpholine-4-carboxylate and 2-deuterio-5-[(4R)-4-methyl-8-oxo-3,4,6,7,9,9a-hexahydro-1H-pyrido[1,2-a]pyrazin-2-yl]quinoline-8-carbonitrile (Intermediate D1) instead of tert-butyl 4-(4(aminomethyl)phenyl)piperazine-1-carboxylate (Compound 1a) and 5-((4R,9aS)-4-methyl-8-oxooctahydro-2H-pyrido[1,2-a]pyrazin-2-yl)quinoline-8-carbonitrile (Intermediate C1). Example 34 (34 mg) was obtained as a light yellow solid. The stereochemistry was confirmed by NOESY. MS: calc'd 498 (MH$^+$), measured 498 (MH$^+$). $^1$H NMR (400 MHz, METHANOL-d$_4$) δ 8.58 (d, J=8.6 Hz, 1H), 8.08 (d, J=7.9 Hz, 1H), 7.59 (d, J=8.6 Hz, 1H), 7.25 (d, J=7.9 Hz, 1H), 6.92 (d, J=8.6 Hz, 2H), 6.58 (d, J=8.6 Hz, 2H), 3.98-3.89 (m, 2H), 3.82-3.50 (m, 7H), 3.15-2.95 (m, 6H), 2.78-2.64 (m, 2H), 2.59-2.51 (m, 1H), 2.36-2.23 (m, 2H), 1.72-1.59 (m, 1H), 1.50-1.41 (m, 1H), 1.39 (d, J=6.4 Hz, 3H).

Example 36

5-[(4R,8R,9aS)-8-[3-[4-[(3R,4S)-3-amino-4-methoxy-pyrrolidin-1-yl]phenyl]azetidin-1-yl]-4-methyl-1,3,4,6,7,8,9,9a-octahydropyrido[1,2-a]pyrazin-2-yl]]-2-deuterio-quinoline-8-carbonitrile

Example 37

5-[(4R,8R,9aS)-4-methyl-8-[4-(4-pyridyl)piperazin-1-yl]-1,3,4,6,7,8,9,9a-octahydropyrido[1,2-a]pyrazin-2-yl]-2-deuterio-quinoline-8-carbonitrile

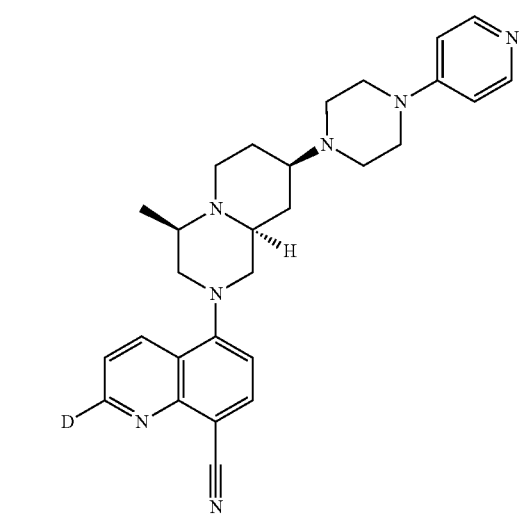 [SMILES: [2H]c1ccc2c(N3C[C@@H]4C[C@H](N5CCN(c6ccncc6)CC5)CCN4[C@H](C)C3)ccc(C#N)c2n1]

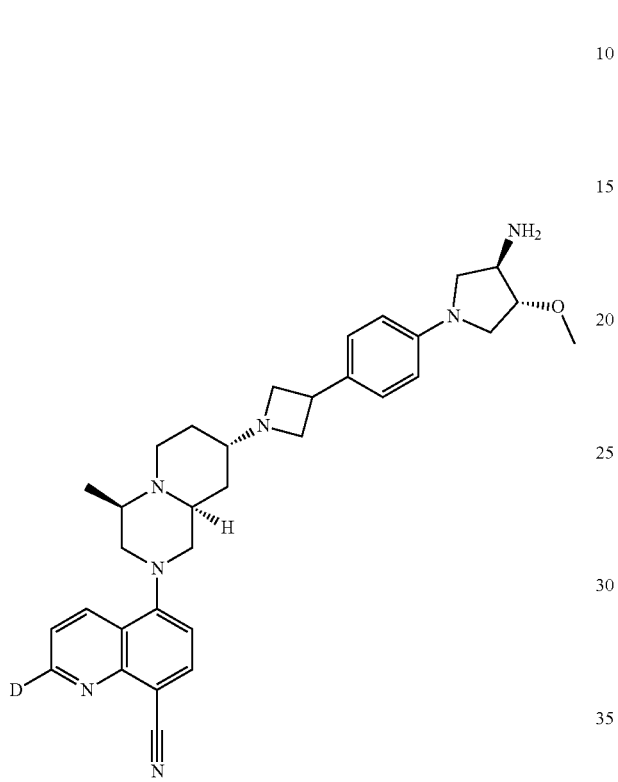

The title compound was prepared in analogy to the preparation of Example 1 by using 1-(pyridin-4-yl)piperazine and 2-deuterio-5-[(4R)-4-methyl-8-oxo-3,4,6,7,9,9a-hexahydro-1H-pyrido[1,2-a]pyrazin-2-yl]quinoline-8-carbonitrile (Intermediate D1) instead of tert-butyl 4-(4-(aminomethyl)phenyl)piperazine-1-carboxylate (Compound 1a) and 5-((4R,9aS)-4-methyl-8-oxooctahydro-2H-pyrido[1,2-a]pyrazin-2-yl)quinoline-8-carbonitrile (Intermediate C1) in step 1. Example 37 (3 mg) was obtained as a light yellow solid. MS: calc'd 469 (MH⁺), measured 469 (MH⁺). ¹H NMR (400 MHz, METHANOL-d₄) δ 8.52 (d, J=8.6 Hz, 1H), 7.96-8.11 (m, 3H), 7.53 (d, J=8.7 Hz, 1H), 7.13 (d, J=8.1 Hz, 1H), 6.66-6.83 (m, 2H), 3.26-3.45 (m, 9H), 2.51-2.80 (m, 7H), 1.74-2.04 (m, 3H), 1.43-1.62 (m, 1H), 1.18-1.35 (m, 1H), 1.09 (d, J=6.2 Hz, 3H).

Example 38

The following tests were carried out in order to determine the activity of the compounds of formula (I) and (Ia) in HEK293-Blue-hTLR-7/8/9 cells assay.

HEK293-Blue-hTLR-7 Cells Assay:

A stable HEK293-Blue-hTLR-7 cell line was purchased from InvivoGen (Cat. #: hkb-htlr7, San Diego, California, USA). These cells were originally designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore the reporter expression was declined by TLR7 antagonist under the stimulation of a ligand, such as R848 (Resiquimod), for incubation of 20 hrs. The cell culture supernatant SEAP reporter activity was determined using QUANTI-Blue™ kit (Cat. #: rep-qb1, Invivogen, San Diego, Ca, USA) at a wavelength of 640 nm, a detection medium that turns purple or blue in the presence of alkaline phosphatase.

The title compound was prepared in analogy to the preparation of Example 9 by using 2-deuterio-5-[(4R)-4-methyl-8-oxo-3,4,6,7,9,9a-hexahydro-1H-pyrido[1,2-a]pyrazin-2-yl]quinoline-8-carbonitrile (Intermediate D1) and tert-butyl N-[(3R,4S)-4-methoxypyrrolidin-3-yl]carbamate (CAS: 1932508-77-4, PharmaBlock) instead of 5-((4R,9aS)-4-methyl-8-oxooctahydro-2H-pyrido[1,2-a]pyrazin-2-yl)quinoline-8-carbonitrile (Intermediate C1) and tert-butyl piperazine-1-carboxylate (compound 9c). Example 36 (7 mg) was obtained as a light yellow solid. MS: calc'd 553 (MH⁺), measured 553 (MH⁺). ¹H NMR (400 MHz, METHANOL-d₄) δ 8.56 (d, J=8.7 Hz, 1H), 8.10 (d, J=7.9 Hz, 1H), 7.59 (d, J=8.6 Hz, 1H), 7.23 (dd, J=18.5, 8.3 Hz, 3H), 6.61 (d, J=8.8 Hz, 2H), 4.48-4.38 (m, 2H), 4.25-4.14 (m, 2H), 4.04-3.94 (m, 3H), 3.82-3.73 (m, 2H), 3.70-3.63 (m, 1H), 3.62-3.52 (m, 5H), 3.38-3.36 (m, 3H), 3.35-3.31 (m, 1H), 3.18-3.01 (m, 3H), 2.95-2.84 (m, 1H), 2.40-2.27 (m, 2H), 1.84-1.72 (m, 1H), 1.67-1.56 (m, 1H), 1.36 (d, J=6.2 Hz, 3H).

HEK293-Blue-hTLR7 cells were incubated at a density of 250,000~450,000 cells/mL in a volume of 170 µL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 µL test compound in a serial dilution in the presence of final DMSO at 1% and 10 µL of 20 uM R848 in above DMEM, perform incubation under 37° C. in a CO$_2$ incubator for 20 hrs. Then 20 µL of the supernatant from each well was incubated with 180 µL Quanti-blue substrate solution at 37° C. for 2 hrs and the absorbance was read at 620~655 nm using a spectrophotometer. The signaling pathway that TLR7 activation leads to downstream NF-κB activation has been widely accepted, and therefore similar reporter assay was modified for evaluating TLR7 antagonist.

HEK293-Blue-hTLR-8 Cells Assay:

A stable HEK293-Blue-hTLR-8 cell line was purchased from InvivoGen (Cat. #: hkb-htlr8, San Diego, California, USA). These cells were originally designed for studying the stimulation of human TLR8 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR8 cells with TLR8 ligands. Therefore the reporter expression was declined by TLR8 antagonist under the stimulation of a ligand, such as R848, for incubation of 20 hrs. The cell culture supernatant SEAP reporter activity was determined using QUANTI-Blue™ kit (Cat. #: rep-qb1, Invivogen, San Diego, Ca, USA) at a wavelength of 640 nm, a detection medium that turns purple or blue in the presence of alkaline phosphatase.

HEK293-Blue-hTLR8 cells were incubated at a density of 250,000~450,000 cells/mL in a volume of 170 µL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 µL test compound in a serial dilution in the presence of final DMSO at 1% and 10 µL of 60 uM R848 in above DMEM, perform incubation under 37° C. in a CO$_2$ incubator for 20 hrs. Then 20 µL of the supernatant from each well was incubated with 180 µL Quanti-blue substrate solution at 37° C. for 2 hrs and the absorbance was read at 620~655 nm using a spectrophotometer. The signaling pathway that TLR8 activation leads to downstream NF-κB activation has been widely accepted, and therefore similar reporter assay was modified for evaluating TLR8 antagonist.

HEK293-Blue-hTLR-9 Cells Assay:

A stable HEK293-Blue-hTLR-9 cell line was purchased from InvivoGen (Cat. #: hkb-htlr9, San Diego, California, USA). These cells were originally designed for studying the stimulation of human TLR9 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR9 cells with TLR9 ligands. Therefore the reporter expression was declined by TLR9 antagonist under the stimulation of a ligand, such as ODN2006 (Cat. #: tlrl-2006-1, Invivogen, San Diego, California, USA), for incubation of 20 hrs. The cell culture supernatant SEAP reporter activity was determined using QUANTI-Blue™ kit (Cat. #: rep-qb1, Invivogen, San Diego, California, USA) at a wavelength of 640 nm, a detection medium that turns purple or blue in the presence of alkaline phosphatase.

HEK293-Blue-hTLR9 cells were incubated at a density of 250,000~450,000 cells/mL in a volume of 170 µL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 µL test compound in a serial dilution in the presence of final DMSO at 1% and 10 µL of 20 uM ODN2006 in above DMEM, perform incubation under 37° C. in a CO$_2$ incubator for 20 hrs. Then 20 µL of the supernatant from each well was incubated with 180 µL Quanti-blue substrate solution at 37° C. for 2 h and the absorbance was read at 620~655 nm using a spectrophotometer. The signaling pathway that TLR9 activation leads to downstream NF-κB activation has been widely accepted, and therefore similar reporter assay was modified for evaluating TLR9 antagonist.

The compounds of formula (I) have human TLR7 and/or TLR8 inhibitory activities (IC$_{50}$ value) <0.5 µM. Moreover, some compounds also have human TLR9 inhibitory activity <0.5 µM. Activity data of the compounds of the present invention were shown in Table 2.

TABLE 2

The activity of the compounds of present invention in HEK293-Blue-hTLR-7/8/9 cells assays

| Example No | HEK/hTLR7 IC$_{50}$ (µM) | HEK/hTLR8 IC$_{50}$ (µM) | HEK/hTLR9 IC$_{50}$ (µM) |
|---|---|---|---|
| 1 | 0.033 | 0.067 | <0.032 |
| 2 | 0.004 | 0.019 | 0.081 |
| 3 | 0.010 | 0.023 | 0.092 |
| 4 | 0.006 | 0.018 | 0.086 |
| 6 | 0.041 | 0.047 | 0.087 |
| 7 | 0.032 | 0.125 | 0.184 |
| 9 | 0.027 | 0.036 | <0.032 |
| 11 | 0.046 | 0.015 | 0.090 |
| 12 | 0.017 | 0.045 | 0.066 |
| 13 | 0.021 | 0.046 | 0.094 |
| 14 | 0.023 | 0.048 | 0.078 |
| 15 | 0.024 | 0.080 | 0.084 |
| 16 | 0.035 | 0.008 | 0.037 |
| 17 | 0.035 | 0.054 | <0.032 |
| 18 | 0.021 | 0.006 | 0.060 |
| 19 | 0.015 | 0.063 | 0.082 |
| 20 | 0.013 | 0.050 | 0.050 |
| 21 | 0.020 | 0.054 | 0.086 |
| 22 | 0.044 | 0.049 | 0.084 |
| 23 | 0.021 | 0.079 | 0.075 |
| 24 | 0.004 | 0.014 | 0.082 |
| 25 | 0.008 | 0.030 | 0.078 |
| 26 | 0.030 | 0.027 | 0.095 |
| 27 | 0.004 | 0.018 | 0.072 |
| 28 | 0.047 | 0.007 | 0.044 |
| 29 | 0.049 | 0.005 | 0.089 |
| 30 | 0.041 | 0.069 | 0.078 |
| 32 | 0.048 | 0.029 | 0.033 |
| 34 | 0.047 | 0.040 | 0.057 |
| 36 | 0.030 | 0.018 | 0.032 |
| 37 | 0.011 | 0.116 | 0.034 |

Example 39 hERG Channel Inhibition Assay:

The hERG channel inhibition assay is a highly sensitive measurement that identifies compounds exhibiting hERG inhibition related to cardiotoxicity in vivo. The hERG K$^+$ channels were cloned in humans and stably expressed in a CHO (Chinese hamster ovary) cell line. CHO$_{hERG}$ cells were used for patch-clamp (voltage-clamp, whole-cell) experiments. Cells were stimulated by a voltage pattern to activate hERG channels and conduct I$_{KhERG}$ currents (rapid delayed outward rectifier potassium current of the hERG channel). After the cells were stabilized for a few minutes, the amplitude and kinetics of I$_{KhERG}$ were recorded at a stimulation frequency of 0.1 Hz, (6 bpm). Thereafter, the test compound was added to the preparation at increasing concentrations. For each concentration, an attempt was made to reach a steady-state effect, usually, this was achieved within 3-10 min at which time the next highest concentration was applied. The amplitude and kinetics of I$_{KhERG}$ are recorded in each concentration of the drug which were compared to the control values (taken as 100%). (references: Redfern W S, Carlsson L, Davis A S, Lynch W G, MacKenzie I, Palethorpe S, Siegl P K, Strang I, Sullivan A T, Wallis R, Camm A J, Hammond T G. 2003; Relationships between preclinical cardiac electrophysiology, clinical QT interval prolongation and torsade de pointes for a broad range of drugs: evidence for a provisional safety margin in drug development. Cardiovasc. Res. 58:32-45, Sanguinetti MC, Tristani-Firouzi M. 2006; hERG potassium channels and cardiac arrhythmia. Nature 440:463-469, Webster R, Leishman D, Walker D. 2002; Towards a drug concentration effect relationship for QT prolongation and torsades de pointes. Curr. Opin. Drug Discov. Devel. 5:116-26).

Results of hERG are given in Table 3. A safety ratio (hERG IC$_{20}$/EC$_{50}$)>30 suggests a sufficient window to differentiate the pharmacology by inhibiting TLR7/8/9 pathways from the potential hERG related cardiotoxicity. According to the calculation of hERG IC$_{20}$/TLR7/8/9 IC$_{50}$ below which serves as early selectivity index to assess hERG liability, obviously reference compounds ER-887258, ER-888285, ER-888286, R1 and R2 have much narrower safety window compared to the compounds of this invention.

TABLE 3 hERG and safety ratio results

| Example No | hERG IC$_{20}$ (μM) | hERG IC$_{50}$ (μM) | hERG IC$_{20}$/ TLR7 IC$_{50}$ | hERG IC$_{20}$/ TLR8 IC$_{50}$ | hERG IC$_{20}$/ TLR9 IC$_{50}$ |
|---|---|---|---|---|---|
| 6 | 9.2 | >20 | 224.4 | 195.7 | 105.7 |
| 9 | >10 | >20 | >370.4 | >277.8 | >312.5 |
| 11 | >10 | >20 | >217.4 | >666.6 | >111.1 |
| 20 | >10 | >20 | >769.2 | >200 | >200 |
| 21 | >10 | >20 | >500 | >185.2 | >116.3 |
| 34 | >10 | >20 | >212.7 | >250 | >175.4 |

Example 40

The compounds would be desirable to have minimal DDI liabilities. Therefore, the effects of compounds of formula (I) of (Ia) on major CYP isoforms, e.g. CYP2C9, CYP2D6 and CYP3A4, are determined.

CYP Inhibition Assay

This is a high throughput screening assay used for assessment of reversible inhibition of CYP2C9, CYP2D6, and CYP3A4 activity of test compounds in human liver microsome (HLM) in early discovery stage.

TABLE 4

Chemicals and materials used in the CYP inhibition assay

| Substances | Description | Source | Cat. No. | Final Concentration in incubation |
|---|---|---|---|---|
| Human Liver Microsomes | | BD-Gentest | 452117 | 0.2 mg/mL |
| Diclofenac | CYP2C9 substrate | Sigma | D-6899 | 5 μM |
| 4'-Hydroxydiclofenac | CYP2C9 product | | | |
| 4'-OH-Diclofenac-13C6 | CYP2C9 internal standard | Becton Dickinson | 451006 | |
| Dextromethorphan | CYP2D6 substrate | Sigma | D-2531 | 5 μM |
| Dextrorphan | CYP2D6 product | | | |
| Dextrorphan-D3 | CYP2D6 internal standard | Promochem | CERD-041 | |
| Midazolam | CYP3A4 substrate | Roche | | 5 μM |
| 1'-Hydroxymidazolam | CYP3A4 product | | | |
| 1'-OH Midazolam-D4 | CYP3A4 internal standard | Roche | | |
| Sulfaphenazole | CYP2C9 inhibitor | | | 2 μM |
| Quinidine | CYP2D6 inhibitor | | | 0.5 μM |
| Ketoconazole | CYP3A4 inhibitor | | | 0.5 μM |

Procedure 10 mM DMSO stock solutions of test compounds were diluted in DMSO to generate 2 mM intermediate stock solution. 250 nL of intermediate stock solution were transferred in duplicate into 3 separate 384 well microtitre plates (assay-ready plates). A mixture of HLM and each substrate was made up. 45 μL of HLM substrate mix was then transferred to each well of an assay ready plate and mixed. The negative (solvent) and positive controls (standard inhibitor for each CYP) were included in each assay ready plate. The assay ready plate was warmed to 37° C. in an incubator over 10 minutes. 5 μL pre-warmed NADPH regenerating system was added to each incubation well to start the reaction. Final incubation volume was 50 μL. The assay plate then was placed back in the 37° C. incubator. After incubation (10 minutes for CYP2D6) for 5 minutes, incubates were quenched by addition of 50 μL 100% acetonitrile containing internal standards (400 ng/mL 13C6-4'-OH-Diclofenac, 20 ng/mL D3-Dextrorphan and 20 ng/mL D4-1'OH-Midazolam). The supernatants were collected for RapidFire/MS/MS analysis.

RapidFire online solid phase extraction/sample injection system (Agilent) coupled with API4000 triple quadrupole mass spectrometer (AB Sciex) were used for sample analysis. The mobile phase composed of acetonitrile and water supplemented with 0.1% formic acid. A C4 solid phase extraction cartridge is used for sample separation. MS detection is achieved in positive ion MRM mode.

Data Analysis

Peak areas for substrate, metabolite and internal standard are determined using the RapidFire integrator software (version 3.6.12009.12296). Peak area ratios (PAR) of metabolite and internal standard (stable-labelled metabolite) are then calculated. The measurement window for each experiment is then defined:

PAR (0% activity)=average PAR for all incubations containing concentrated inhibitor;
Par (100% activity)=average PAR for all incubations containing no inhibitor (DMSO controls);
% Activity (test inhibitor)=[PAR(test inhibitor)−PAR(0% activity)/PAR(100% activity)−PAR(0% activity)];
% Inhibition (test inhibitor)=100−% Activity (test inhibitor).

The compounds of present invention were found to have low CYP inhibition for CYP2D6 determined in the assays described above.

TABLE 5

CYP inhibition of the compounds of this invention for CYP2D6

| Example No | CYP (%) 2C9/2D6/3A4 |
|---|---|
| 2 | 6/−5.5/38 |
| 6 | −8/−12.5/11 |
| 9 | −6.5/−2/9.5 |
| 11 | 0/−24.5/12 |
| 12 | 14.5/0/37.5 |
| 14 | −1/−0.5/19.5 |
| 19 | −3.5/−6/30 |
| 21 | 3/9/15.5 |
| 27 | 4/8/37 |
| 34 | −20/2.5/3.5 |
| 37 | 4.5/14.5/32.5 | percentage inhibition < 0: not or weak inhibitor

The invention claimed is:

1. A compound of formula (I),

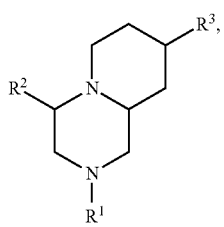

(I)

wherein

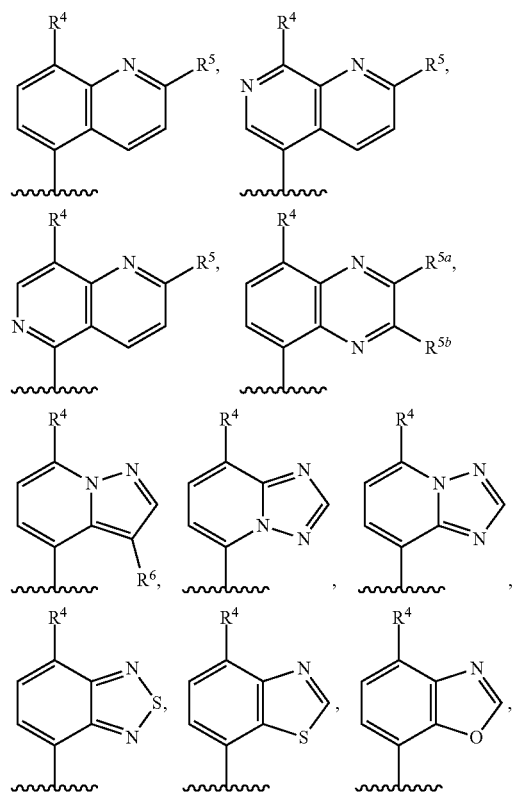

$R^1$ is wherein R4 is $C_{1-6}$alkyl, $C_{1-6}$alkoxy, halo$C_{1-6}$alkyl, halogen, nitro or cyano; $R^{4a}$ is $C_{1-6}$alkyl or $C_{3-7}$cycloalkyl; $R^5$, $R^{5a}$ and $R^{5b}$ are independently selected from H and deuterium; and $R^6$ is H or halogen;

$R^2$ is $C_{1-6}$alkyl; and $R^3$ is ((amino ($C_{1-6}$alkoxy) pyrrolidinyl) phenyl) azetidinyl, (amino ($C_{1-6}$alkoxy) pyrrolidinyl) pyridinyl, (amino($C_{1-6}$alkoxy) pyrrolidinyl) pyridinyloxy, (amino-1,4-oxazepanyl) pyridinyl, (aminoazetidinyl) pyridinyl, (morpholinyl$C_{1-6}$alkyl) phenyl, (morpholinyl$C_{1-6}$alkyl) phenylamino, (piperazinylphenyl) azetidinyl, (piperazinylphenyl) $C_{1-6}$alkylamino, aminohalopyrrolidinyl, morpholinylphenyl, morpholinylphenylamino, piperazinylphenyl, piperazinylpyridinyl, piperazinylpyridinyloxy, piperazinylpyrimidinyloxy or pyridinylpiperazinyl;

or a pharmaceutically acceptable salt thereof.

2. A compound according to claim 1, or a pharmaceutically acceptable salt thereof, wherein
R¹ is wherein R⁴ is cyano; and R⁵ is H or deuterium.

3. A compound according to claim 2, or a pharmaceutically acceptable salt thereof, wherein R³ is:
((3-amino-4-methoxy-pyrrolidin-1-yl) phenyl) azetidin-1-yl;
(3-amino-4-methoxy-pyrrolidin-1-yl)-3-pyridinyl;
(3-amino-4-methoxy-pyrrolidin-1-yl)-3-pyridinyloxy;
(3-aminoazetidin-1-yl)-3-pyridinyl;
(4-morpholin-2-ylmethyl) phenyl;
(4-morpholin-2-ylmethyl) phenylamino;
(4-piperazin-1-ylphenyl) azetidin-1-yl;
(4-piperazin-1-ylphenyl)methylamino;
(6-amino-1,4-oxazepan-4-yl)-3-pyridinyl;
2-piperazin-1-ylpyrimidin-5-yloxy;
3-amino-4-fluoro-pyrrolidin-1-yl;
4-morpholin-2-ylphenyl;
4-morpholin-2-ylphenylamino;
4-piperazin-1-ylphenyl;
4-pyridinylpiperazin-1-yl;
5-piperazin-1-yl-2-pyridinyloxy;
5-piperazin-1-yl-3-pyridinyloxy;
6-piperazin-1-yl-3-pyridinyl; or
6-piperazin-1-yl-3-pyridinyloxy.

4. A compound according to claim 1, wherein R² is methyl.

5. A compound according to claim 2, or a pharmaceutically acceptable salt thereof, wherein R³ is:
(morpholinylC₁₋₆alkyl) phenylamino,
(piperazinylphenyl) azetidinyl,
morpholinylphenyl,
morpholinylphenylamino,
piperazinylpyridinyloxy; or
piperazinylpyrimidinyloxy.

6. A compound according to claim 2, or a pharmaceutically acceptable salt thereof wherein R³ is:
(4-morpholin-2-ylmethyl) phenylamino,
(4-piperazin-1-ylphenyl) azetidin-1-yl,
4-morpholin-2-ylphenyl,
4-morpholin-2-ylphenylamino,
6-piperazin-1-yl-3-pyridinyloxy, or
2-piperazin-1-ylpyrimidin-5-yloxy.

7. A compound according to claim 2, wherein
R² is methyl; and
R³ is:
(4-morpholin-2-ylmethyl) phenylamino,
(4-piperazin-1-ylphenyl) azetidin-1-yl,
4-morpholin-2-ylphenyl,
4-morpholin-2-ylphenylamino,
6-piperazin-1-yl-3-pyridinyloxy; or
2-piperazin-1-ylpyrimidin-5-yloxy;
or a pharmaceutically acceptable salt thereof.

8. A compound selected from:
5-[(4R,8R,9aS)-4-methyl-8-[(4-piperazin-1-ylphenyl) methylamino]-1,3,4,6,7,8,9,9a-octahydropyrido [1,2-a] pyrazin-2-yl]quinoline-8-carbonitrile;
5-[(4R,8S,9aS)-4-methyl-8-[(4-piperazin-1-ylphenyl) methylamino]-1,3,4,6,7,8,9,9a-octahydropyrido [1,2-a] pyrazin-2-yl]quinoline-8-carbonitrile;
5-[(4R,8R)-4-methyl-8-(6-piperazin-1-yl-3-pyridyl)-1,3, 4,6,7,8,9,9a-octahydropyrido [1,2-a]pyrazin-2-yl]quinoline-8-carbonitrile;
5-[(4R,8R)-4-methyl-8-(4-piperazin-1-ylphenyl)-1,3,4,6, 7,8,9,9a-octahydropyrido [1,2-a]pyrazin-2-yl]quinoline-8-carbonitrile;
5-[(4R,8R,9aS)-4-methyl-8-(6-piperazin-1-yl-3-pyridyl)-1,3,4,6,7,8,9,9a-octahydropyrido [1,2-a]pyrazin-2-yl] quinoline-8-carbonitrile;
5-[(4R,8R,9aS)-8-[6-[(3S,4S)-3-amino-4-methoxy-pyrrolidin-1-yl]-3-pyridyl]-4-methyl-1,3,4,6,7,8,9,9a-octahydropyrido [1,2-a]pyrazin-2-yl]quinoline-8-carbonitrile;
5-[(4R,8R,9aS)-8-[6-(3-aminoazetidin-1-yl)-3-pyridyl]-4-methyl-1,3,4,6,7,8,9,9a-octahydropyrido [1,2-a] pyrazin-2-yl]quinoline-8-carbonitrile;
5-[(4R,8R,9aS)-4-methyl-8-[3-(4-piperazin-1-ylphenyl) azetidin-1-yl]-1,3,4,6,7,8,9,9a-octahydropyrido [1,2-a] pyrazin-2-yl]quinoline-8-carbonitrile;
5-[(4R,8S,9aS)-4-methyl-8-[(5-piperazin-1-yl-2-pyridyl) oxy]-1,3,4,6,7,8,9,9a-octahydropyrido [1,2-a]pyrazin-2-yl]quinoline-8-carbonitrile;
5-[(4R,8R,9aS)-8-[6-[(3R,4S)-3-amino-4-methoxy-pyrrolidin-1-yl]-3-pyridyl]-4-methyl-1,3,4,6,7,8,9,9a-octahydropyrido [1,2-a]pyrazin-2-yl]quinoline-8-carbonitrile;
5-[(4R,8R,9aS)-8-[6-[(3S,4R)-3-amino-4-methoxy-pyrrolidin-1-yl]-3-pyridyl]-4-methyl-1,3,4,6,7,8,9,9a-octahydropyrido [1,2-a]pyrazin-2-yl]quinoline-8-carbonitrile;
5-[(4R,8R,9aS)-8-[6-[(3R,4R)-3-amino-4-methoxy-pyrrolidin-1-yl]-3-pyridyl]-4-methyl-1,3,4,6,7,8,9,9a-octahydropyrido [1,2-a]pyrazin-2-yl]quinoline-8-carbonitrile;
5-[(4R,8R,9aR)-4-methyl-8-(6-piperazin-1-yl-3-pyridyl)-1,3,4,6,7,8,9,9a-octahydropyrido [1,2-a]pyrazin-2-yl] quinoline-8-carbonitrile;
5-[(4R,8S,9aS)-4-methyl-8-[(6-piperazin-1-yl-3-pyridyl) oxy]-1,3,4,6,7,8,9,9a-octahydropyrido [1,2-a]pyrazin-2-yl]quinoline-8-carbonitrile;
5-[(4R,8S,9aS)-4-methyl-8-(2-piperazin-1-ylpyrimidin-5-yl) oxy-1,3,4,6,7,8,9,9a-octahydropyrido [1,2-a] pyrazin-2-yl]quinoline-8-carbonitrile;
5-[(4R,8R,9aS)-8-[6-[(3R,4S)-3-amino-4-fluoro-pyrrolidin-1-yl]-3-pyridyl]-4-methyl-1,3,4,6,7,8,9,9a-octahydropyrido [1,2-a]pyrazin-2-yl]quinoline-8-carbonitrile;
5-[(4R,8R,9aS)-4-methyl-8-[4-[(2S)-morpholin-2-yl]anilino]-1,3,4,6,7,8,9,9a-octahydropyrido [1,2-a]pyrazin-2-yl]quinoline-8-carbonitrile;
5-[(4R,8R,9aS)-4-methyl-8-[4-[[(2R)-morpholin-2-yl] methyl]anilino]-1,3,4,6,7,8,9,9a-octahydropyrido [1,2-a]pyrazin-2-yl]quinoline-8-carbonitrile;
5-[(4R,8R,9aS)-4-methyl-8-[4-[[(2R)-morpholin-2-yl] methyl]anilino]-1,3,4,6,7,8,9,9a-octahydropyrido [1,2-a]pyrazin-2-yl]-2-deuterio-quinoline-8-carbonitrile5-[(4R,8R,9aS)-4-methyl-8-[4-[[(2R)-morpholin-2-yl] methyl]anilino]-1,3,4,6,7,8,9,9a-octahydropyrido [1,2-a]pyrazin-2-yl]-2-deuterio-quinoline-8-carbonitrile;

5-[(4R,8R,9aS)-8-[6-[(6S)-6-amino-1,4-oxazepan-4-yl]-3-pyridyl]-4-methyl-1,3,4,6,7,8,9,9a-octahydropyrido[1,2-a]pyrazin-2-yl]quinoline-8-carbonitrile;

5-[(4R,8S,9aS)-4-methyl-8-(4-morpholin-2-ylphenyl)-1,3,4,6,7,8,9,9a-octahydropyrido [1,2-a]pyrazin-2-yl]quinoline-8-carbonitrile;

5-[(4R,8R,9aS)-4-methyl-8-[4-[(2R)-morpholin-2-yl]phenyl]-1,3,4,6,7,8,9,9a-octahydropyrido [1,2-a]pyrazin-2-yl]quinoline-8-carbonitrile;

5-[(4R,8R,9aS)-4-methyl-8-[4-[[(2R)-morpholin-2-yl]methyl]phenyl]-1,3,4,6,7,8,9,9a-octahydropyrido [1,2-a]pyrazin-2-yl]quinoline-8-carbonitrile;

5-[(4R,8S,9aS)-4-methyl-8-[4-(morpholin-2-ylmethyl)phenyl]-1,3,4,6,7,8,9,9a-octahydropyrido [1,2-a]pyrazin-2-yl]quinoline-8-carbonitrile;

5-[(4R,8S,9aS)-8-[[6-[(3R,4S)-3-amino-4-methoxy-pyrrolidin-1-yl]-3-pyridyl]oxy]-4-methyl-1,3,4,6,7,8,9,9a-octahydropyrido [1,2-a]pyrazin-2-yl]quinoline-8-carbonitrile;

5-[(4R,8S,9aS)-4-methyl-8-[(5-piperazin-1-yl-3-pyridyl)oxy]-1,3,4,6,7,8,9,9a-octahydropyrido [1,2-a]pyrazin-2-yl]quinoline-8-carbonitrile;

5-[(4R,8R,9aS)-8-[3-[4-[(3R,4R)-3-amino-4-methoxy-pyrrolidin-1-yl]phenyl]azetidin-1-yl]-4-methyl-1,3,4,6,7,8,9,9a-octahydropyrido [1,2-a]pyrazin-2-yl]quinoline-8-carbonitrile;

5-[(4R,8R,9aS)-8-[3-[4-[(3R,4S)-3-amino-4-methoxy-pyrrolidin-1-yl]phenyl]azetidin-1-yl]-4-methyl-1,3,4,6,7,8,9,9a-octahydropyrido [1,2-a]pyrazin-2-yl]quinoline-8-carbonitrile;

5-[(4R,8R,9aS)-4-methyl-8-[4-[(2S)-morpholin-2-yl]methyl]anilino]-1,3,4,6,7,8,9,9a-octahydropyrido [1,2-a]pyrazin-2-yl]-2-deuterio-quinoline-8-carbonitrile;

5-[(4R,8R,9aS)-8-[3-[4-[(3R,4S)-3-amino-4-methoxy-pyrrolidin-1-yl]phenyl]azetidin-1-yl]-4-methyl-1,3,4,6,7,8,9,9a-octahydropyrido [1,2-a]pyrazin-2-yl]]-2-deuterio-quinoline-8-carbonitrile; and 5-[(4R,8R,9aS)-4-methyl-8-[4-(4-pyridyl) piperazin-1-yl]-1,3,4,6,7,8,9,9a-octahydropyrido [1,2-a]pyrazin-2-yl]-2-deuterio-quinoline-8-carbonitrile;

or a pharmaceutically acceptable salt thereof.

9. A process for the preparation of a compound according to claim 1, comprising any one of the following steps:

a) Buchwald-Hartwig amination reaction between a compound of formula (VIII),

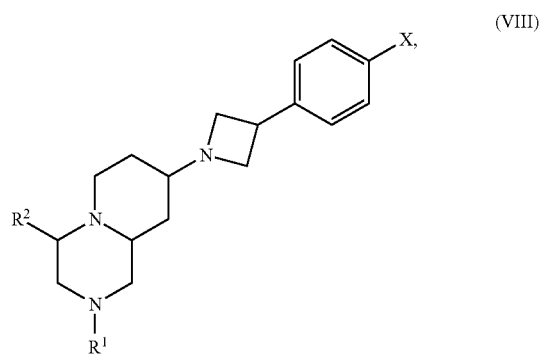

(VIII)

and amine (V),

(V)

b) reductive amination of a compound of formula (IV),

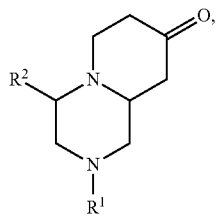

(IV)

with amine (V),

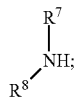

(V)

c) Buchwald-Hartwig amination reaction between a compound of formula (XIV),

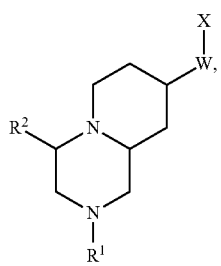

(XIV)

and amine (V),

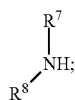

(V)

d) Buchwald-Hartwig amination reaction between a compound of formula (XVIII),

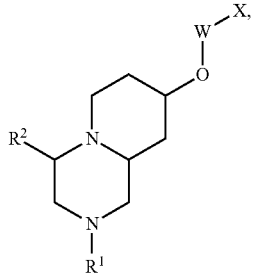
(XVIII)

and amine (V),

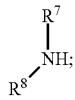
(V)

wherein:
X is halogen;
$R^7$ is H;
$R^8$ is heterocyclylheteroaryl, heterocyclylC$_{1-6}$alkylheteroaryl, heterocyclylheteroarylC$_{1-6}$alkyl, heterocyclylC$_{1-6}$alkylaryl, or heterocyclylarylC$_{1-6}$alkyl;
or $R^7$ and $R^8$ together with the nitrogen they are attached to form a heterocyclyl;
W is heteroaryl or aryl; and
$R^1$ and $R^2$ are defined as in claim 1.

10. A pharmaceutical composition comprising a compound of claim 1, or a pharmaceutically acceptable salt thereof, and a therapeutically inert carrier.

11. A method for the treatment of systemic lupus erythematosus or lupus nephritis in a mammal in need thereof, which method comprises administering a therapeutically effective amount of a compound of claim 1, or a pharmaceutically acceptable salt thereof, to said mammal.

12. A pharmaceutical composition comprising a compound of claim 8, or a pharmaceutically acceptable salt thereof, and a therapeutically inert carrier.

13. A method for the treatment of systemic lupus erythematosus or lupus nephritis in a mammal in need thereof, which method comprises administering a therapeutically effective amount of a compound of claim 8, or a pharmaceutically acceptable salt thereof, to said mammal.

* * * * *